United States Patent
Mori et al.

(10) Patent No.: US 7,777,094 B2
(45) Date of Patent: Aug. 17, 2010

(54) PAPER DIAPER AND METHOD FOR MANUFACTURING EXTENSIBLE SHEET USED IN THE DIAPER

(75) Inventors: Yosuke Mori, Iyomishima (JP); Keiji Torigoshi, Iyomishima (JP); Hideki Saiga, Iyomishima (JP)

(73) Assignees: Daio Paper Corporation, Ehime (JP); Daio Paper Converting Co., Ltd., Ehime (JP)

( * ) Notice: Subject to any disclaimer, the term of this patent is extended or adjusted under 35 U.S.C. 154(b) by 1157 days.

(21) Appl. No.: 10/472,111

(22) PCT Filed: Mar. 14, 2002

(86) PCT No.: PCT/JP02/02407

§ 371 (c)(1),
(2), (4) Date: Jan. 29, 2004

(87) PCT Pub. No.: WO02/074213

PCT Pub. Date: Sep. 26, 2002

(65) Prior Publication Data

US 2004/0133180 A1 Jul. 8, 2004

(30) Foreign Application Priority Data

Mar. 15, 2001 (JP) .............................. 2001-074606
Mar. 16, 2001 (JP) .............................. 2001-075266
Mar. 16, 2001 (JP) .............................. 2001-076056

(51) Int. Cl.
*A61F 13/15* (2006.01)
*A61F 13/20* (2006.01)
(52) U.S. Cl. .............. 604/367; 604/385.24; 604/385.27
(58) Field of Classification Search ...............
604/385.24–385.31, 386–387, 398, 400–402, 604/367
See application file for complete search history.

(56) References Cited

U.S. PATENT DOCUMENTS 4,050,462 A 9/1977 Woon et al.

(Continued)

FOREIGN PATENT DOCUMENTS

EP 0 761 194 A2 3/1997

(Continued)

OTHER PUBLICATIONS

Patent Abstracts of Japan, Abstract of JP Publication No. 2002-273808 (Daioo Paper Converting KK), published Sep. 25, 2002.

(Continued)

*Primary Examiner*—Michele Kidwell
(74) *Attorney, Agent, or Firm*—Frishauf, Holtz, Goodman & Chick, P.C.

(57) ABSTRACT

A disposable diaper having: an elastic portion where a plurality of elastic members is provided along a width direction with an interval of not more than 7.0 mm in a longitudinal direction, and a non-elastic portion wherein the non-elastic portion is in a center of at least one of a front side and a back side and the elastic portion is provided in a region including right-and-left side portions except the non-elastic portion, and a difference between a maximum product width obtained when the body peripheral region is extended to a limit of extension in a product width direction and a contracted product width obtained when the body peripheral region is in a non-extended contraction state is from 100 to 250 mm in a state where the front side and the back side are overlapped.

16 Claims, 39 Drawing Sheets

U.S. PATENT DOCUMENTS

| | | | |
|---|---|---|---|
| 4,101,367 A * | 7/1978 | Maier | 156/471 |
| 4,486,192 A * | 12/1984 | Sigl | 604/385.21 |
| 4,795,454 A | 1/1989 | Dragoo | |
| 4,943,340 A | 7/1990 | Ujimoto et al. | |
| 5,476,458 A | 12/1995 | Glaug et al. | |
| 5,599,417 A | 2/1997 | Glaug et al. | |
| 5,601,544 A | 2/1997 | Glaug et al. | |
| 5,649,918 A | 7/1997 | Schleinz | |
| 5,735,839 A | 4/1998 | Kawaguchi et al. | |
| 5,833,678 A | 11/1998 | Ashton et al. | |
| 5,851,935 A * | 12/1998 | Srinivasan et al. | 442/328 |
| 5,938,652 A | 8/1999 | Sauer | |
| 5,993,433 A | 11/1999 | St. Louis et al. | |
| 6,049,916 A | 4/2000 | Rajala et al. | |
| 6,159,190 A | 12/2000 | Tanaka et al. | |
| 6,554,815 B1 | 4/2003 | Umebayashi | |
| 2003/0135189 A1 | 7/2003 | Umbbayashi | |
| 2004/0015146 A1 | 1/2004 | Torigoshi et al. | |
| 2004/0030317 A1 | 2/2004 | Torigoshi | |
| 2004/0166756 A1 * | 8/2004 | Kurihara et al. | 442/366 |

FOREIGN PATENT DOCUMENTS

| | | |
|---|---|---|
| EP | 1 027 874 A2 | 8/2000 |
| EP | 1027874 A2 | 8/2000 |
| EP | 1 184 012 A1 | 3/2002 |
| EP | 1 197 196 A1 | 4/2002 |
| EP | 1 205 169 A1 | 5/2002 |
| EP | 1 226 802 A2 | 7/2002 |
| EP | 1 384 459 A2 | 1/2004 |
| GB | 2 253 131 A | 9/1992 |
| JP | 01-183503 A | 7/1989 |
| JP | 04-259459 A | 9/1992 |
| JP | 04-364845 A | 12/1992 |
| JP | 05-076565 A | 3/1993 |
| JP | 6-421 | 1/1994 |
| JP | 09-197920 A | 7/1994 |
| JP | 06-254117 A | 9/1994 |
| JP | 06-327716 A | 11/1994 |
| JP | 07-117125 A | 5/1995 |
| JP | 07-236650 A | 9/1995 |
| JP | 08-019570 A | 1/1996 |
| JP | 08-191858 A | 7/1996 |
| JP | 08-280736 A | 10/1996 |
| JP | 09-056746 A | 3/1997 |
| JP | 09-056747 A | 3/1997 |
| JP | 09-084824 A | 3/1997 |
| JP | 09-154881 A | 6/1997 |
| JP | 09-271488 A | 10/1997 |
| JP | 09-295366 A | 11/1997 |
| JP | 09-299398 A | 11/1997 |
| JP | 09-299401 A | 11/1997 |
| JP | 10-029259 A | 2/1998 |
| JP | 10-504266 A | 4/1998 |
| JP | 10-201790 A | 8/1998 |
| JP | 11-058638 A | 3/1999 |
| JP | 11-076297 A | 3/1999 |
| JP | 11-107007 A | 4/1999 |
| JP | 11-188060 A | 7/1999 |
| JP | 11-253489 A | 9/1999 |
| JP | 11-299828 A | 11/1999 |
| JP | 11-318978 A | 11/1999 |
| JP | 2000-26015 A | 1/2000 |
| JP | 2000-126231 A | 5/2000 |
| JP | 2000-140014 A | 5/2000 |
| JP | 2000-140021 A | 5/2000 |
| JP | 2000-140022 A | 5/2000 |
| JP | 2000-279444 A | 10/2000 |
| JP | 2000-288017 A | 10/2000 |
| JP | 2000-296150 A | 10/2000 |
| JP | 2000-300603 A | 10/2000 |
| JP | 2001-000478 A | 1/2001 |
| JP | 2001-037808 A | 2/2001 |
| JP | 2001-157690 A | 6/2001 |
| JP | 2002-095692 A | 4/2002 |
| JP | 2002-102282 A | 4/2002 |
| JP | 2002-248127 A | 9/2002 |
| JP | 2002-272784 A | 9/2002 |
| JP | 2002-273808 A | 9/2002 |
| TW | 245955 | 4/1995 |
| WO | WO 96/04874 A1 | 2/1996 |
| WO | WO 00/76444 A1 | 12/2000 |

OTHER PUBLICATIONS

Patent Abstracts of Japan, Abstract of JP Publication No. 2002-272784 (Daioo Paper Converting KK), published Sep. 24, 2002.

Patent Abstracts of Japan, Abstract of JP Publication No. 2001-157690 (Kao Corp), published Jun. 12, 2001.

Patent Abstracts of Japan, Abtract of JP Publication No. 11-253489 (Kao Corp), published Sep. 21, 1999.

Patent Abstracts of Japan, Abstract of JP Publication No. 2000-126231 (Kao Corp), published May 9, 2000.

Patent Abstracts of Japan, Abtract of JP Publication No. 09-271488 (Toyo Eizai KK), published Oct. 21, 1997.

Supplemental European Search Report for EP 027056174.7, Applicant: Daio Paper Corporation, et al. dated Jul. 27, 2004.

Japanese Office Action dated Jun. 6, 2003 and English translation thereof issued in counterpart Japanese Appln. No. 2000-374192.

Japanese Office Action dated Aug. 6, 2003 and English translation thereof issued in counterpart Japanese Appln. No. 2001-075266.

Japanese Office Action dated Sep. 11, 2003 and English translation thereof issued in counterpart Japanese Appln. No. 2000-362489.

Japanese Office Action dated Jun. 27, 2008 and English translation thereof issued in counterpart Japanese Appln. No. 2000-371680.

Japanese Office Action (and English translation thereof) dated Sep. 18, 2008, issued in counterpart Japanese Application No. JP 2001-076056.

Japanese Office Action (and English translation thereof) dated Jul. 1, 2003, issued in counterpart Japanese Application No. JP 2001-074606.

Japanese Office Action (and English translation thereof) dated Jun. 20, 2008, issued in counterpart Japanese Application No. JP 2001-074606.

European Search Report dated Mar. 18, 2010 issued in counterpart European Application No. 02 705 174.7-2124.

* cited by examiner

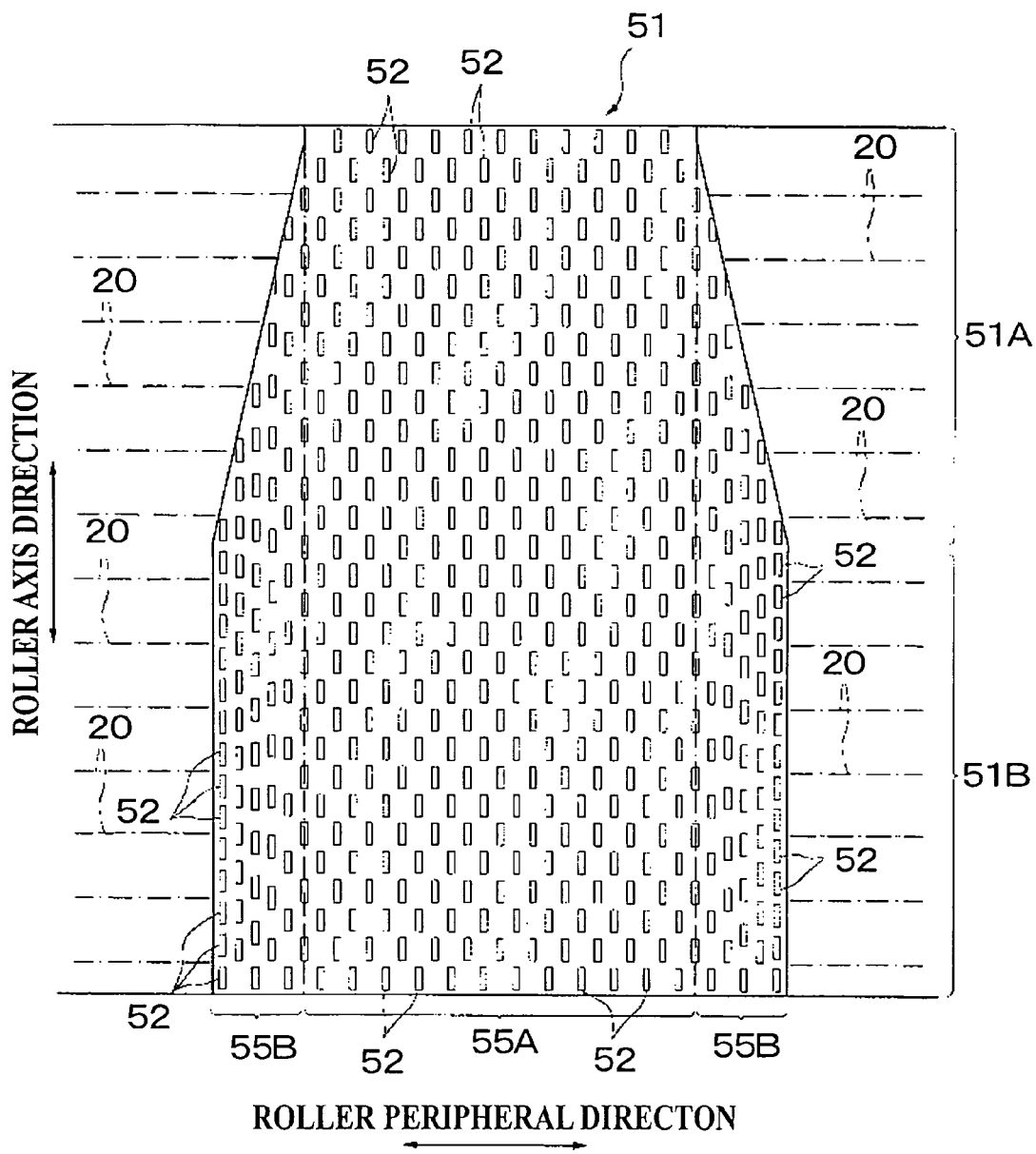

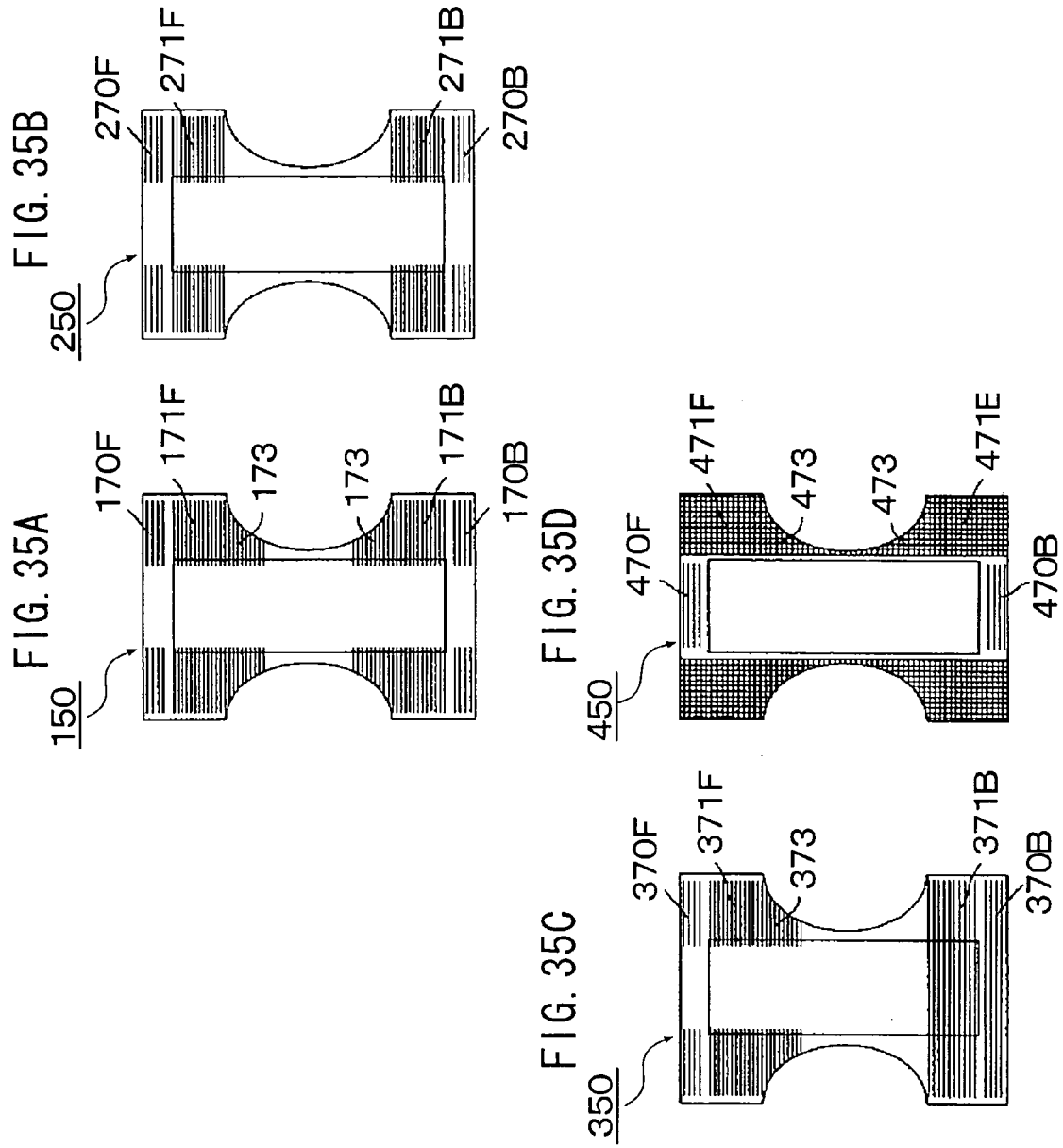

ROLLER AXIS DERECTION

FLOW DIRECTION

PAPER DIAPER AND METHOD FOR MANUFACTURING EXTENSIBLE SHEET USED IN THE DIAPER

This application is a U.S. National Phase Application under 35 U.S.C. 371 of International Application PCT/JP02/02407, filed Mar. 14, 2002.

FIELD OF THE INVENTION

The present invention relates to disposable diapers and method for manufacturing elastic sheet for the same.

BACKGROUND ART

Recently, pants-type disposable diapers have been widely used. Generally, the disposable diaper comprises a liquid permeable top sheet which locates at a side of a wearer, a liquid impermeable back sheet which locates at an opposite side of the wearer, and an absorbent body which is arranged between both these sheets at each center of a body peripheral region and a leg peripheral portion, such that double-faced adhesive tapes annexed to both end portions in the width direction of the body peripheral region in the back side are joined to the body peripheral region in the front side.

As shown in FIG. 39, a large number of body peripheral region elastic members 4F and 4B, and leg peripheral portion elastic members 5F and 5B (e.g., rubber threads, elastic film, or the like.) which extend in the width direction are arranged in the body peripheral region A10 and the leg peripheral portion 2 to be worn in a state where the body peripheral region A10 and the leg peripheral portion 2 certainly fit to a body trunk and hip of the wearer by the body peripheral region elastic members 4F and 4B, and leg peripheral portion elastic members 5F and 5B.

For the elastic member in this case, especially for the body periphery, typically rubber threads are used. The rubber threads are arranged throughout the circumference of a region unevenly distributed on a side of a waist opening edge of the body peripheral region (i.e., a region of a length range from the waist opening edge to a leg opening start end). It is general that an arrangement interval is 10 mm or more. Typically, the arrangement interval at the waist opening portion is made small, and to prevent excessive press at a ventral portion, the arrangement interval at an under waist portion (a portion at an under crotch side from the waist opening portion) is made large.

However, in the case of the above conventional disposable diaper, since the body peripheral region elastic members 4F and 4B and the leg peripheral portion elastic members 5F and 5B are also arranged on a portion corresponding to the absorbent body 3, the absorbent body 3 contracts as shown by arrows G1 and G2 due to elasticity of the body peripheral region elastic members 4F and 4B and the leg peripheral portion elastic members 5F and 5B. Then, a portion on which the body peripheral region elastic members 4F and 4B are arranged and an approximately center in a longitudinal direction which is a portion where body fluid stays in the absorbent body 3 particularly by expansion and contraction of the leg peripheral portion elastic members 5F and 5B contract to cause wrinkles. Thus, there has been a drawback that fitness between the absorbent body 3 and the hip portion is impaired and liquid leakage easily occurs.

In the conventional disposal diaper, an interval of three-dimensional gathers provided to protrude at the side of the wearer in both outer side edges of the absorbent body 3 becomes small due to contraction of the absorbent body 3, the three-dimensional gathers make inroads into a crotch portion when worn with displacement from side to side, and that has been a cause of leakage.

Thus, the pants-type disposable diaper where occurrence of clumsy wrinkles is prevented by providing a region having no elastic member in the body peripheral region is proposed. However, although this kind of pants-type disposable diaper make a good show, it have been difficult to be worn or to wear, and has slipped off in some cases. There has been a problem that the desired fitness feeling is not obtained.

Disposable wearing articles such as the above disposable diapers, disposable pants or the like are required to make a waist periphery, leg peripheries and a body periphery elasticizable to improve adhesiveness to the wearer. In this case, it can be also thought to utilize woven fabrics (stretch fabrics) where materials per se have elasticity, however, cost is too high to use it for disposal articles. Therefore, typically, a filamentous or obi-like elastic member is glued in a stretched state on a non-elastic sheet such as a non-woven fabric, a plastic film or the like to make the non-elastic sheet elasticizable.

To continuously manufacture such elastic sheet, a method is employed where while the non-elastic sheet is turned out from a roller and run, an elastic member is withdrawn from a roller and attached on the non-elastic sheet in a stretched state with a predetermined tension. However, there are some cases where a portion with no need of elasticity (hereinafter, non-elastic portion) and an elastic portion should be provided intermittently in a scanning direction of the sheet in terms of forms of disposable wearing articles or as a matter of convenience of cutting into individual products.

Although it is also thought for the non-elastic portion that the elastic portion is attached on the sheet without giving the tension, it is difficult in terms of manufacturing to promptly switch the stretched state with the tension to or from the state without the tension.

Therefore, typically, the non-elastic portion is provided by intermittently coating an adhesive on the sheet to provide an adhesive-applying portion and a non-applying portion alternately along the sheet scanning direction on the sheet, and cutting the elastic member present on the adhesive non-applying portion. Since the elastic member is not attached to the sheet on the adhesive non-applying portion, the elastic member cut at one site is stretched to the elastic member attached on the sheet to be relaxed, and stay there.

The method to cut the elastic member includes, for example, as the method described in Japanese Patent Laid-open Application No. 2000-26015, a method where the elastic member is cut by passing the sheet on which the elastic member is positioned between a first roller having a continuous linear convex portions (single-edged blade) continuing along a roller width direction and a second roller opposed thereto, and pressing or heating with the linear convex portions of the first roller.

However, in this conventional method, since cutting force is acted continuously and linearly along the roller width direction, the sheet portion where no elastic member exist is cut in some cases. Even when it is not cut, since the sheet such as non-woven fabric or the like becomes a thin film by heating and pressing, one sealing line with hard tactile remains across the portion where no elastic member exist. Thus, there has been a problem that both looks and wearing feeling become insufficient when made into products.

Thus, the present applicant has proposed a method for manufacturing elastic sheet wherein a laminate is made by positioning a single or a plurality of elastic members of filamentous, netty, sheet like or the like on a sheet or between upper and lower sheets in an extended state, the laminate is passed between a first roller wherein multiple convex portions are disposed on the surface and a second roller opposed to the first roller, and the elastic member of the laminate is cut by either one of pressing or heating between the convex portions of the first roller and the second roller.

According to such a method for manufacturing the elastic sheet, there are advantages obtained that there is no breaking of the sheet portion, wearing feeling becomes good because no linear hard sealing line remains or the like. However, due to a subsequent design change, necessity to partially regulate contractile force occurred in order to make a disposal wearing article further fit to a body shape as well as loosen constriction of the leg peripheries. As techniques for it, as shown in FIG. 40, the method where the elastic member is cut using a first roller wherein the convex portions are disposed in a region of a head-cutting home base shape in a constant pattern, i.e., using the first roller wherein a convex portion forming region is formed to have a region where a cutting length of the elastic member is gradually expanded, and the method where tensile force is modulated by modulating extensible force of each elastic member with making a cut location rectangular as being conventional, are studied, respectively. However, in the former case, it was found that staving and slivering of substrates occur in the range of signs Q1 and Q2 shown in the same figure only by changing the formation range of the convex portions. On the other hand, in the latter case, although it becomes possible to partially change the extensible force without causing staving and slivering of the sheet, it was difficult to apply for an actual manufacturing line because an extensive equipment change is accompanied.

The object of the present invention is to provide a disposable diaper which improves fitness to a wearer as well as certainly prevents leakage of body fluid, makes a fine showing, is easy to be worn and wear, and causes no slip off.

Another object of the present invention is to provide a method for manufacturing an elastic sheet used for disposable diapers, wherein cut of an elastic member without possibility of sheet breakage is made possible as well as a cutting location of the elastic member can be optionally changed without causing staving and slivering, and a disposable diaper using the elastic sheet.

DISCLOSURE OF THE INVENTION

To solve the above problems, according to the first aspect of the present invention, a disposable diaper in which a waist opening portion and right-and-left leg opening portions are formed in a use state comprises: an elastic portion where a plurality of elastic members is provided along a width direction with an interval of not more than 7.0 mm in a longitudinal direction, and a non-elastic portion where no elastic member is provided, at least at an under waist portion of a body peripheral region of a length range from a waist opening edge to a leg opening start end,
wherein the non-elastic portion is in a center of at least one of a front side and a back side and the elastic portion is provided in a region including right-and-left side portions except the non-elastic portion, and
a difference between a maximum product width obtained when the body peripheral region is extended to a limit of extension in a product width direction and a contracted product width obtained when the body peripheral region is in a non-extended contraction state is from 100 to 250 mm in a state where the front side and the back side are overlapped.

When looking a product, since eye-catching is a place which is the center (the center in the width direction), in the present invention, the non-elastic portion is provided in a center of at least one of the front side and the back side, there is no occurrence of wrinkle in this portion and the product makes good showing. Deformation of the absorbent body present in the center is prevented. Moreover, because the elastic portion is in the region including the right-and-left side portions except the non-elastic portion, and the difference of the product width in a usual state where the elastic portion contracts and the product width in a maximum extended state where the elastic portion is extended to a peripheral direction is made from 100 to 250 mm, the diaper becomes one which is easy to be worn or wear and is excellent in fitness feeling.

According to the second aspect of the invention, a disposable diaper in which a waist opening portion and right-and-left leg opening portions are formed in a use state comprises: an elastic portion where an elastic member is provided along a width direction, and a non-elastic portion where no elastic member is provided, at least at an under waist portion of a body peripheral region of a length range from a waist opening edge to a leg opening start end,
wherein the non-elastic portion is in a center of at least one of a front side and a back side and the elastic portion is provided in a region including right-and-left side portions except the non-elastic portion, and
an extensible force in a product width direction of the body peripheral region obtained when the body peripheral region is extended to the product width direction is in a range of 300 to 600 gf in a 100 mm contracted state with respect to a maximum product width in a limit of extension and is in the range of 50 to 300 gf in a 150 mm contracted state with respect to the maximum product width in the limit of extension, in a state where the front side and the back side are overlapped.

Although action effects on looks of the product and deformation prevention of the absorbent body are similar to those in the above first aspect, in the disposable diaper, because the elastic portion is in the region including the right-and-left side portions except the non-elastic portion, the extensible force of the body peripheral region of the product is in the range of 300 to 600 gf when the elastic portion is contracted at 100 mm from the maximum extended state where the elastic portion is maximally extended in the peripheral direction, and the extensible force of the body peripheral region of the product is in the range of 50 to 300 gf when it is contracted at 150 mm, the diaper becomes one which is easy to wear or to be worn and is excellent in fitness feeling.

Preferably, a mass of the elastic member is from 0.05 to 0.13 g per elastic portion of 100 mm×100 mm in the limit of extension state. Thereby, the diaper becomes one which is easy to wear or to be worn and is excellent in fitness feeling.

It is preferred that a total sum of lengths of the non-elastic portions in the width direction is from 15 to 40% of a body peripheral length.

A width of the elastic portion in the longitudinal direction may be in the range of 50 to 150 mm.

When the above numeric ranges are limited, the action effects mentioned above become still more remarkable.

More preferably, a percentage of a length at a maximum extension to the length in the usual state where the elastic member is contracted is from 250 to 350%.

When the tension of the body periphery is in the above numeric range, the action effects mentioned above become still more remarkable.

According to the third aspect of the present invention, a disposable diaper in which a waist opening portion and rightand-left leg opening portions are formed in a use state comprises: an elastic portion where a plurality of elastic members is provided along a width direction and over a length range of not less than 60% of the body peripheral region, and a non-elastic portion where no elastic member is provided at least at an under waist portion of a body peripheral region of a length range from a waist opening edge to a leg opening start end, wherein the elastic member is a netty elastic member, a nonporous film elastic member or a porous film elastic member, the non-elastic portion is provided in a center of at least one of a front side and a back side and the elastic portion is provided in a region including right-and-left side portions except the non-elastic portion, and a difference between a maximum product width obtained when the body peripheral region is extended to a limit of extension in a product width direction and a contracted product width obtained when the body peripheral region is in a non-extended contraction state is from 100 to 250 mm in a state where the front side and the back side are overlapped.

Even when the elastic member is the netty elastic member, the nonporous film elastic member or the porous film elastic member, the action effects similar to those in the above first and second aspects can be obtained.

According to the forth aspect of the invention, a disposable diaper comprises: a liquid permeable top sheet which is located at a side of a wearer, a liquid impermeable back sheet which is located at an opposite side of the wearer, and an absorbent body which is between both these sheets at a center of a body peripheral region and a leg peripheral portion, wherein a leg peripheral portion elastic member at least running to an outer side edge of the absorbent body at an approximately center in a longitudinal direction in the leg peripheral portion is provided in a range of the leg opening edge in the leg peripheral portion.

According to the disposable diaper, fitness to a hip portion is widely improved by elasticity of the leg peripheral portion elastic member, as well as the leg peripheral portion elastic member is provided at a portion running to at least the outer side edge of the absorbent body at the approximately center in the longitudinal direction in the leg peripheral portion in a range of the leg opening edge, therefore, the leg peripheral portion elastic member is not provided at a portion corresponding to the absorbent body or a portion except the outer edge of the absorbent body, thus there is no possibility that absorbability is impaired by contraction of the absorbent body, and there becomes no need to fear liquid leakage.

According to the fifth aspect of the invention, a disposable diaper comprises: a liquid permeable top sheet which is located at a side of a wearer, a liquid impermeable back sheet which is located at an opposite side of the wearer, and an absorbent body which is between both these sheets at a center of a body peripheral region and a leg peripheral portion, wherein a leg peripheral portion elastic member which is linked overstriding the absorbent body in a width direction in an approximately center in a longitudinal direction in the leg peripheral portion is provided in a range of the leg opening edge in the leg peripheral portion, and an elasticity lowering member which lowers an elasticity is provided to the leg peripheral portion elastic member which is disposed corresponding to the absorbent body among the leg peripheral portion elastic members.

According to the disposable diaper, the elasticity of the leg peripheral portion elastic member gives good fitness of the leg peripheral portion to the leg peripheral portion of the wearer, as well as the elasticity lowering member which lowers the elasticity is provided to the leg peripheral portion elastic member at the portion corresponding to the absorbent body, therefore, there is no possibility that the absorbability is impaired due to contraction of the absorbent body and there becomes no need to fear liquid leakage.

Preferably, a plurality of body peripheral region elastic members extending in the width direction is provided at the body peripheral region, an elasticity lowering member which lowers the elasticity being provided to the elastic member which is disposed corresponding to the absorbent body among the body peripheral region elastic members.

In this case, the elasticity of the body peripheral region elastic member gives good fitness of the body peripheral region to the body peripheral region of the wearer, as well as the elasticity lowering member which lowers the elasticity is provided to the body peripheral region elastic member at the portion corresponding to the absorbent body, therefore, there is no possibility that the absorbability is impaired due to contraction of the absorbent body and there becomes no need to fear liquid leakage.

A member to cut the body peripheral region elastic member may be employed as the elasticity lowering member.

In this case, the elasticity of the body and leg peripheral portion elastic members can be reduced only by cutting the body and leg peripheral portion elastic members, and thus the diaper can be manufactured with low cost.

Further, it is preferred that a plurality of body peripheral region elastic members extending in the width direction is provided at the portion from the width direction end portion in the body peripheral region at least to the outer side edge of the absorbent body.

In this case, the elasticity of the body peripheral region elastic member gives good fitness of the body peripheral region to the body peripheral region of the wearer, as well as a plurality of peripheral portion elastic members extending to the width direction is provided at the portion from the width direction end portion in the body peripheral region at least to the outer side edge of the absorbent body. Thus, no elastic member is provided at the portion corresponding to the absorbent body and the portion except the outer side edge of the absorbent body. Therefore, there is no possibility that the absorbability is impaired due to contraction of the absorbent body and there becomes no need to fear liquid leakage.

More preferably, an inner end portion of the body and leg peripheral portion elastic members is located in the inward than the outer side edge of the absorbent body.

In this case, the elastic members can be arranged as widely as possible in the width direction in the range where the absorbability of the absorbent body is not impaired, and thus the fitness to the wearer is further improved.

According to the sixth aspect of the invention, a disposable diaper comprises: a liquid permeable top sheet which is located at a side of a wearer, a liquid impermeable back sheet which is located at an opposite side of the wearer, and an absorbent body which is between both these sheets at a center of a body peripheral region and a leg peripheral portion, wherein a plurality of body peripheral region elastic members which extend in the width direction except a portion corresponding to the absorbent body or a portion not corresponding to at least both outer side edges of the absorbent body are provided only at the body peripheral region.

According to the disposable diaper, no elastic member is provided at the leg peripheral portion, therefore, there is no possibility that the absorbability is impaired due to contraction of the absorbent body at a crotch portion and there becomes no need to fear liquid leakage. Furthermore, the elasticity of the body peripheral region elastic member gives good fitness of the body peripheral region to the body peripheral region of the wearer, as well as no elastic member is arranged at the portion corresponding to the absorbent body and the portion except the outer side edges of the absorbent body, therefore, there is no possibility that the absorbability is impaired due to contraction of the absorbent body and there becomes no need to fear liquid leakage.

Preferably, an inner end portion of the body peripheral region elastic member is located in the inward than the outer side edge of the absorbent body.

In this case, the elastic members can be arranged as widely as possible in the width direction in the range where the absorbability of the absorbent body is not impaired, and thus the fitness to the wearer is further improved.

According to the seventh aspect of the invention, a disposable diaper comprises: a liquid permeable top sheet which is located at a side of a wearer, a liquid impermeable back sheet which is located at an opposite side of the wearer, and an absorbent body which is between both these sheets at a center of a body peripheral region and a leg peripheral portion, wherein a plurality of body peripheral region elastic members which extend in the width direction is provided only at the body peripheral region and an elasticity lowering member which lowers an elasticity is provided to the body peripheral region elastic member which is disposed corresponding to the absorbent body among the body peripheral region elastic members.

According to the disposable diaper, no elastic member is provided at the leg peripheral portion, therefore, there is no possibility to impair the absorbability due to the contraction of the absorbent body at the crotch portion and there becomes no need to fear the liquid leakage. Furthermore, the elasticity of the body peripheral region elastic member gives good fitness of the body peripheral region to the body peripheral region of the wearer, as well as the elasticity lowering member which lowers the elasticity is provided to body peripheral region elastic members at the portion corresponding to the absorbent body, therefore, there is no possibility to impair the absorbability due to the contraction of the absorbent body and there becomes no need to fear the liquid leakage.

Preferably, a member to cut the body peripheral region elastic member is employed as the elasticity lowering member.

In this case, the elasticity of the body and leg peripheral portion elastic members can be reduced only by cutting the body and leg peripheral portion elastic members, and thus the diaper can be manufactured with low cost.

It is preferred that a three-dimensional gather which rises at the side of the wearer are provided at both the outer side edges of the absorbent body, the rising start point of the three-dimensional gather being located in the inward side from the outer side edge of the absorbent body lower portion.

In this case, since a rising dimension of the three-dimensional gather from the outer side edge of the absorbent body do not become so large, the dimension between the three-dimensional gather can be enlarged. Thus, even when the wearing is not performed accurately, there becomes no fear that the diaper breaks into the legs.

According to the eighth aspect of the invention, a method for manufacturing an elastic sheet comprises the steps of:

making a laminate by disposing a plurality of elastic members with filamentous, netty, sheet-shaped or the like on a sheet face or between upper and lower sheets in an extended state;

passing the laminate between a first roller on which a plurality of convex portions are arranged in a predetermined region on a surface of the first roller, a convex portions row having a predetermined line pressure which is adjusted by changing an interval of the convex portions row along the roller axis direction for at least a portion and a second roller opposed to the first roller; and cutting the elastic member of the laminate by at least either one of pressing or heating between the convex portion of the first roller and the second roller.

According to the ninth aspect of the invention, a method for manufacturing an elastic sheet comprises the steps of:

making a laminate by disposing a plurality of elastic members with filamentous, netty, sheet-shaped or the like on a sheet face or between an upper and lower sheets in an extended state;

passing the laminate between a first roller on which a plurality of convex portions are arranged in a predetermined region on a surface of the first roller, a line pressure of a convex portion row along the roller axis direction being nearly equal for at least a portion of the convex portions by changing an interval of the convex portions row along the roller axis direction and a second roller opposed to the first roller; and cutting the elastic member of the laminate by at least either one of pressing or heating between the convex portion of the first roller and the second roller.

First, since no cutting force acts to the elastic member of the portion other than the convex portion, portions which is cut and is not cut are produced in the elastic member and lead-in due to the cut of elastic member becomes partial. Thus it becomes a sheet with less feelings for foreign matters, which is good for wearers. Since no cutting force acts between the convex portion and the convex portion, even when the cutting force acts such that the sheet in the roller axis direction is cut, it can be prevented that the sheet portion corresponding a portion between the convex portion and the convex portion is cut. Thus, even if the sheet is partially cut, a situation where it is linearly broken unlikely occurs. The sheet can be also such that it is partially cut to improve air permeability of the sheet.

The present inventors have studied causes for occurrence of staving and slivering when tried to cut the elastic member by the first roller in a tilting direction but not vertical direction against an arranged direction of the elastic member, and then it has been confirmed that the line pressure due to the convex portion is too high at Q1 and Q2 regions (see FIG. 40) which are short in convex portion forming interval length of the roller axis direction.

Thus, in the eighth aspect of the invention, the convex portion disposing interval of the roller axis direction was changed for at least a portion of the convex portions to reduce the line pressure to the degree that the line pressure causes no staving by adjusting the line pressure of the convex portion row along the roller axis direction. In the ninth aspect of the invention, the convex portion disposing interval of the roller axis direction was changed for at least a portion of the convex portions to make a line pressure of a convex portion row along the roller axis direction nearly equal. As a result, there becomes no region where the line pressure elevates locally, and the elastic member becomes possible to be cut without causing staving and slivering.

That is, according to the method for manufacturing the elastic sheet of the present invention, the cut of elastic member is made possible with no possibility of sheet breakage, as well as it becomes possible that a cutting position of the elastic member is optionally changed without causing staving and slivering of the substrate.

In the method for manufacturing the elastic sheet of the present invention, the elastic member may be glued by coating an adhesive on at least one of the upper and lower sheets and sandwiching the elastic member between the upper and lower sheets.

suitably used are those where

Preferably, as a specific structure of the first roller, in the predetermined region on a surface, the convex portion with a length in the roller axis direction of 1 to 25 mm and a width in a roller peripheral direction of 0.5 to 15 mm is disposed in a lattice or a staggered pattern in the roller axis direction and in the roller peripheral direction, and it is preferable that a value or an approximate value thereof obtained by multiplying a ratio of a formation interval length in the roller axis direction of the convex portion row to a formation interval length in the roller axis direction of a standard portion convex portion row to a disposition pitch of the convex portion row of the standard portion is rendered a disposition pitch in the roller axis direction of the convex portions in the convex portion row where at least the formation interval length of the convex portion row in the roller axis direction is unequal to a convex portion formation interval length of a standard portion.

Further, a plane shape of the convex portions may be, for example, a lattice, linear or polygonal shape, and these are disposed in a lattice pattern, or preferably in a staggered lattice pattern to ensure cutting. An adhesive may be coated on at least one of the sheet and the elastic member along the longitudinal direction continuously or discontinuously, or partially or entirely.

In the meantime, in a disposable diaper which is made by attaching the elastic sheet manufactured by the method described above to an elasticity imparted portion, it becomes one with soft tactile impression for the wearer and good looks.

BRIEF DESCRIPTION OF THE DRAWINGS

FIG. 20 is a developed view showing an emboss portion of the emboss heat roller in FIG. 17;

FIG. 35A is an illustration showing an arranged mode of the elastic members of the disposable diaper according to the invention;

FIG. 35B is an illustration showing an arranged mode of the elastic members of the disposable diaper according to the invention;

FIG. 35C is an illustration showing an arranged mode of the elastic members of the disposable diaper according to the invention;

FIG. 35D is an illustration showing an arranged mode of the elastic members of the disposable diaper according to the invention;

BEST MODE FOR CARRYING OUT THE INVENTION

Hereinafter, in reference to the drawings, embodiments of the invention are described in detail.

First Embodiment

Figure 2:
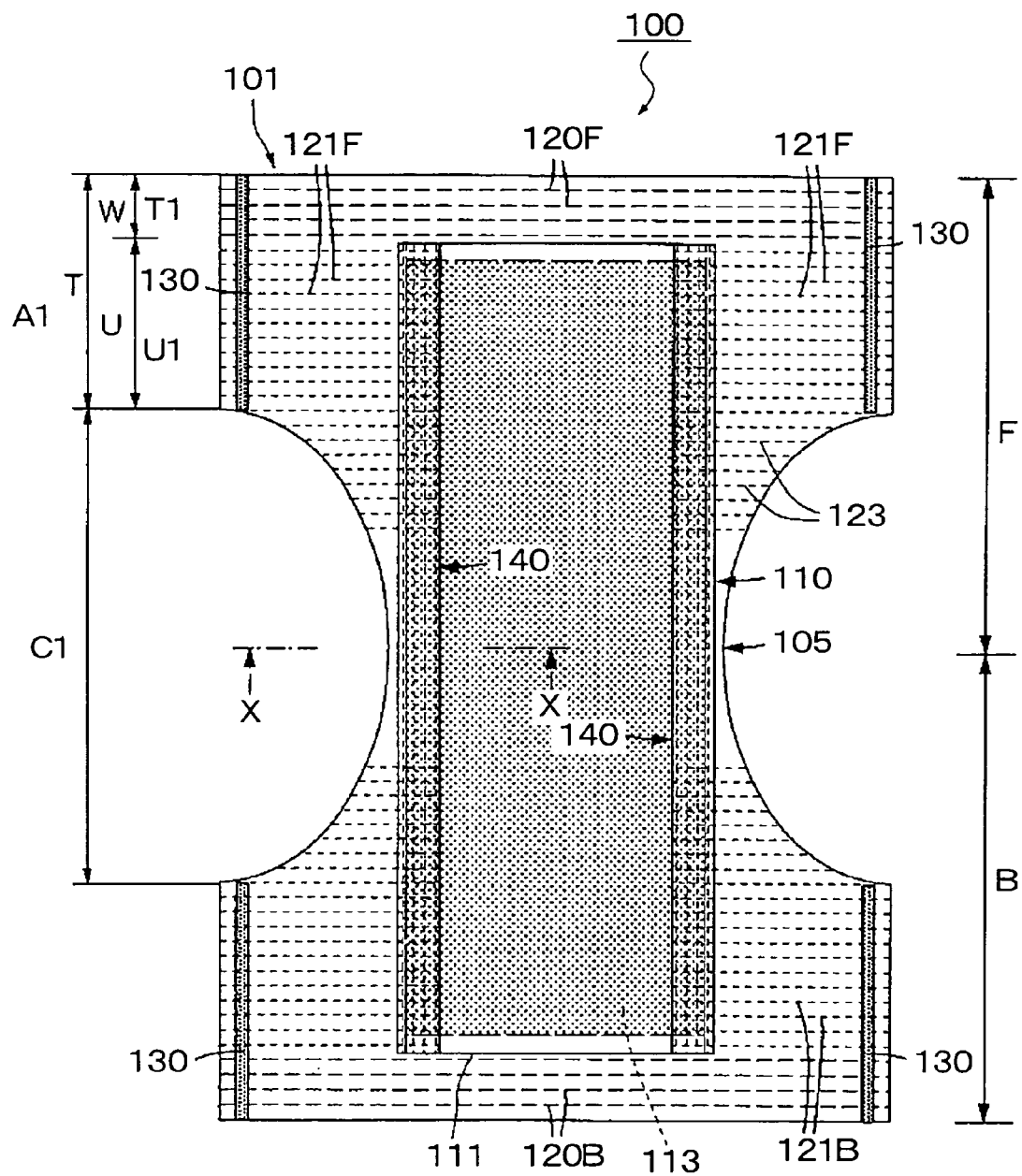
FIG. 2 is a development plan view of a disposable diaper according to the first embodiment of the invention.

As shown in FIG. 2, the pants-type disposable diaper 100 according to the first embodiment mainly comprises a flexible external sheet 101, and an absorbent body 110 which is fixed to an inner face of the external sheet 101 and extends in a longitudinal direction (front and back direction) with a leg peripheral portion 105 as a center.

Figure 4:
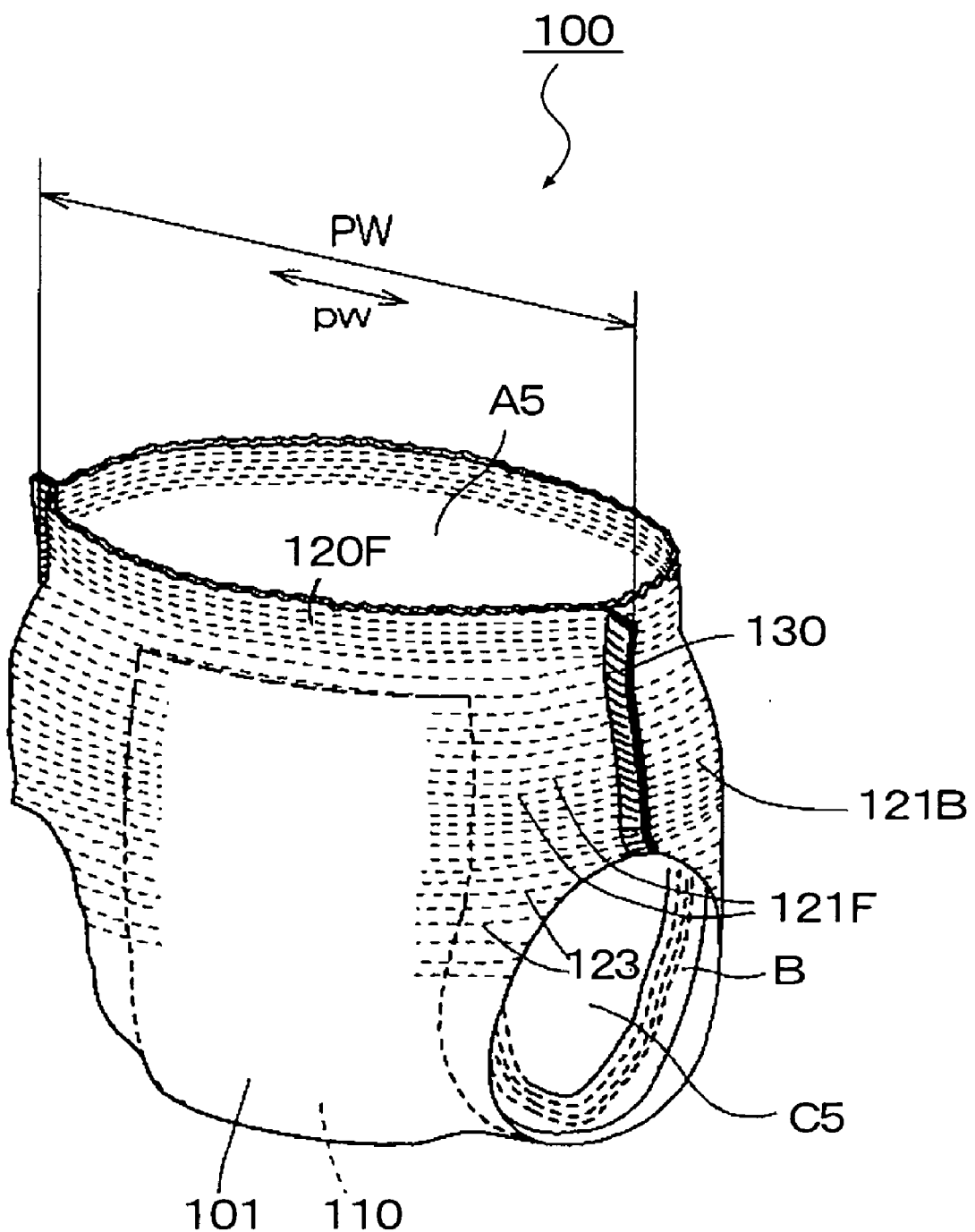
FIG. 4 is a perspective view showing the first embodiment product.
Figure 5:
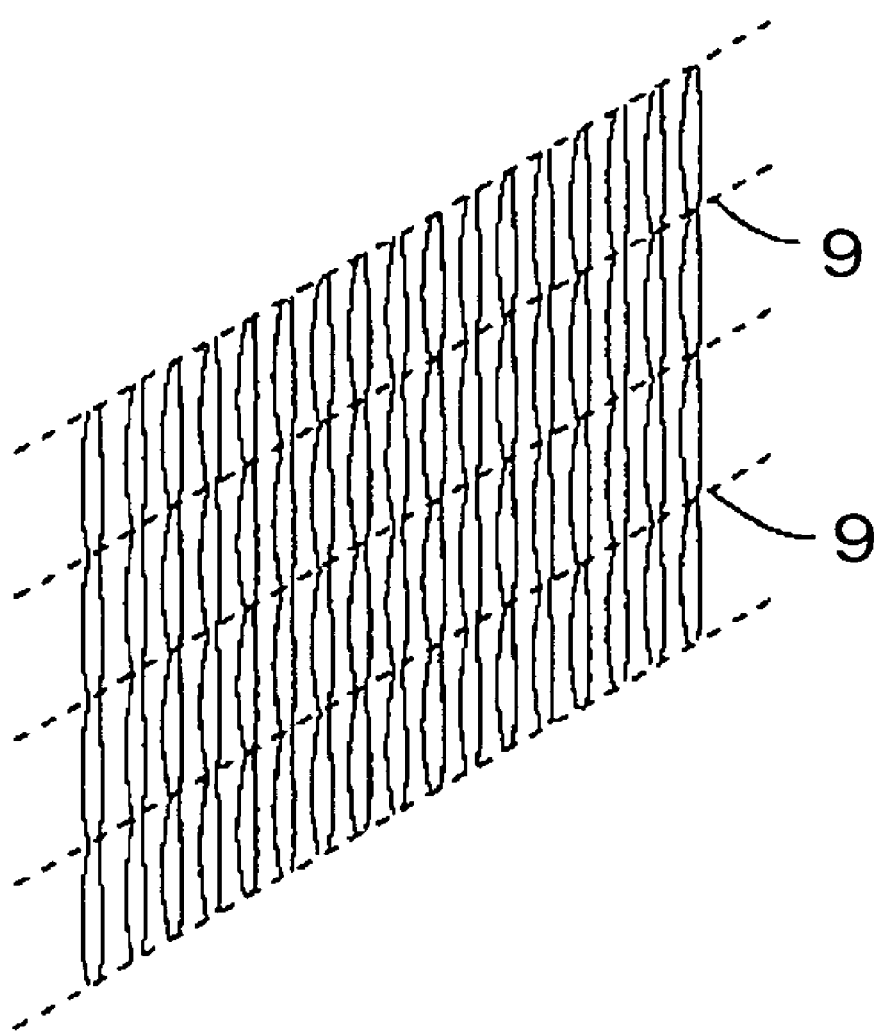
FIG. 5 is an occurrence status schematic view of wrinkles of the product of the present invention.

The external sheet 101 is made by laminating and fixing two or three or more breathable/water-repellent non-woven fabric. As shown in FIG. 4, a waist opening portion A5 and a pair of right-and-left leg opening portions C5 are formed by joining an entirety of the longitudinal direction of both side edge portions of a front side F and a back side B in the final stage of the process for manufacturing after overlaying the external sheet 1 and the absorbent body 110 (make this joint portion a sign 130).

Throughout herein, the term "longitudinal direction" means the direction binding a ventral side and a dorsal side, and the term "width direction" means the direction perpendicular to the longitudinal direction. The term "waist opening edge" means an edge of the waist opening portion A5, and the term "leg opening edge" means the edge of the leg opening portion C5. The term "leg opening start end" means a location where the leg opening edge of the leg opening portion C5 and the joint portion 130 intersect, and has a meaning of a site where the leg opening edge starts. The term "body peripheral region" (e.g., A1 in FIGS. 1 and 2) means a whole region of the length range from the waist opening edge to the leg opening start end. The body peripheral region T can be conceptually divided into "waist portion" (e.g., T1 in FIGS. 1 and 2) and "under waist portion" (e.g., U1 in FIGS. 1 and 2). The length in the longitudinal direction thereof is different depending on product sizes, and is from 15 to 40 mm for the waist portion T1 and from 65 to 120 mm for the under waist portion U1.

The term "product width" referred to in the invention means a distance between both side edges at the product. When the product width of the body peripheral region is different at the waist portion T1 and the under waist portion U1, especially it is rendered as the width at the under waist portion U1. A product width direction is the direction along the product width. In FIG. 4, the product width and the product width direction are represented by PW and pw, respectively. Therefore, the maximum product width is the product width when the body peripheral region is stretched to the product width direction and the elastic portion is extended to extension limit at the product in the state where the front side and the back side are overlapped. A contraction width is the product width when the elastic portion is in the contraction state where it is not extended at the product in the state where the front side and the back side are overlapped.

On the other hand, a total sum of lengths in the width direction of non-elastic portions referred to in the invention is referred to the sum of each width direction length when non-elastic portions are present in the front side and the back side, respectively, and is the length of the width direction when non-elastic portion is present at only one site at the body peripheral region.

The term "leg opening portion" (e.g., C1 in FIGS. 1 and 2) means the whole region of the length range which forms the leg opening portion C5. The term "center" means an intermediate region excluding the side portions including a centerline of the product. The term "side" means both side portions at the body peripheral region A1.

Figure 3:
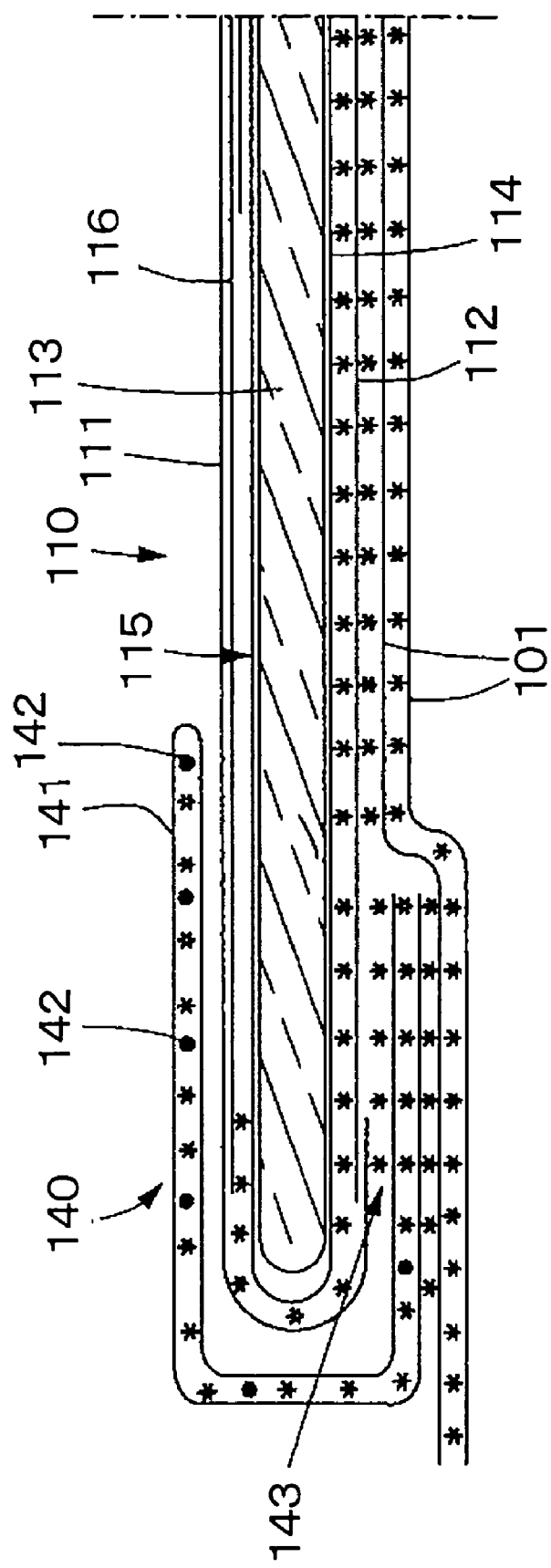
FIG. 3 is a view on arrow taken on line X-X in FIG. 2.

As is also shown in FIG. 3, the absorbent body 110 comprises the rectangular liquid permeable top sheet 111 which is made up of non-woven fabric and the like and directly contacts with skin of the wearer, an absorbent body 115 made up of a rectangular absorbent core 113 having stiffness to some extent where flocculent pulp is the subject and forehead winded rectangular crepe paper 114 enfolding whole upper and lower faces thereof and a rectangular liquid impermeable back sheet 112 made up of polyethylene plastic film and the like which reaches vicinity of both side edges in a back face of the absorbent body 115, wherein the liquid permeable top sheet 111 makes the round of the both side edges of the absorbent body 115, reaches the back side, is overlapped on the liquid impermeable back sheet 112, and these respective elements are integrated by attaching with a hot melt adhesive (those represented by * in the figure are attached portions). As shown in the figure, a liquid permeable second sheet 116 can be intervened between the liquid permeable top sheet 111 and the crepe paper 114 if necessary. The absorbent body 110 is integrated to the external sheet 101 by attaching nearly entire back face with the hot melt adhesive.

Leg peripheral rising cuffs 140 (three-dimensional gathers) which protrude at the side of the use are formed at both side portions of the absorbent body 110, respectively. The rising cuffs comprises a rising sheet 141 which substantially continues to the width direction and elastic member(s), for example, one or a plurality of elastic members 142, 142, . . . made up of rubber threads as shown in the figure.

More particularly, the rising cuffs 140 are formed by doubling the rising cuffs 141, and are formed by enfolding respective elastic members 142, 142, . . . in the fixing state by the hot melt adhesive. It is desirable that the rising sheet 141 which forms each rising cuffs 140 is not liquid permeable and is liquid impermeable or hydrophobic. Also, it may have a nature to repel liquids by giving a silicon treatment to a liquid permeable sheet such as non-woven fabric. Further, it is desirable to have air or vapor permeability.

The inner face of the double rising sheets 141 makes the round of the back face side of the absorbent body 115 and the liquid impermeable back sheet 112, and is firmly fixed with the hot melt adhesive and the like. As a result, the firm fixation start end of the double rising sheets 141 forms a rising end (rising start point) 143 of the rising cuffs 140.

A forefront side from the rising end 143 is a free portion which is not fixed to the product body.

In the meantime, in front and back end portions of the longitudinal direction, the free portion is fixed to the product by the hot melt adhesive and the like in the state where the front heads for a central side of the product, specifically fixed to an outer face of the liquid permeable top sheet 111.

It is a basic mode that at least one of the elastic members 142, 142, . . . is in the free portion, however especially it is preferred that the elastic member 142 is at a front portion of the free portion, and further, as shown in FIG. 3, it is preferable to have the elastic member at a root side. As is shown in the figure, it is desirable to have a plurality of members at the root portion.

FIG. 2 shows the state where the diaper is developed in the longitudinal direction. Since the disposable diaper is worn to a body in a boat form in wearing and contraction force of respective elastic members 142, 142, . . . acts, the front and back ends of the product are as they are and the rising cuffs 140 rise by the contraction force of the respective elastic members 142, 142, . . . at the leg peripheries. Then, the side portions of the absorbent body 110 are deformed and raised, and the absorbent body is also slightly raised with being deformed to form deep packet space.

Space surrounded by right-and-left rising cuffs 140, 140 forms the space to confine urine or loose stool. When urine is excreted into the space, the urine passes through the liquid permeable top sheet and is absorbed in the absorbent body element 115, as well as for solids of loose stool, the rising cuffs 140 become barriers and its overleaping is prevented.

In the meantime, in the longitudinal direction end portion of the front side F and the back side B, waist elastic member 120F and 120B made up of thin rubber threads parallel to the end edge of the waist opening portion A5 with intervals are positioned and fixed under extension to extend and contract between non-woven fabrics of the external sheet 101 at the waist portion T1 in order to enhance fitness of the waist periphery. The interval and the number of the waist elastic members 120F, 120B at the waist portion W can be appropriately determined, however for example, it is preferred that the interval is from about 4 to 8 mm and the number is from about 4 to 10.

Under such configuration, according to the present invention, under waist portion elastic members 121F, 121B along the width direction are provided at an underbelly portion of the front side F and a hip portion of the back side B in the under waist portion U1 which is the portion from the waist portion T1 to the leg opening portion C1 of the front side F and back side B. The under waist portion elastic members 121F, 121B are provided at left-and-right sides of the product except near entirety of the absorbent core 113 among the portions from one side joint portion 130 to the other side joint portion 130 in the front side F and the back side B. At that time, considering the form of the general pants-type disposable diaper, it is desirable that the width in the longitudinal direction of an elastic portion where the under waist portion elastic members 121F, 121B are provided is made from 50 to 150 mm. It is desirable that non-elastic portions where the under waist portion elastic members 121F, 121B are not provided are made such that the total sum of the peripheral direction length is from 15 to 40% of the peripheral length of the body periphery.

Further in the present invention, configured is such that the difference between the maximum product width obtained when the body peripheral region is extended to the limit of extension in the product width direction and the contracted product width obtained when the body peripheral region is in the non-extended contraction state is from 100 to 250 mm, and especially suitably from 150 to 200 mm in the state where the front side and the back side are overlapped, or made is such that an extensible force in the product width direction of the body peripheral region when the body peripheral region is extended to the product width direction is in the range of 300 to 600 gf in the state contracting 100 mm for the maximum product width in the limit of extension and is in the range of 50 to 300 gf in the state contracting 150 mm for the maximum product width in the limit of extension in the state where the front side and the back side are overlapped. This can be accomplished, for example, by the following configuration.

If in the form of general pants-type disposable diaper, it is desirable that the maximum product width is from 300 to 400 mm. It is desirable that a weight of the under waist portion elastic member at the elastic portion is from 0.05 to 0.13 g per 100 mm×100 mm elastic portion in the state of the extension limit.

On the other hand, it is desirable that a mutual interval of the under waist portion elastic members 121F and 121B is the same as or shorter than the interval of the waist elastic members 121F and 120B. The rubber threads used as these under waist portion elastic members 121F and 121B can be smaller than or substantially equivalent to the thin rubber threads used as the above waist elastic member 120 in intention stress and sectional outer diameter, and suitably the length at the maximum extension is from 250 to 350%, and especially from 250 to 300% of the length at usual contraction.

In the example shown in the figure, as these under waist portion elastic members 121F and 121B, thin rubber threads, specifically the elastic members of which thickness is 620 dtex or less are used, the interval in the longitudinal direction is 7.0 mm or less, and respectively parallel from 15 to 40 members are positioned and fixed between the non-woven fabric of the external sheet 1 in both of the front side F and the back side B. In this way, as is schematically shown in FIG. 4, generated wrinkles are narrow in width in the width direction, short in length in the longitudinal direction (direction perpendicular to the width direction), and generated in the form where the wrinkles continue in nearly longitudinal direction. Concavity or convexity of each wrinkle is extremely small. Furthermore, there is scarcely constriction at the rubber thread 9 portions, and it is difficult to discriminate the presence of the rubber thread 9 when a color of the sheet composing an outer surface and a color of the rubber thread 9 are the same color.

As a result the pants-type disposable diaper can be obtained in which the wrinkles are not noticeable and are fine texture even if viewable, and which exhibits the outer surface with flat plane and is excellent in simple feeling, i.e., without obstructive feelings and excellent in looks. Furthermore, no rubber trace is produced by pressing to skin as the face and by no topical excessive press to skin, and fitness is good and slip-off of the product is prevented because friction of inner face of the product and skin run to the entirety and the inner face of the product and the skin contact completely.

On the other hand, in the first embodiment, the leg opening portion elastic members 123 are provided at right-and-left portions except the center of the leg opening portion C1. For the leg opening portion elastic member 123, as with the under waist portion elastic members 121F and 121B, the elastic member of which thickness is 620 dtex or less can be positioned and fixed between the non-woven fabrics by making the interval of the longitudinal direction 7.0 mm or less.

Figure 1:
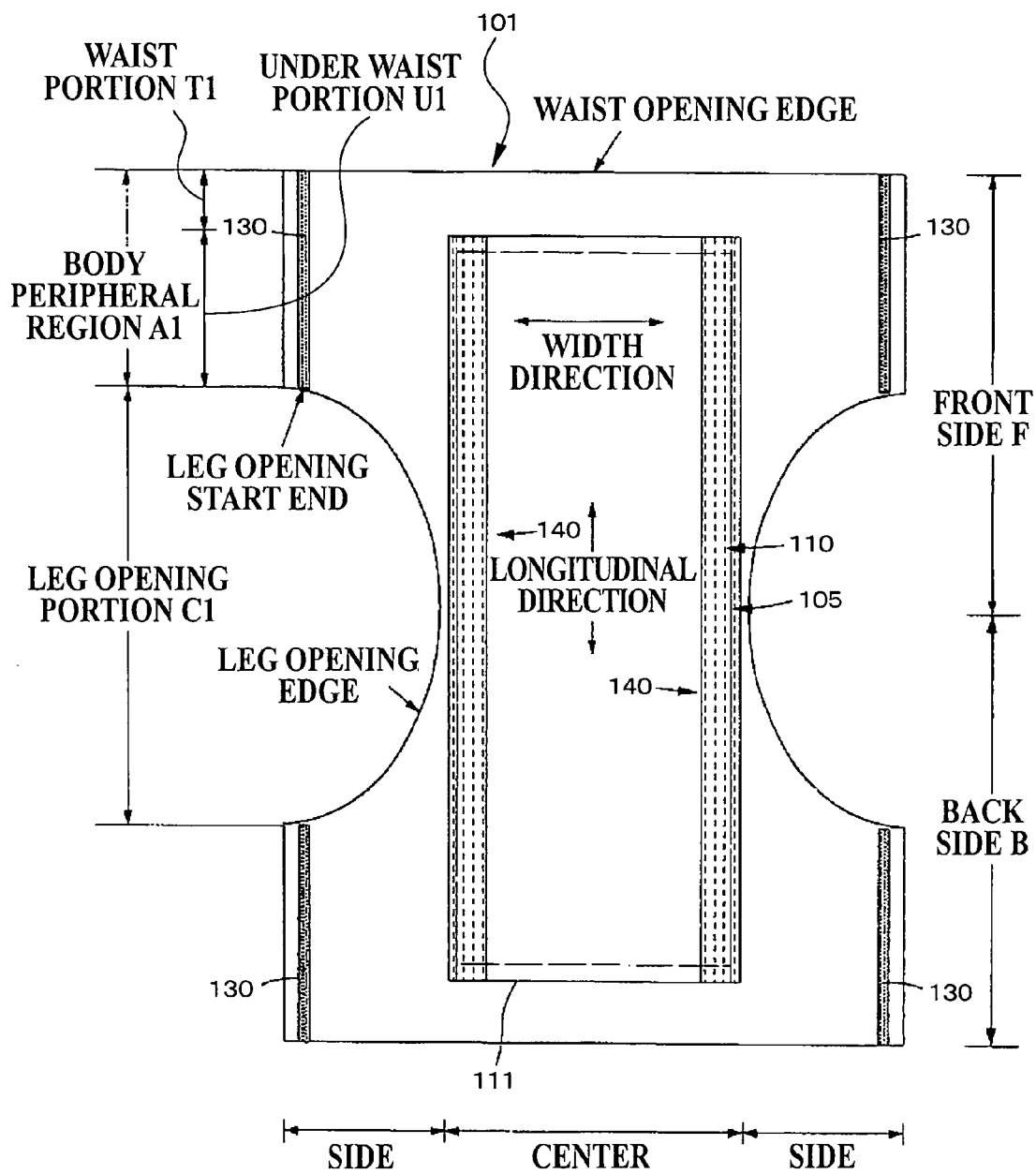
FIG. 1 is a development plan view of the first embodiment for term description of the invention.
Figure 6:
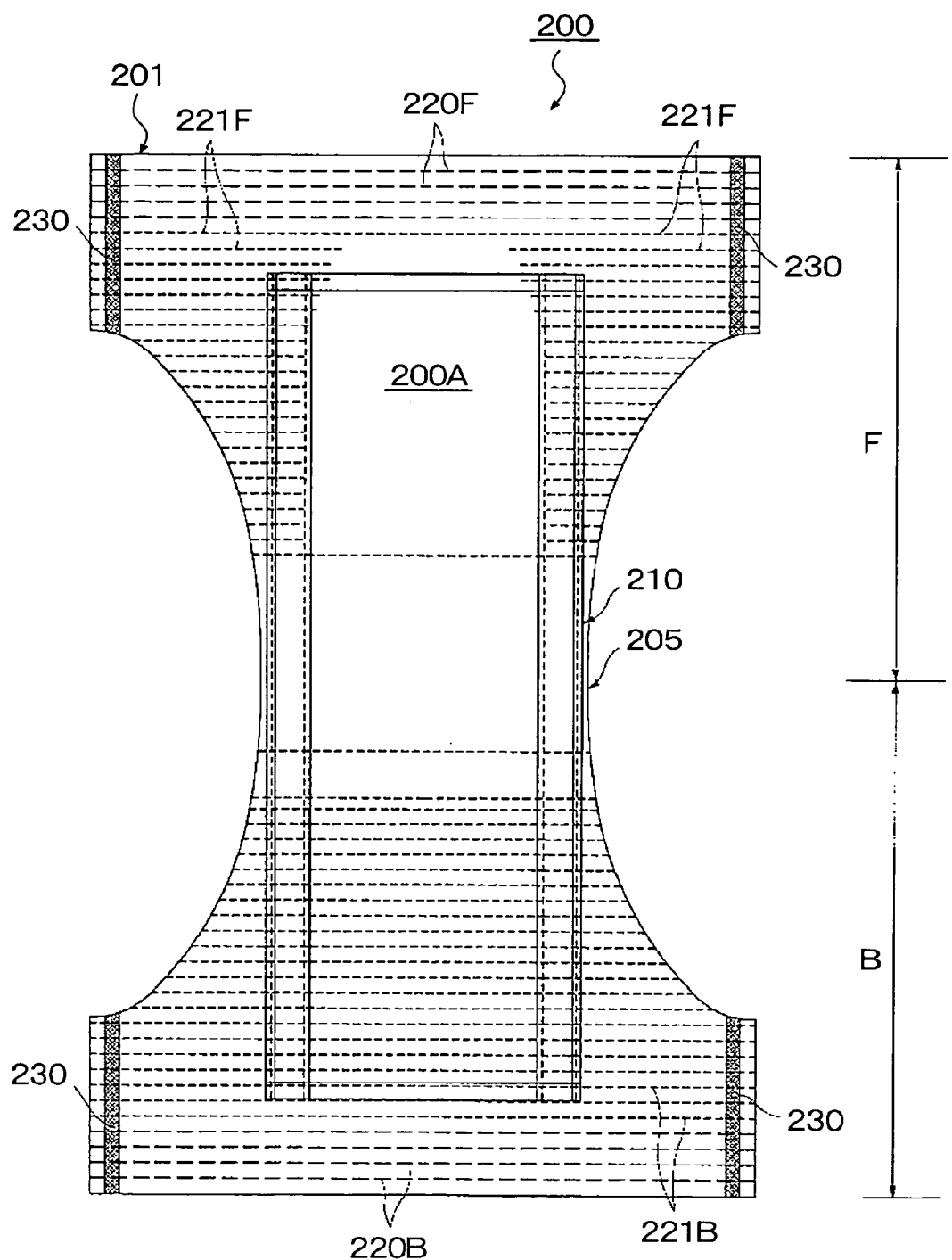
FIG. 6 is a development plan view showing the disposable diaper according to the second embodiment of the invention.

The disposable diaper configured in this way becomes the product where the difference between the maximum product width obtained when the body peripheral region is extended to limit of extension in the product width direction and the contracted product width obtained when the body peripheral region is in the non-extended contraction state is from 100 to 250 mm, and the extensible force in the product width direction of the body peripheral region when the body peripheral region is extended to the product width direction is in the range of 300 to 600 gf in the state contracting 100 mm for the maximum product width in the limit of extension and is in the range of 50 to 300 gf in the state contracting 150 mm for the maximum product width in the limit of extension in the state where the front side and the back side are overlapped, and thus becomes one which is easy to be worn and to wear and excellent in fitness feeling Second Embodiment The pants-type disposable diaper 200 shown in FIG. 6 as with FIG. 1 mainly comprises a flexible external sheet 201 and an absorbent body 210 which is fixed to an inner face of the external sheet 201 and extends to a longitudinal direction (front and back direction) with making leg peripheral portion as a center. The interval and the number of the waist elastic members 220F and 220B of the pants-type disposable diaper 200 in FIG. 6 can be appropriately determined, however, for example, it is preferred that the interval is from about 4 to 6 mm and the number is from about 5 to 7. Besides here, the under waist elastic member at the front side and the under waist elastic member at the back side are rendered an underbelly portion elastic member and a hip portion elastic member, respectively.

Further, the underbelly portion elastic member 221F is provided along the width direction at an underbelly corresponding site of the front side F, and the hip portion elastic member 221B is provided along the width direction at a hip portion corresponding site of the back side B. These underbelly portion elastic member 221F and the hip portion elastic member 221B are provided by the elastic sheet of the present invention described below. That is, in the process to run a lower sheet 10 where the length of the front side F and the back side B is substantially rendered a width, the elastic member 20 (220F, 220B, 221F, 221B) is positioned in the extended state and is sandwiched with the lower sheet 10 and an upper sheet 30 with the same width to make a laminate, subsequently, the laminate is passed between the first roller 50 where a plurality of convex portions are disposed on the surface and the second roller 59 opposed to the first roller, and the elastic member of the laminate 20, the elastic members 20, 20, . . . at 200A portion in the figure are cut by either one of pressing or heating between the convex portion 52 of the first roller 50 and the second roller 59 (see FIG. 17).

In the underbelly portion elastic member 221F of the present example, the portion 200A corresponding to the center of the absorbent body in the portion from one side joint portion 230 to the other side joint portion 230 at the front side F is discontinuously formed by cutting according to the method of the invention described above. On the other hand, as with conventional ones, the hip portion elastic member 221B is continuously provided from one side joint portion 230 to the other side joint portion 230 at the back side B. Also, a discontinuous side of the underbelly elastic member 221F and a side end of an opposite side run on to both ends of the hip portion elastic member 221B, respectively.

In the example shown in the figure, as these underbelly portion elastic member 221F and hip portion elastic member 221B, the elastic member made up of thin rubber threads which are respectively parallel from 9 to 25 members is positioned and fixed between the non-woven fabrics of the external sheet 1 to extend under extension both at the front side F and the back side B. The mutual interval of the underbelly portion elastic member 221F and hip portion elastic member 221B is equivalent to or shorter than the interval of the waist elastic members 221F and 220B.

The rubber threads used as these underbelly portion elastic member 221F and hip portion elastic member 221B can be made one which is smaller than or substantially equivalent to thin rubber threads used as the waist elastic member 220 described above in intension stress and sectional outer diameter. Simply, the use of the quite same rubber threads in both can correspond, however, discrimination such as color coding other than the above properties may be contemplated. As the thin rubber threads used herein, specifically, those where the intension stress is in the range of 4 to 17 g, especially from 5 to 10 g at the extension of 150% are suitably used, and those where the sectional outline is in the range of 100 to 350 μm, especially from 120 to 270 μm are suitably used.

Figure 7:
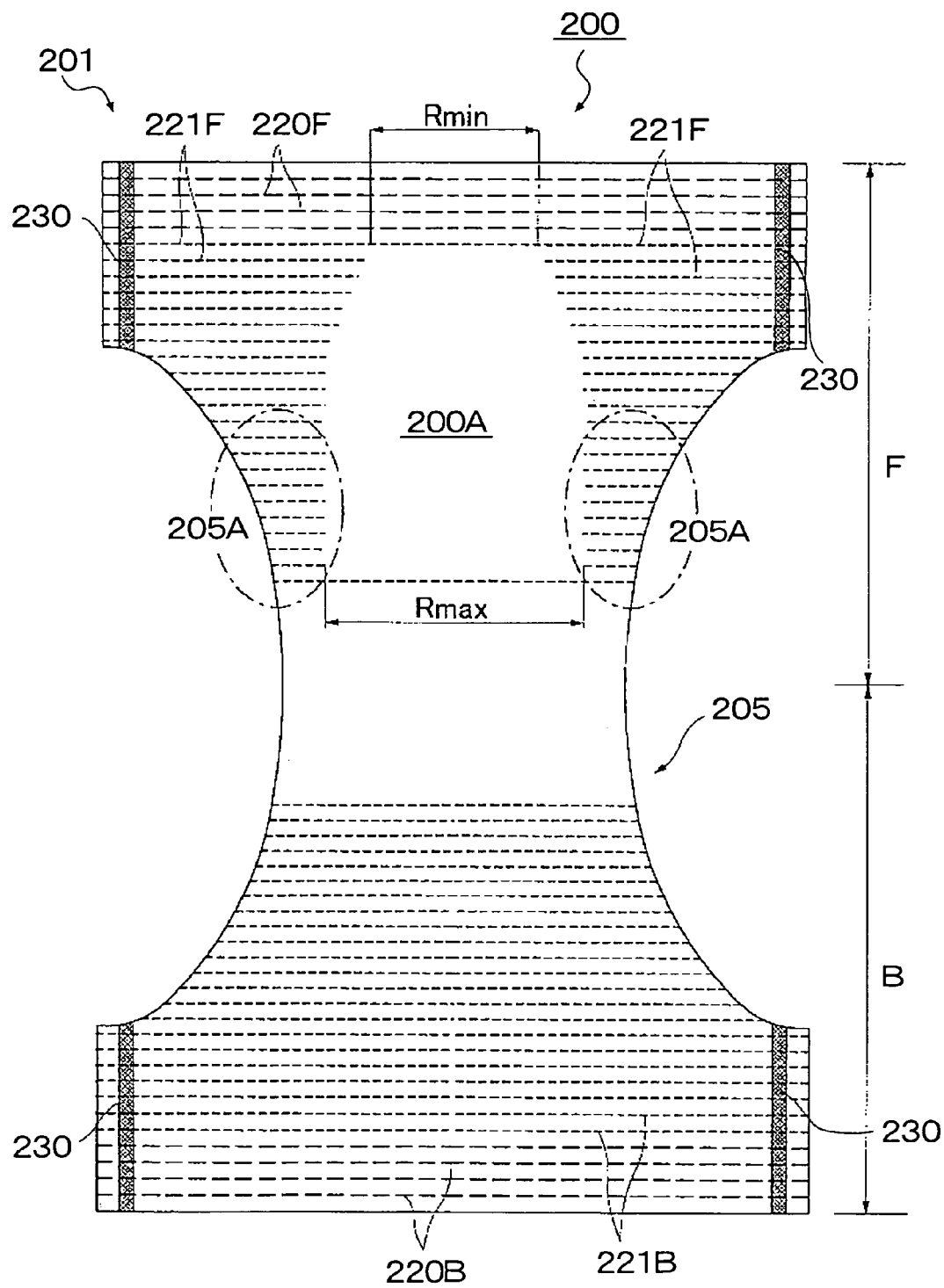
FIG. 7 is a front face side development plan view showing the disposable diaper in FIG. 6.

Thus, as is also found in FIG. 7 showing a diaper surface side, because the partial portion of the absorbent body in the portion from the one side joint portion 230 to the other side joint portion 230 at the front side F has been discontinuously formed, the underbelly portion elastic members 221F and 221F do not run on across the absorbent body 210 at the front side F and contraction force in the width direction against the absorbent body 210 is attenuated. As a result, prevented is the problem that the absorbent body rises up from the skin due to vertical wrinkles formed along the width direction by the action of elastic members across the absorbent body as is conventional and leakage occurs from the waist peripheral region.

A cut area 200A of the elastic member is a minimum width Rmin at the front side end portion, and the width of the cut area is successively enlarged as being close to the center side and becomes the same cut area width Rmax at the center side from a midpoint. By changing the cut area width R, it becomes possible to adjust the contraction force in conformity with a body shape of the wearer. For example, when the cut area 200A is formed as shown in the figure, it becomes possible to reduce the contraction force to a extent that no vertical wrinkle is formed at the underbelly portion, and it becomes possible to reduce rubber trace at leg opening root portions by relatively reducing the contraction force at groin peripheral area 205A and 205A portions.

On the other hand, since the hip portion elastic member 221B is continuously formed from the one side joint portion 230 to the other side joint portion 230 at the back side B as is usual, it is possible to enhance slip-off prevention and adhesiveness to the skin to the same extent as those described above. Since there becomes nearly no wrinkle in the discontinuous portion of the underbelly portion elastic members 221F and 221F at the front side F, adhesiveness with a pants worn thereon becomes good and the diaper becomes simple one with good looks. Besides, although not shown in the figure, the underbelly portion elastic member 221F and 221F of the invention can be also discontinuously formed at the whole portion of absorbent body 210 in the portion from the one side joint portion 230 to the other side joint portion 230 at the front side F, and in this case, the same action effects as the above can be obtained.

Since the other configurations and action effects are the same as those in the first embodiment, the description is omitted.

Third Embodiment

Figure 8:
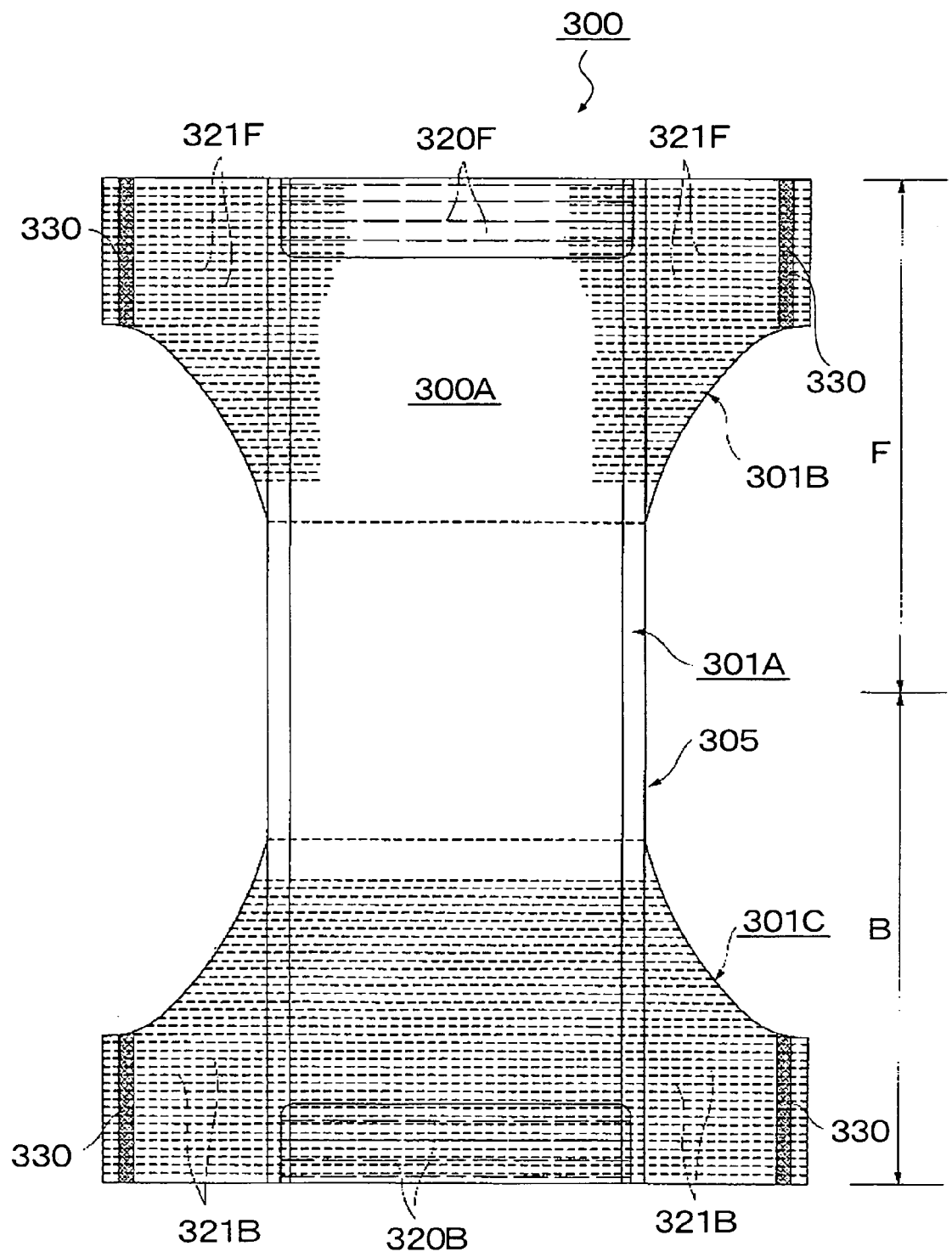
FIG. 8 is a development plan view showing the disposable diaper according to the third embodiment of the invention.

For the meantime, FIG. 8 shows the disposable diaper 300 in the third embodiment, which is made by laminating and fixing a rectangular body external sheet 301A of which width is slightly wider than that of an absorbent body 310 (not shown in the figure), a front side body periphery sheet 301B which forms the front side portion except leg peripheral portion 305, and a back side body periphery sheet 301C which forms the back side portion except the leg peripheral portion 305.

In the body external sheet 301A, a plurality of waist elastic members 320F and 320B are positioned and fixed under extension with intervals and in parallel with end edges at both end edges which composes the waist opening portion. A plurality of elastic members 321F and 321F which continue along the product width direction are attached each under extension at each side corresponding site of the front side body periphery sheet 301B, and the elastic members 321F and 321F at these side corresponding sites are mutually discontinuous.

On the other hand, at the back side body periphery sheet 301C, the elastic members 321B are positioned and fixed to continuously extend from one side joint portion to the other side joint portion. And, the portion continuing to the waist elastic members among these elastic members 321B forms a part of the waist elastic members of the invention functionally and conceptually.

In the above example, the underbelly portion elastic members are discontinuously formed and the hip portion elastic members are continuously formed, however, conversely it is possible that the underbelly portion elastic members are formed continuously from the one side joint portion to the other side joint portion and the hip portion elastic members are formed discontinuously at a portion of or whole absorbent body at the portion from the one side joint portion to the other side joint portion, or that both the underbelly portion elastic members and the hip portion elastic members are formed discontinuously at a portion of or whole absorbent body at the portion from the one side joint portion to the other side joint portion.

In the above example, the elastic sheets of the invention are used for providing the underbelly portion elastic members and the hip portion elastic member, however, the elastic sheets of the invention can be used for the other portions where elasticity is liked to be imparted (e.g., also for providing the waist elastic members or leg peripheral elastic members).

Forth Embodiment

In FIGS. 9 to 12, the pants-type disposable diaper 400 according to the forth embodiment of the invention is shown.

Figure 9:
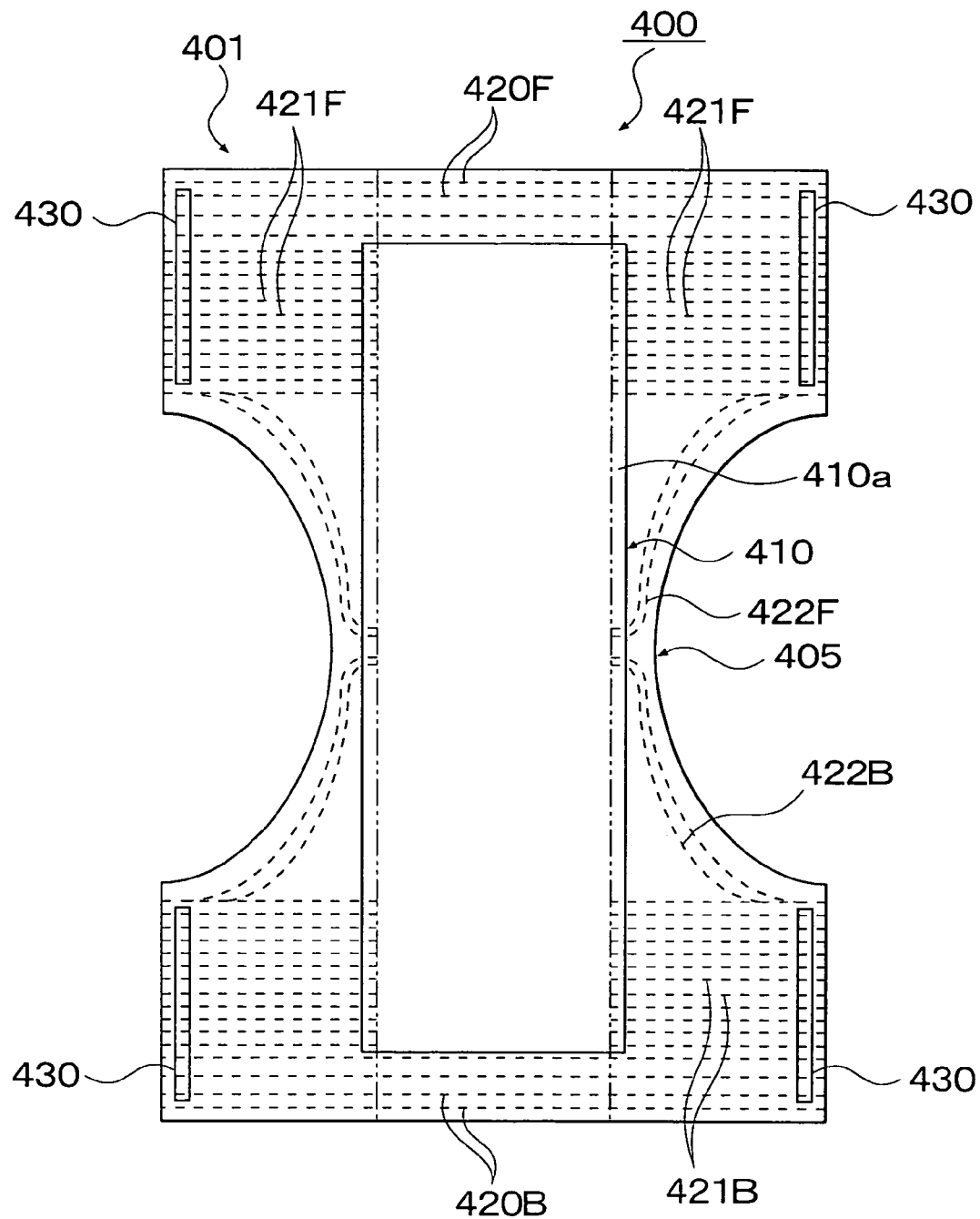
FIG. 9 is a development plan view showing the disposable diaper according to the forth embodiment of the invention.
Figure 10:
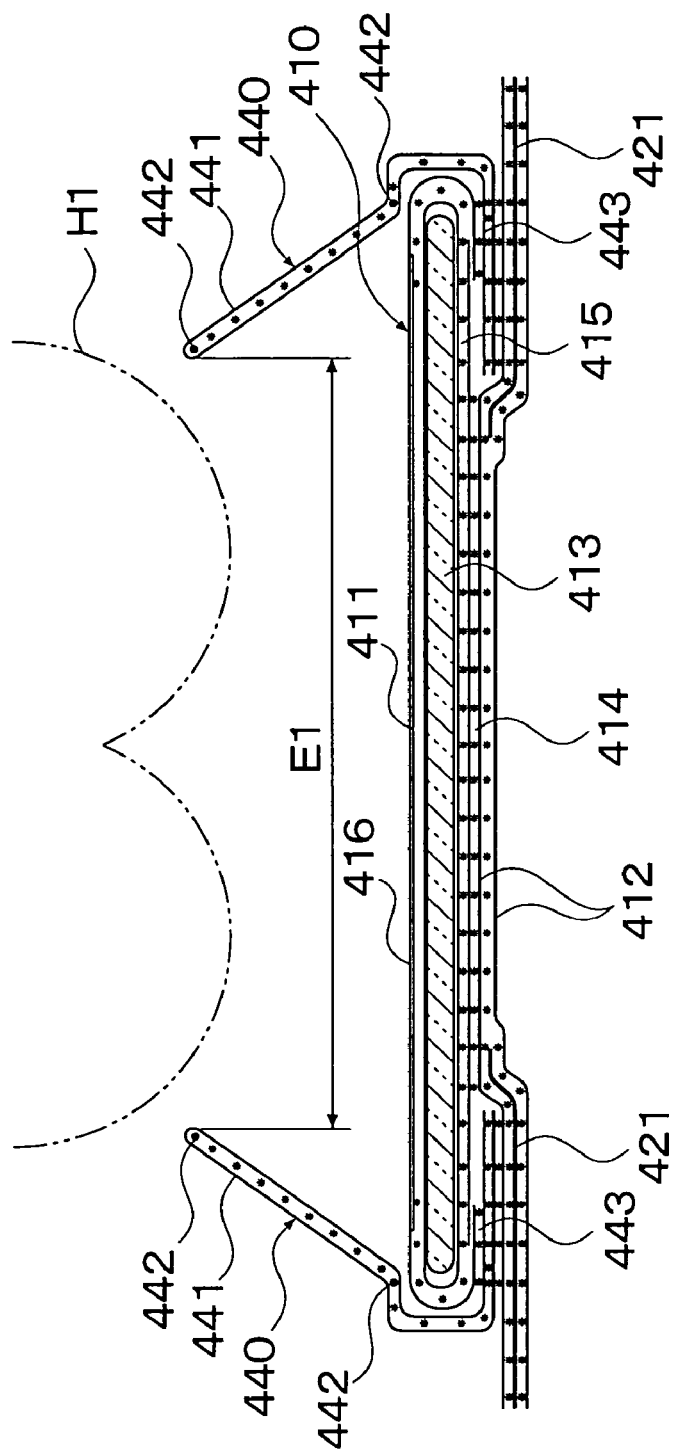
FIG. 10 is a main portion enlarged sectional view showing the disposable diaper in FIG. 9.

As shown in FIGS. 9 and 10, the pants-type disposable diaper 400 mainly comprises a flexible external sheet 401, and an absorbent body 410 which is fixed to an inner face of the external sheet 401 and extends in a longitudinal direction with making leg peripheral portions 405 as a center, as is the case with the pants-type disposable diapers 100 to 300 in the first and second embodiments.

As is also shown in FIG. 10, the absorbent body 410 has a rectangular liquid permeable top sheet 411 which is made up of non-woven fabric and the like and directly contacts with skin of the wearer, a rectangular absorbent body 413 having stiffness to some extent, a rectangular liquid impermeable waterproof film 414 which makes the round of the absorbent body 413 from a back side to a surface side and covers both side portions of the surface side in a forehead winding form and a liquid impermeable back sheet 412, and these respective elements are integrated by attaching with a hot melt adhesive (those represented by * in the figure are attached portions). As the absorbent body 413, preferred are those where fibrillated pulp is a major ingredient and high molecular absorbent polymer is combined, and the absorbent body is given as the form entangled in the crepe paper 415. As the waterproof film 414, polyethylene film and the like are used. When it is required to enhance an absorbent ability, it is desirable to make a liquid permeable second sheet 416 intervene between the liquid permeable top sheet 411 and the absorbent body 413 as shown in FIG. 10.

The above absorbent body 410 is glued and integrated to the back sheet 412 at nearly whole back face by a hot melt adhesive with leaving both side portions of the waterproof film 414 a little.

The external sheet 401 is made by laminating and fixing two breathable/water-repellent non-woven fabrics, and whole longitudinal direction of both side edge portions of the front and back sides is joined by means of ultrasonic sealing, hot melting or the like at a final stage of the process for manufacturing after overlaying the external sheet 401 and the absorbent body 410 (the joint portion has been made a sign 430).

To enhance the fitness of the body periphery at the front and back sides, a plurality of under waist portion elastic members 421F and 421B which extend in the width direction is arranged between the non-woven fabrics at the portion from the width direction end portion of the body periphery at least to an outer side edge 410a of the absorbent body 413, at least such that the expansion and contraction of the under waist portion elastic members 421F and 421B do not contract the absorbent body 410 in the width direction. These under waist portion elastic members 421F and 421B are made up of rubber threads and the like, and the interval and number are appropriately determined. For example, it is preferred that the interval is from about 4 to 6 mm and the number is from about 5 to 7. Besides, it is desirable the waist elastic members 420F and 420B are provided at 50% or more in each width direction at flap portions with no absorbent body 410 (i.e., waist portion) in terms of further improving the fitness of the body periphery.

At the leg peripheries 405, leg peripheral portion elastic members 422F and 422B which run into at least the outer side edge 410a of the absorbent body 413 are arranged at the longitudinal direction approximately center at the leg peripheral portion 405 along an opening edge of the leg peripheral portion 405, such that at least the leg peripheral portion elastic members 422F and 422B do not contract the absorbent body 410 in the width direction. These leg peripheral portion elastic members 422F and 422B are made up of rubber threads and the like, and act to enhance the fitness of the leg peripheries.

Inner end portions of the under waist portion elastic members 421F and 421B and the leg peripheral portion elastic members 422F and 422B are located in the inward than the outer side edge 410a of the absorbent body 413. The waist elastic members 420F and 420B are formed not to overlap with the absorbent body 410. Besides, in some cases, the inner end portions of the under waist portion elastic members 421F and 421B and the leg peripheral portion elastic members 422F and 422B are located in the outer side than the outer side edge 410a of the absorbent body 410.

Three-dimensional gathers (rising cuffs) 410, 410 which rise from the body to the wearer side are formed respectively at the both side portion (specifically, right-and-left both side portion of the absorbent body 413) of the absorbent body 410 for the purpose of leakage prevention. The three-dimensional gather 410 comprises a rising sheet 441 which substantially continues in the width direction and elastic members 442, 442 made up of rubber threads which are arranged in the rising sheet 441. The rising sheet 441 is made up of a liquid impermeable or hydrophobic double sheets.

Figure 11:
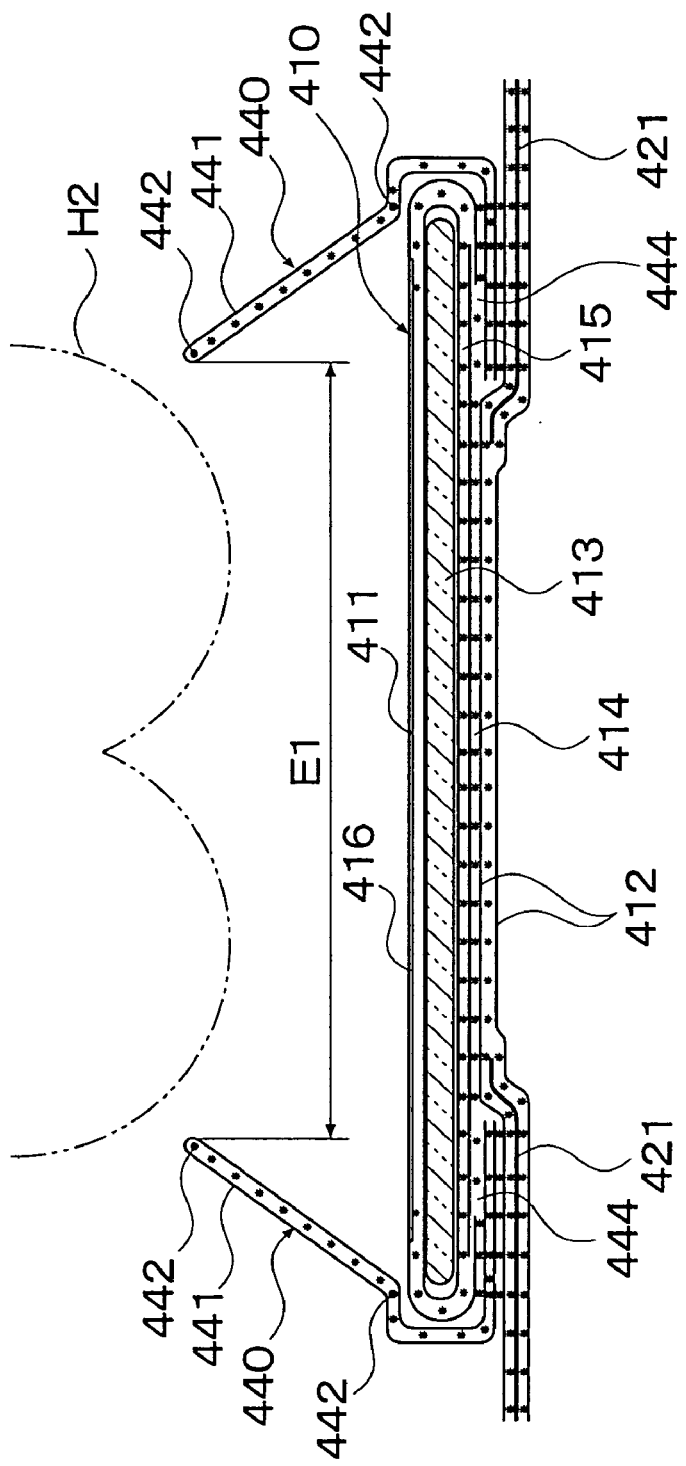
FIG. 11 is a main portion enlarged sectional view showing another example of the disposable diaper in FIG. 9.

A rising start point (rising end) 423 of the three-dimensional gather 440 is rendered a location tilting toward the inward from the outer side edge 410a at the absorbent body 413 lower portion, however, as shown in FIG. 10, there are some cases where it is rendered the location slightly tilting toward the inward from the outer side edge 410a at the absorbent body 413 whereas there are some cases where it is rendered the location greatly tilting toward the inward from the outer side edge 410a at the absorbent body 413 as shown in FIG. 11.

Figure 12:
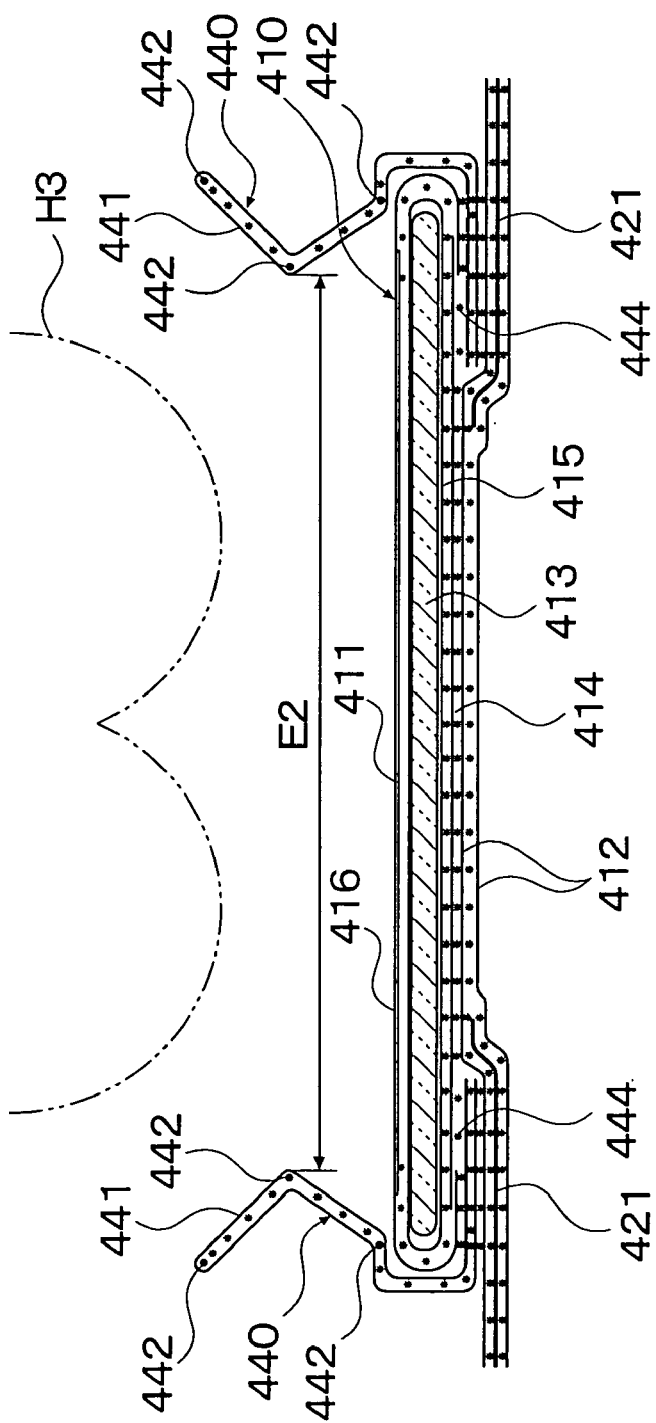
FIG. 12 is a main portion enlarged sectional view showing still another example of the disposable diaper in FIG. 9.

As shown in FIG. 12, there are also some cases where it is inflected from an intermediate site of a rising portion of the steric gather 440 to the outer side. Since a rising dimension from the absorbent body outer side edge 410a of the three-dimensional gather 440 is not so enlarged, the dimension E between the three-dimensional gathers 440 and 440 can be enlarged. Even if the wearing is not perfect, the diaper will not break into the crotch portion H. Besides, it is desirable that the dimension E of the three-dimensional gathers 440 and 440 is 50 mm or more in terms of preventing breaking into the crotch portion H.

In the diaper 400 configured as the above, the following action effects are obtained.

By elasticity of the under waist portion elastic members 421F and 421B and the leg peripheral portion elastic members 422F and 422B, the body periphery and the leg peripheries 405 fit well to the body periphery and the leg peripheries of the wearer. Since the under waist portion elastic members 421F and 421B and the leg peripheral portion elastic members 422F and 422B are not arranged at the portion corresponding to the absorbent body 410, there is no possibility that the absorbability is impaired due to the contraction of the absorbent body and there becomes no need to fear the liquid leakage.

Furthermore, by locating the inner end portions of the under waist portion elastic members 421F and 421B and the leg peripheral portion elastic members 422F and 422B in the inward from the outer side edge 410a of the absorbent body 413, the under waist portion elastic members 421F and 421B and the leg peripheral portion elastic members 422F and 422B can be arranged in the width direction as widely as possible in the range where the absorbability of the absorbent body 410 is not impaired. Therefore, the fitness of the wearer is further improved.

Fifth Embodiment

Figure 13:
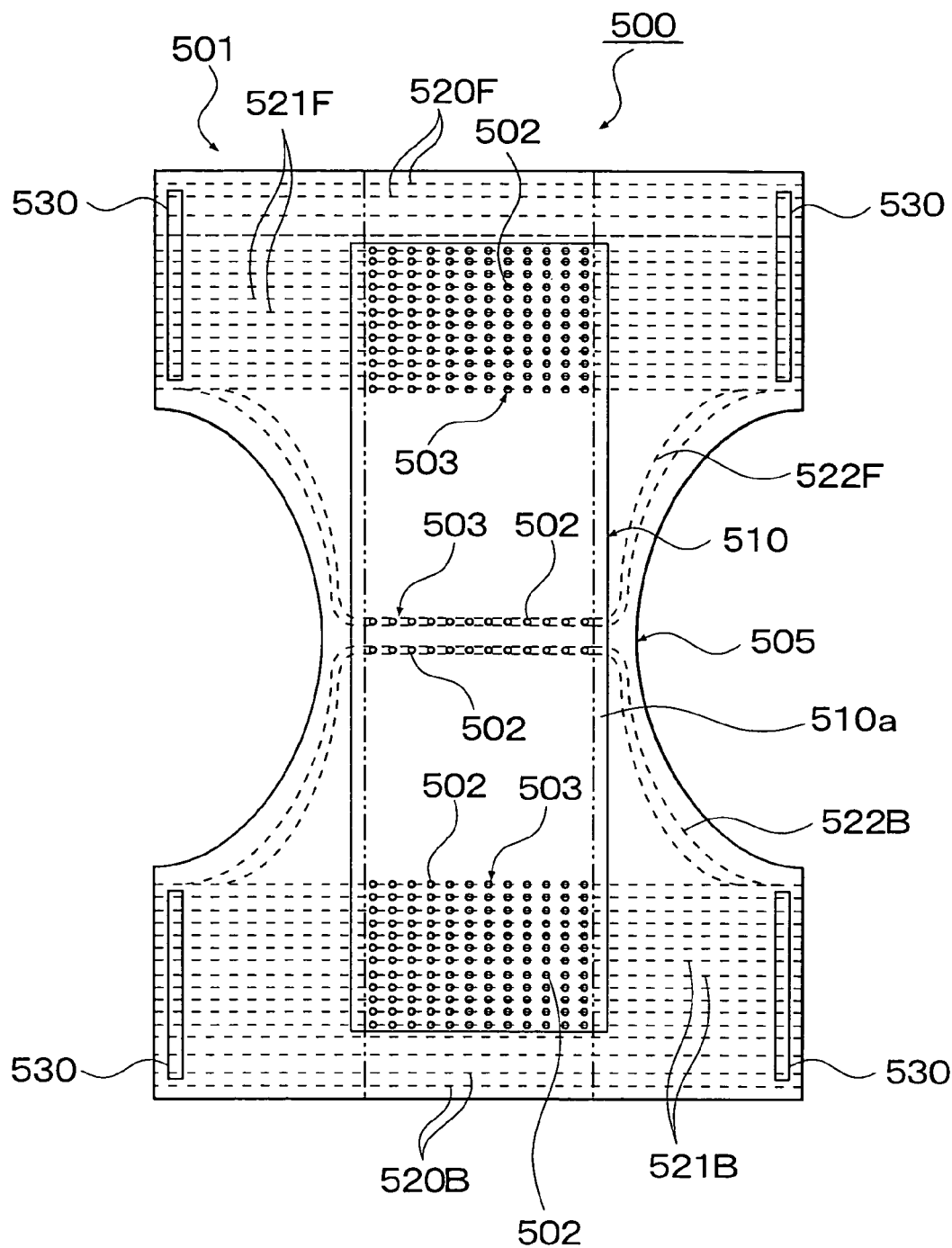
FIG. 13 is a development plan view showing the disposable diaper according to the fifth embodiment of the invention.
Figure 14:
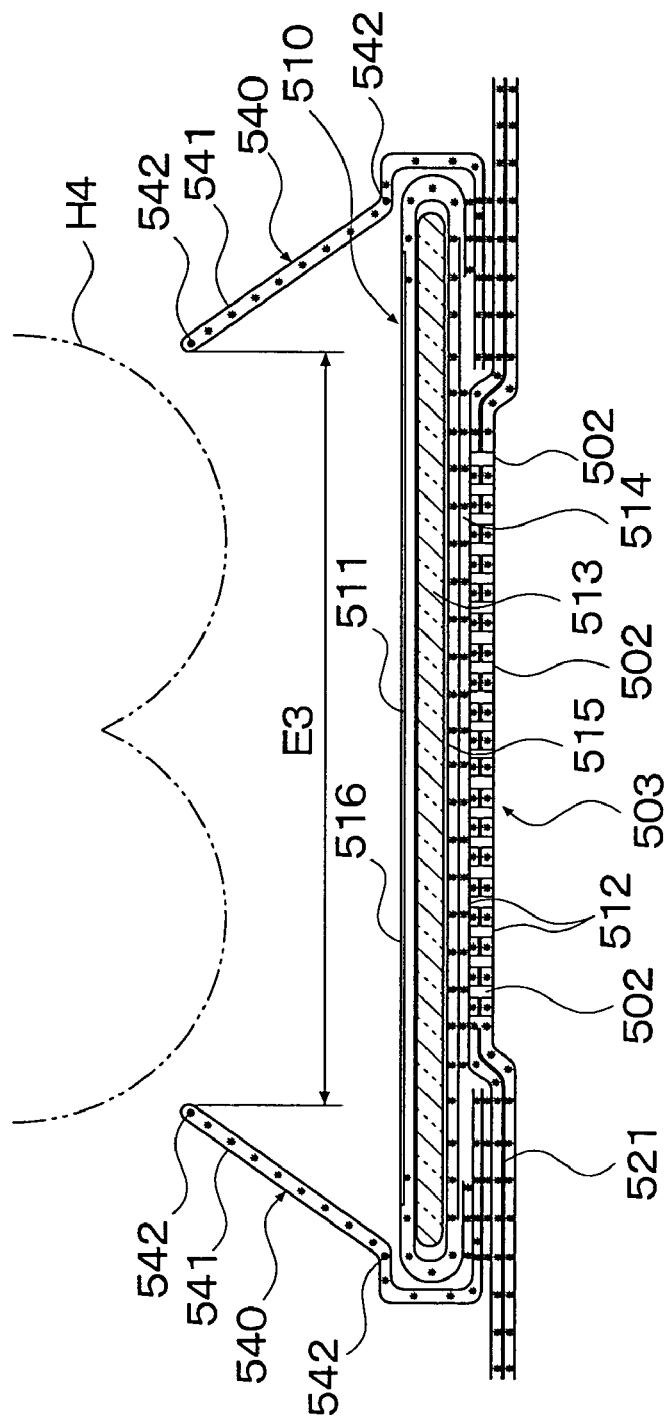
FIG. 14 is a main portion enlarged sectional view showing the disposable diaper in FIG. 13.

In FIGS. 13 and 14, the pants-type disposable diaper 500 according to the fifth embodiment of the invention is shown. Under waist portion elastic members and waist elastic members together make body peripheral region elastic members.

In this case, leg peripheral portion elastic members 522F and 522B linked in the width direction overstriding the absorbent body 510 are arranged in an approximately center in the longitudinal direction in the leg peripheral portion along the leg opening edge. A plurality of body peripheral region elastic members 520F, 520B, 521F and 521B which extend in the width direction are arranged at the body peripheral region. An elasticity lowering member 503 which lowers elasticity is given to those positioned corresponding to the absorbent body 510 among the body peripheral region elastic members 520F, 520B, 521F and 521B and the leg peripheral portion elastic members 522F and 522B. In this case, as the elasticity lowering member 503, employed is the member to cut the body peripheral region elastic members 520F, 520B, 521F and 521B and the leg peripheral portion elastic members 522F and 522B.

This allows the body peripheral region elastic members 520F, 520B, 521F and 521B and the leg peripheral portion elastic members 522F and 522B to fit the body peripheral region and the leg peripheral portions well to the body peripheral region and the leg peripheral portions of the wearer. The elasticity at the body peripheral region elastic members (under waist portion elastic members) 521F and 521B and the leg peripheral portion elastic members 522F and 522B at the portion corresponding to the absorbent body 510 is made lower by the cut member which is the elasticity lowering member 503. Therefore, there is no possibility that the absorbability is impaired due to contraction of the absorbent body 510 and there becomes no need to fear the liquid leakage. Furthermore, only cutting the body peripheral region elastic members 520F, 520B, 521F and 521B and the leg peripheral portion elastic members 522F and 522B can lower the elasticity of the body peripheral region elastic members 520F, 520B, 521F and 521B and the leg peripheral portion elastic members 522F and 522B, and thus the diaper can be manufactured with low cost. Since the other configurations and action effects are the same as those in the forth embodiment, the description is omitted.

Sixth Embodiment

Figure 15:
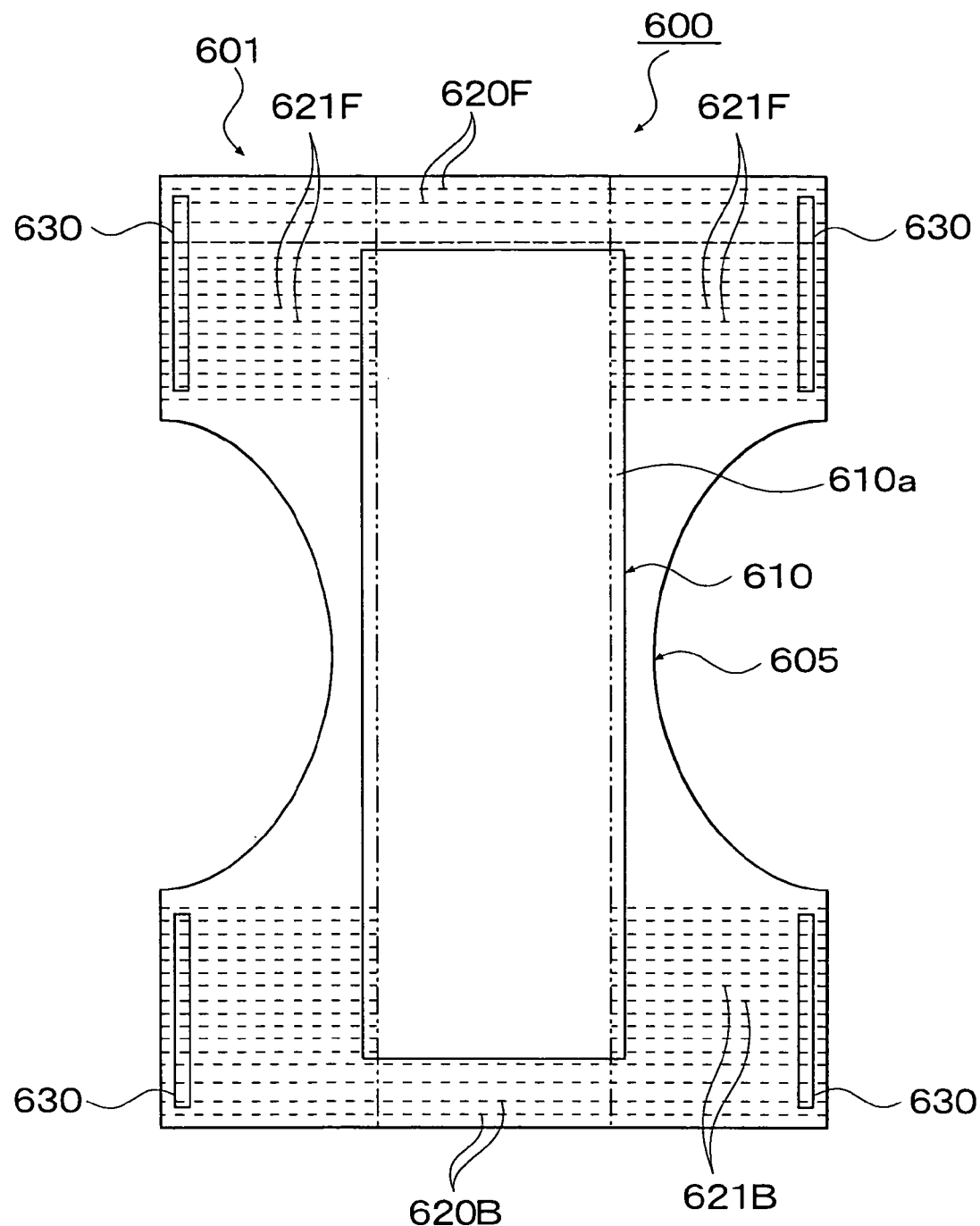
FIG. 15 is a development plan view showing the disposable diaper according to the sixth embodiment of the invention.

In FIG. 15, the pants-type disposable diaper 600 according to the sixth embodiment of the invention is shown.

In this case, a plurality of body peripheral region elastic members 620F, 620B, 621F and 621B which extend in the width direction are arranged only at the body peripheral region except the sites which do not correspond to both outer side edges 610a and 610a of the absorbent body 610, and no elastic member is arranged at the leg peripheral portion 605. In this case, inner end portions of the body peripheral region elastic members 621F and 621B (under waist portion elastic member) are located in the inward from the outer side edge 610a of the absorbent body 610. That is, the diaper 600 of the present embodiment has the form where no leg opening portion elastic member 123 is arranged in the diaper 100 of the first embodiment.

Because this arranges no elastic member at the leg peripheral portions 605, there is no possibility that the absorbability is impaired due to contraction of the absorbent body 610 and there becomes no need to fear the liquid leakage. Furthermore, because the elasticity of the body peripheral region elastic members 620F, 620B, 621F and 621B makes the body peripheral region fit well to the body peripheral region of the wearer, and no elastic member is arranged at the portion of the absorbent body 610 except the outer side edges 610a, there is no possibility that the absorbability is impaired due to contraction of the absorbent body 610 and there becomes no need to fear the liquid leakage.

In the present embodiment, since the inner end portions of the inner end portions of the body peripheral region elastic members 621F and 621B are located in the inward from the outer side edges 610a of the absorbent body 610, the elastic members 621F and 621B can be arranged in the width direction as widely as possible in the range where the absorbability of the absorbent body 610 is not impaired, and thus the fitness for the wearer is improved. Since the other configurations and action effects are the same as those in the forth embodiment, the description is omitted.

Seventh Embodiment

Figure 16:
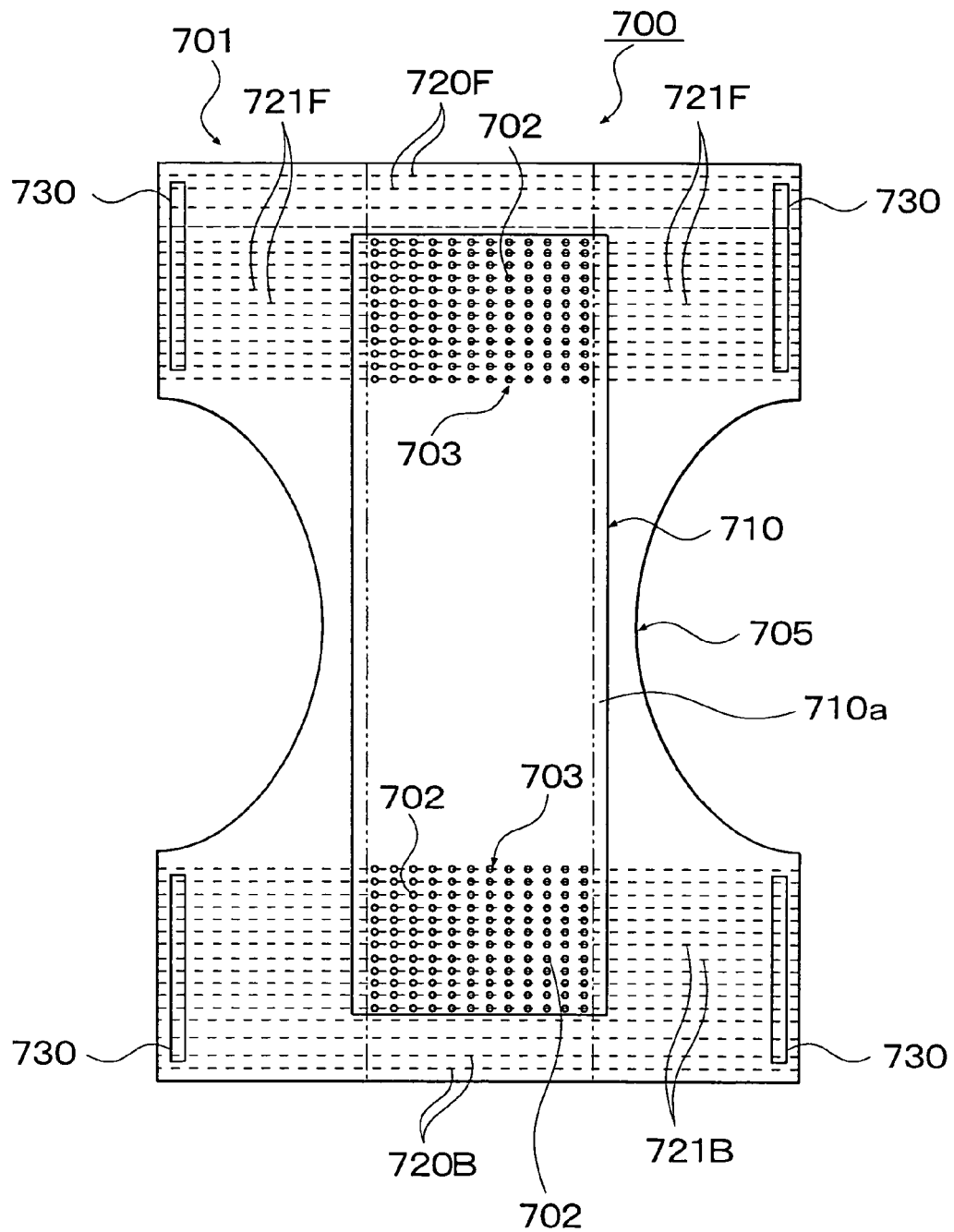
FIG. 16 is a development plan view showing the disposable diaper according to the seventh embodiment of the invention.

In FIG. 16, the pants-type disposable diaper 700 according to the seventh embodiment of the invention is shown.

In this case, a plurality of body peripheral region elastic members 720F, 720B, 721F and 721B which extend in the width direction are arranged only at the body peripheral region, and an elastic lowering member 703 which lowers the elasticity is given to those arranged corresponding to the absorbent body 710 among the body peripheral region elastic members 720F, 720B, 721F and 721B. The member to cut the body peripheral region elastic members 720F, 720B, 721F and 721B is employed as the elasticity lowering member 703 as with the fifth embodiment.

Since this arranges no elastic member at the leg peripheral portion 705, there is no possibility that the absorbability is impaired due to contraction of the absorbent body 710 and there becomes no need to fear the liquid leakage. Furthermore, because the elasticity of the body peripheral region elastic members 720F, 720B, 721F and 721B makes the body peripheral region fit well to the body peripheral region of the wearer, and the elastic lowering member 703 which lowers the elasticity is given to the body peripheral region elastic members (under waist portion elastic members) 721f and 721B at the portion corresponding to the absorbent body 710, there is no possibility that the absorbability is impaired due to contraction of the absorbent body 710 and there becomes no need to fear the liquid leakage.

In the present embodiment, because the member to cut the body peripheral region elastic members 720F, 720B, 721F and 721B is employed as the elasticity lowering member 703, only cutting the body peripheral region elastic members 720F, 720B, 721F and 721B can lower the elasticity of the body peripheral region elastic members 720F, 720B, 721F and 721B, and thus the diaper can be manufactured with low cost. Since the other configurations and action effects are the same as those in the forth and fifth embodiments, the description is omitted.

Eighth Embodiment

Figure 17:
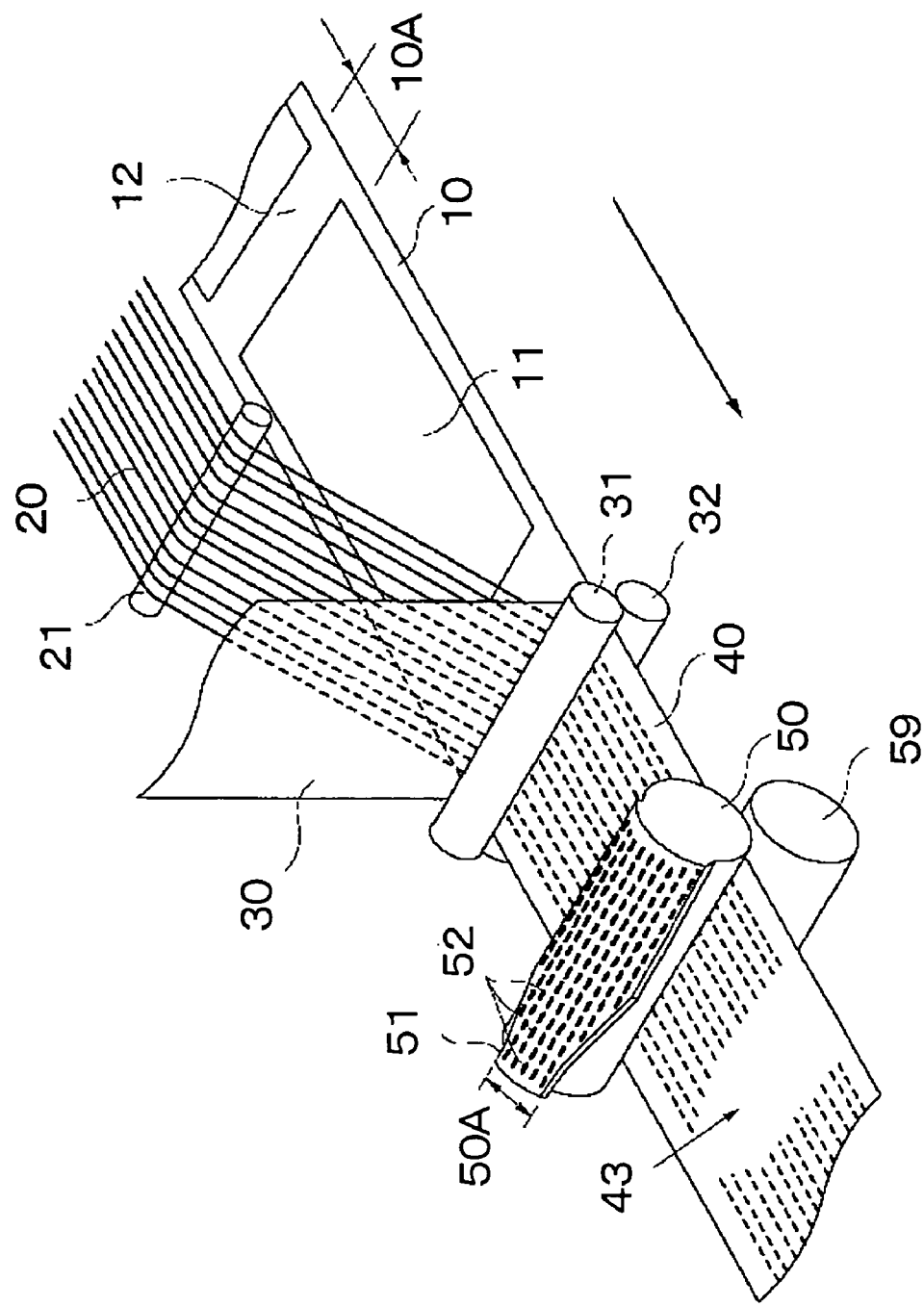
FIG. 17 is a perspective drawing showing a method for manufacturing elastic sheet according to the eighth embodiment of the invention.

In FIG. 17, there is shown a perspective illustration showing the method for manufacturing the elastic sheet according to the eighth embodiment of the invention. An arrow direction in the figure is a running direction of the sheet.

Figure 18:
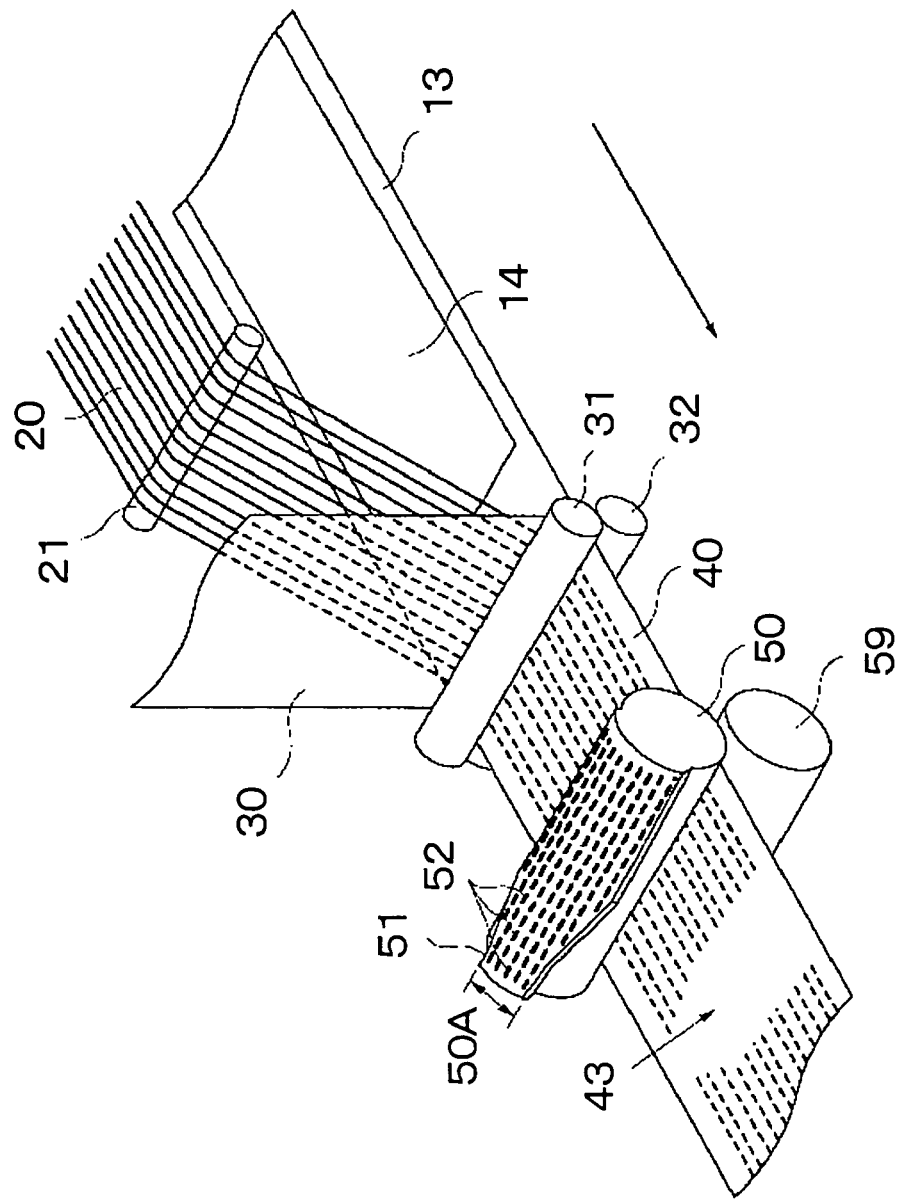
FIG. 18 is a perspective drawing showing another example of the method for manufacturing the elastic sheet according to the invention.

An obi-like lower sheet 10 with a predetermined width is running from a right side to a left side in the figure in the state where adhesive-applied portions 11 and non-applied portions 12 are provided by a hot melt adhesive coating machine which is not shown in the figure. In the invention, it is also possible to make the adhesive-applied portion 11 continue in a sheet longitudinal direction as shown in FIG. 18. It is preferred that the hot melt adhesive is coated by a spray coater, curtain coater, spiral coater and the like in terms of air permeability.

A plurality of elastic members 20 are reeled out from an elastic member roller (not shown in the figure), and are attached to the lower sheet 10 with being guided by a leading guide 21 in the state where a given tension is afforded by passing through a tension roller. At that time, the elastic member 20 is sandwiched with an upper sheet 30 and the lower sheet 10, they are bonded with pressure by passing between a press roller 31 and 32, and the upper sheet 30, the lower sheet 10 and the elastic member 20 are firmly glued together at the adhesive-applied portion 911.

This affords a laminate 40 (e.g., the back sheet in the invention) where the elastic member 20 is sandwiched with the upper and lower sheets 30 and 10).

This laminate 40 is inserted between an emboss heat roller (first roller) 50 comprising an emboss portion 51 and an opposed roller (second roller) 59, and only the elastic member is cut. The sign 43 in FIGS. 1 and 2 indicates a cut portion. A minimum width 50A of the emboss portion 51 is formed slightly shorter than a width 10A of the adhesive-non-applied portion 12. An interval of coating, a peripheral length of the emboss heat roller 50 and a running rate have been adjusted such that the emboss portion 51 abuts on the adhesive-non-applied portion 12.

Figure 19A:
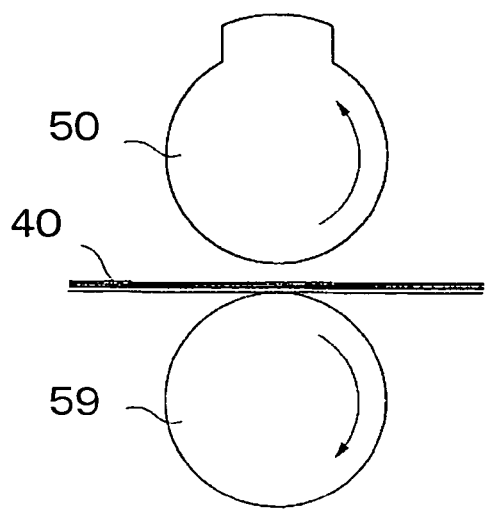
FIG. 19A is a front illustration showing an emboss heat roller and an opposed roller in FIG. 17 in a non-cutting state.
Figure 19B:
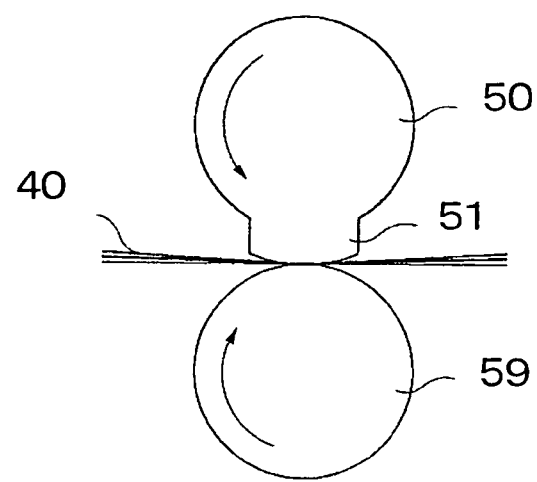
FIG. 19B is a front illustration showing an emboss heat roller and an opposed roller in FIG. 17 in a cutting state.

It is preferable that the opposed roller 59 has been separated from the emboss heat roller 50 to abut only on the emboss portion 51 of the emboss heat roller 50 as shown in FIG. 19. When the emboss part 51 comes down by rotation of both roller, it abuts on the opposed roller 59. Small convex portions 52 (convex portion of the invention) as exemplified in FIG. 20 have been further formed on the emboss part 51, and actually front faces of these convex portions 52 abut on the opposed roller 59. It is also preferable to provide fit concave portions corresponding to the convex portions 52 on the side of the opposed roller 59.

In the above emboss portion 51, as shown in the developed view of FIG. 20, one side (upper side in the figure) from an optional point in a roller axis direction is rendered a cut location variable portion 51A where cut lengths are successively extended by changing the cut locations of the elastic member 20 in a taper form, whereas the other side (lower side in the figure) is rendered a cut location identical portion 51B where the cut locations of the elastic member 20 are made identical. The convex portions 52, 52, . . . are provided throughout an upper face of the emboss portion 51 according to a predetermined disposition pattern. The disposition pattern is such that it is different at an intermediate rectangular portion (standard pattern portion) 55A which is surrounded by chain lines and at sideways trapezoidal both side portions (irregular pattern portions) 55B, 55B which is located at both side of the intermediate rectangular portion 55A.

Figure 21A:
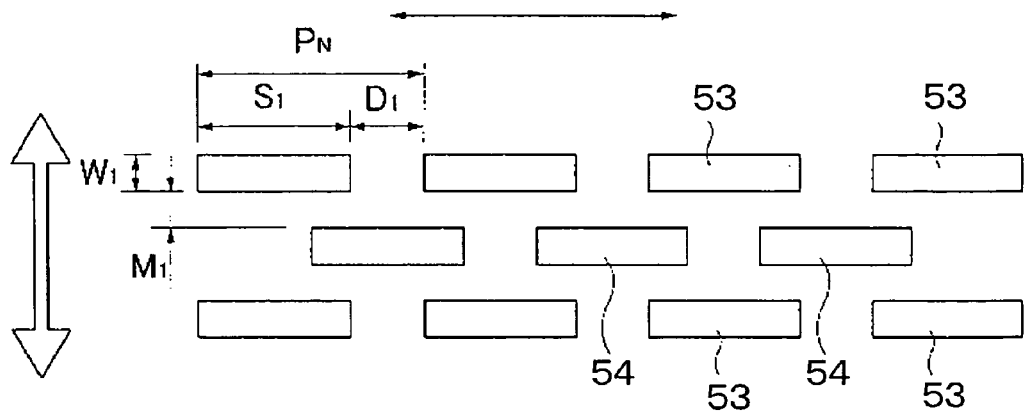
FIG. 21A is an illustration showing an example of an emboss pattern of linear convex portions which is a staggered lattice arrangement at an intermediate square portion in FIG. 20.
Figure 21B:
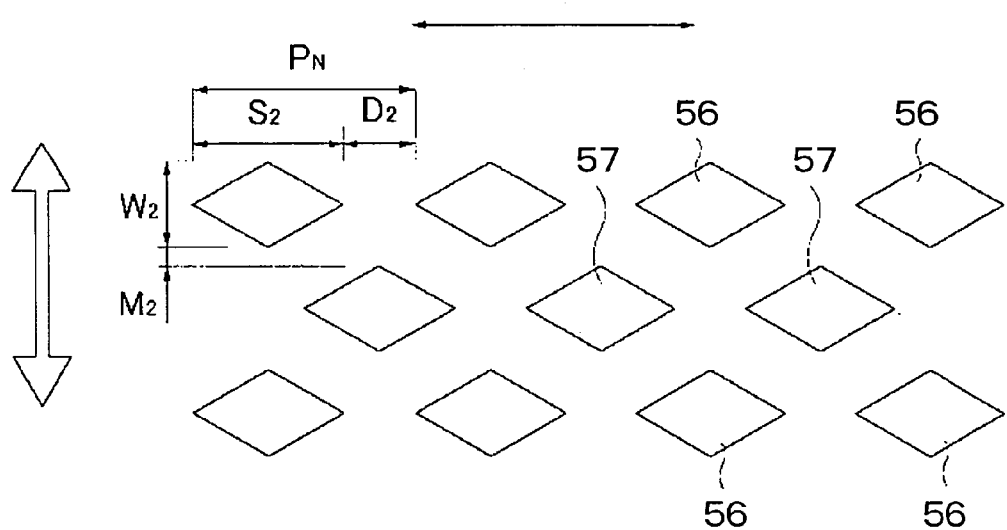
FIG. 21B is an illustration showing an example of an emboss pattern of lozenge convex portions which is a staggered lattice arrangement at an intermediate square portion in FIG. 20.

First, at the intermediate rectangular portion 55A, an arrangement pattern of the standard convex portions 52, 52, . . . is employed. Examples of specific and suitable emboss pattern thereof are shown in FIGS. 21A and 21B. FIG. 21A is the emboss pattern where a plurality of linear convex portions are arranged in a staggered pattern. That is formed by repeating the disposition pattern of a row of the convex portion group where the linear convex portions 53, 53, . . . with a length of S1 and a width of W1 are arranged in the axis direction of the emboss heat roller 50 (black arrow direction) with intervals of a distance D1 and a row of the convex portion 54, 54, . . . group with the same length S1 and width W1 as the convex portion 53 wherein the convex portions 54 are arranged in a peripheral face direction (open arrow direction) of the emboss heat roller 50 with intervals of a distance M1 after setting a pitch of the roller axis direction such that the convex portion 54 is present at the location capable of certainly being cut depending on the intervals of the elastic members, i.e., the location of the elastic members. In this case, the disposition pitch PN (become the standard pitch described below) in the roller axis direction of the convex portions 53, . . . 54, . . . is S1+D1. The number of the convex portions in a row could be appropriately set up by the number of the elastic members to be cut. The row number of the convex portion groups can be appropriately set up depending on the length B1 of the adhesive non-applied portion 12.

FIG. 21B is the pattern where lozenge convex portions are arranged in the staggered. That is formed by repeating the disposition pattern of a row of the convex portion group where the lozenge convex portions 56, 56, . . . with a long axis of S2 and a short axis of W2 are arranged in the axis direction of the emboss heat roller 50 (black arrow direction) with intervals of a distance D2 and a row of the convex portion 57, 57, . . . group with the same lozenge shape as the convex portion 56 wherein the convex portions 57 are arranged in a peripheral face direction (open arrow direction) of the emboss heat roller 50 with intervals of a distance M2 after setting a pitch of the roller axis direction such that the convex portion 57 is present at the location capable of certainly being cut depending on the intervals of the elastic members, i.e., the location of the elastic members. In this case, the disposition pitch PN (become the standard pitch described below) in the roller axis direction of the lozenge shaped convex portions is S2+D2. In this pattern, it is also needless to say that the number of the convex portions in a row and the row number of the convex portions can be appropriately set up depending on the number of the elastic members to be cut and the length B1 of the adhesive non-applied portion, respectively. An optional polygonal shape may be applied in place of the lozenge shaped convex portion.

The length S1 of the linear convex portion and the long axis S2 of the lozenge shaped convex portion are preferably in the range of 1 to 25 mm, and more preferably from 5 to 25 mm. It is preferred that S1 has the same length as the separate distance from the adjacent convex portion D1, or S1 is longer than D1. Due to the staggered disposition, it becomes possible to certainly cut the elastic member located between the convex portions 53 at the convex portion 54. Similarly in D2 and S2 in the case of the lozenge shaped convex portion 56, it is preferable to make $D2 \leq S2$. When the length S1 of the linear convex portion and the long axis S2 of the lozenge shaped convex portion is shorter than 1 mm, there is a possibility that the elastic member can not be cut in some cases, whereas when it is longer than 25 mm, there is a possibility to have a unpleasant feel because an area of a sealing portion becomes too large. Therefore, the range of the separate distance D1 and D2 is also preferably from 1 to 25 mm, and D1 is more preferably from 3 to 25 mm. In the case where the convex portion is the lozenge shape, when the convex portions adjacent in the roller peripheral face direction is only slightly overlapped one another in view of an elastic member annexing direction, there is a possibility that the elastic members escape from the sealing portion and can not be cut, and thus D2 is more preferably from 3 to 10 mm.

It is preferred that the width W1 of the linear convex portion and the short axis W2 of the lozenge shaped convex portion are from 0.5 to 15 mm. When the width W1 of the linear convex portion and the short axis W2 of the lozenge shaped convex portion are shorter than 0.5 mm, there is a possibility that the cut of elastic member can not be carried out, whereas when they are thicker than 15 mm, there is a possibility to have a unpleasant feel because an area of the sealing portion becomes too large. Especially for the short axis W2 of the lozenge shaped convex portion, it is preferred that a lower limit is 1 mm or more.

The separate distance M1 or M2 between the convex portion rows is not especially limited, however, it is preferred that the M1 and M2 are both from 0.5 to 25 mm. The shape of the convex portion is not limited to the above linear and lozenge shapes, and a diagonal line, circular, triangle, star, other polygonal shapes and the like are applicable. It can be changed depending on each row of the convex portions.

Figure 22:
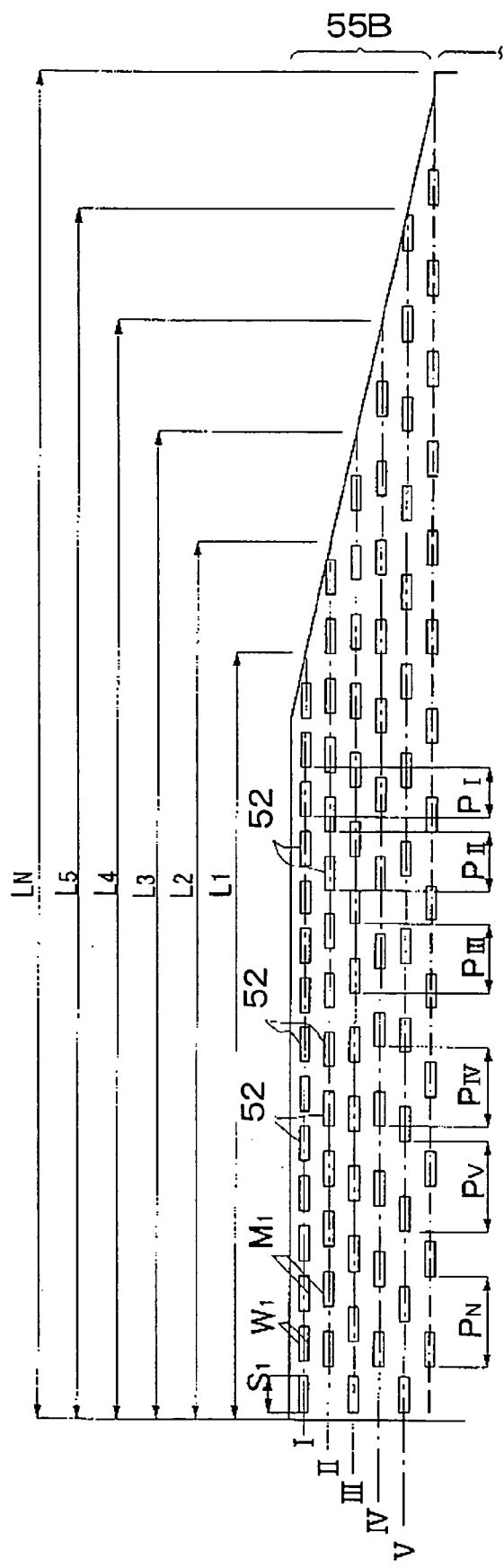
FIG. 22 is an illustration showing an example of an irregular emboss pattern at both side portions in FIG. 20.

On the other hand, in the both side portions 55B and 55B, an irregular emboss pattern is employed such that line pressure of the convex portion row 52, 52, . . . in the roller axis direction is nearly equivalent to that in the standard portion. As shown in FIGS. 20 and 22, in the both side portions 55B, the length S1 and width W1 of the linear convex portion 53, i.e., the dimension of the convex portion 52 is substantially identical, however, the disposition pitch Pi in the roller axis direction (because the length is identical, it is actually the distance D1) is changed for every convex portion row. The convex portion shape shown in the figure is the example of the linear convex portions 53, 54, . . . .

Specifically, for respective convex portion rows I to V in the both side portion 55B area, a formation section length in the roller axis direction of the convex portion row I is made L1, the formation section length in the roller axis direction of the convex portion row II is made L2, the formation section length in the roller axis direction of the convex portion row III is made L3, the formation section length in the roller axis direction of the convex portion row IV is made L4, and the formation section length in the roller axis direction of the convex portion row V is made L5. In respective convex portions I to V, in order to make total allongment, i.e., total number of the convex portion length S1, S1, . . . an identical value or approximate values, the approximate value of the value obtained by multiplying a ratio of the roller axis direction length L1 of the row to the roller axis direction length LN of the standard portion to the standard pitch PN is made the disposition pitch Pi in the roller axis direction of the convex portion 52 in respective convex portion rows I to V. Specifically, the disposition pitch of the convex portion I is made $PI \cong PN \times L1/LN$, the disposition pitch of the convex portion row II is made $PII \cong PN \times L2/LN$, the disposition pitch of the convex portion row III is made $PIII \cong PN \times L3/LN$, the disposition pitch of the convex portion row IV is made $PIV \cong PN \times L4/LN$, and the disposition pitch of the convex portion row V is made $PV \cong PN \times L5/LN$. A numerical value or an approximate value obtained from this formula is set up as the disposition pitch of each convex portion row. The disposition pitch obtained by the formula is theoretically the numerical value that can make the total allongment of the convex portion length S1, S1, . . . on each convex portion row identical or approximate. By disposing the convex portions 52, 52, . . . according to this numerical value, it becomes possible that the line pressure in the both side portions 55B is nearly equivalent to the line pressure in the standard portion, and it becomes possible that the cut locations of the elastic members are optionally changed without the occurrence of staving and slivering of the material sheet.

Figure 23:
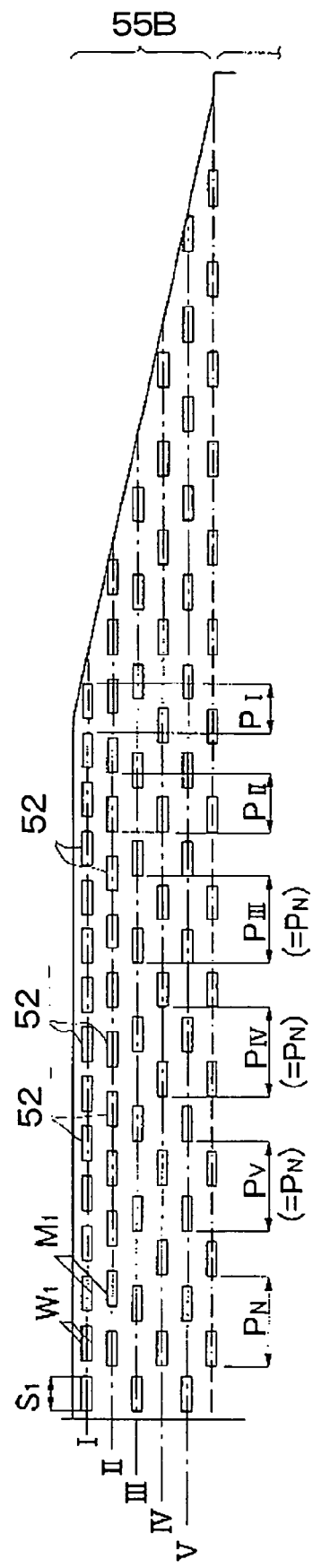
FIG. 23 is an illustration showing an example of an irregular emboss pattern at both side portions in FIG. 20.

It is not necessary to make the line pressure nearly uniform in all convex portion rows I to V for the disposition pattern of the convex portions 52 at the both side portions 55B, and the disposition pitch Pi in the roller axis direction may be changed only for the parts where staving and slivering occur due to excessively high line pressure. FIG. 23 is showing one example thereof. The disposition pitches PI and PII may be determined (e.g., by the above formulae) such that the line pressure is reduced to levels where staving and slivering do not occur only at the first and second convex portion rows from the side edge portion, and the standard pitches may be used for the other convex portion rows III, IV and V under the condition where staving and slivering do not occur.

In the above example, the plane shape of the emboss portion 51 was made into totally a cutting head home base shape having a cutting location variable portion 51A at an upper side and a cutting location identical portion 51B at a lower side, however, it can be made into optional shapes, such as a trapezoidal shape where a side edge is tilted from an upper end to a lower end, that is, a cutting shape where the upper end to the lower end is made into the cutting location variable portion. In any cases, in the present invention for the parts where the formation section length in the roller axis direction of the convex portion row is shorter than the standard portion, according to the procedure, the disposition pitch in the roller axis direction is changed and the line pressure is adjusted to become the predetermined value or less or nearly equivalent to that of the other convex portion row (standard portion).

Figure 24:
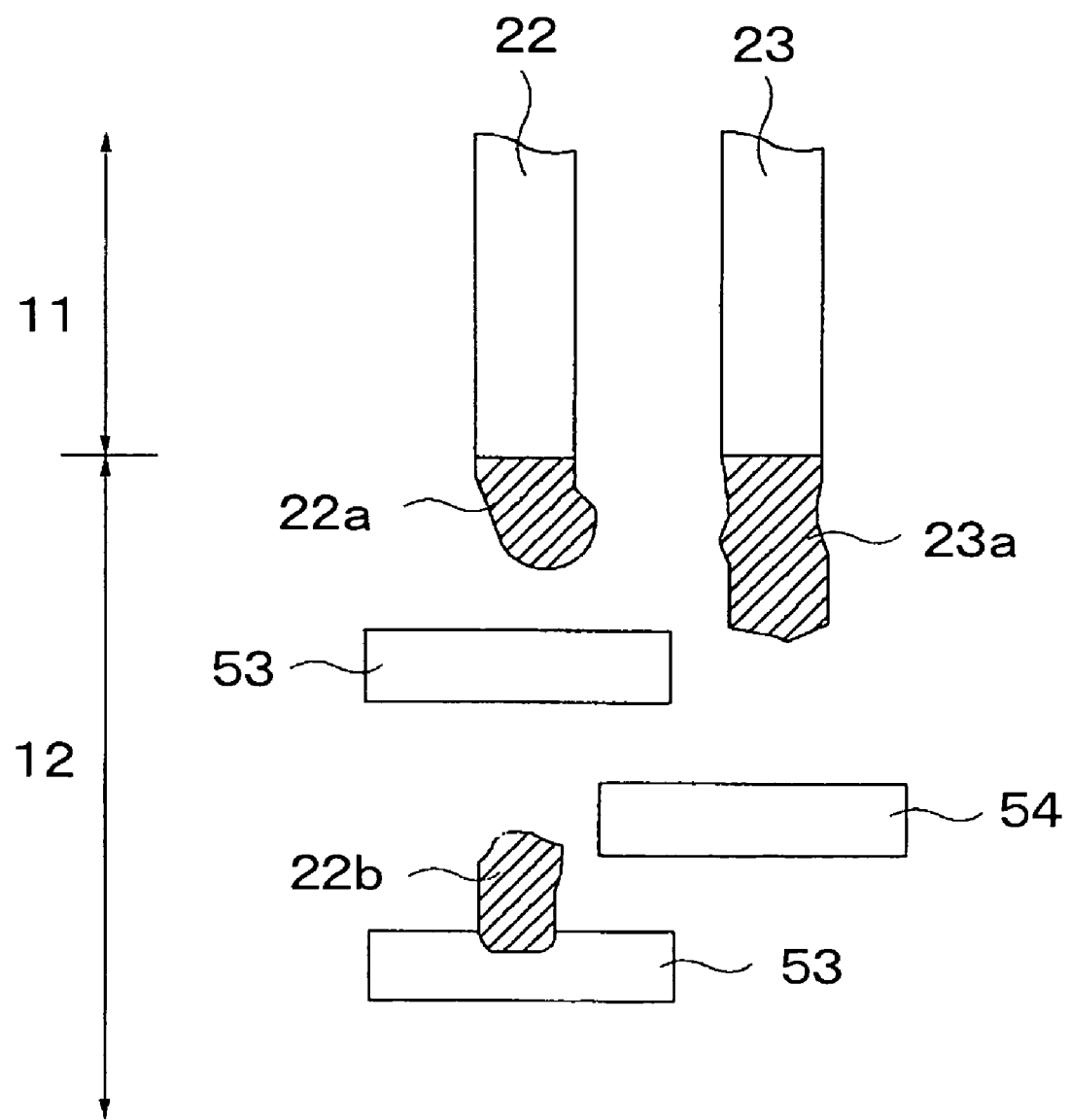
FIG. 24 is an enlarged plan view showing the cutting state of the elastic member in FIG. 17.

The state where the elastic member is cut by the method of the present invention is schematically shown in FIG. 24. In the figure, the sheet runs toward a bottom. The adhesive-applied portion is 11 and the adhesive non-applied portion is 12. The elastic member 22 at the left side is cut at the nearest sealing portion 53a (corresponding to the convex portion 53), an end portion thereof 22a is released from a stretched state, and expands and contracts toward the elastic member 22 which is joined and fixed to the sheet. When the remaining elastic member is complemented to an adjacent convex portion 53 before the cutting by the convex portion 53 is completed, the elastic member which has been between the convex portion 53 and the convex portion 53 contracts to the side of the sealing portion 53a at the cutting by the convex portion 53. When the cutting by the convex portion 53 is completed before the remaining elastic member is complemented to the convex portion 53, the elastic member 22b contracts toward the elastic member (not shown in the figure) present at the downstream adhesive-applied portion. The elastic member 23 at the right side is cut at the nearest sealing portion 54a (corresponding to the convex portion 54), and the end portion thereof 23a contracts.

Figure 25A:
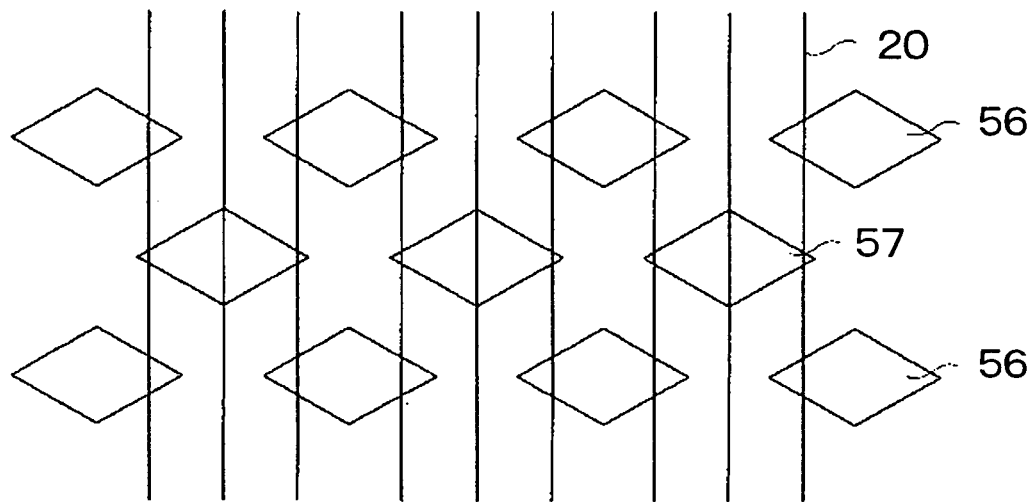
FIG. 25A is an illustration showing a cutting aspect of lozenge convex portions.
Figure 25B:
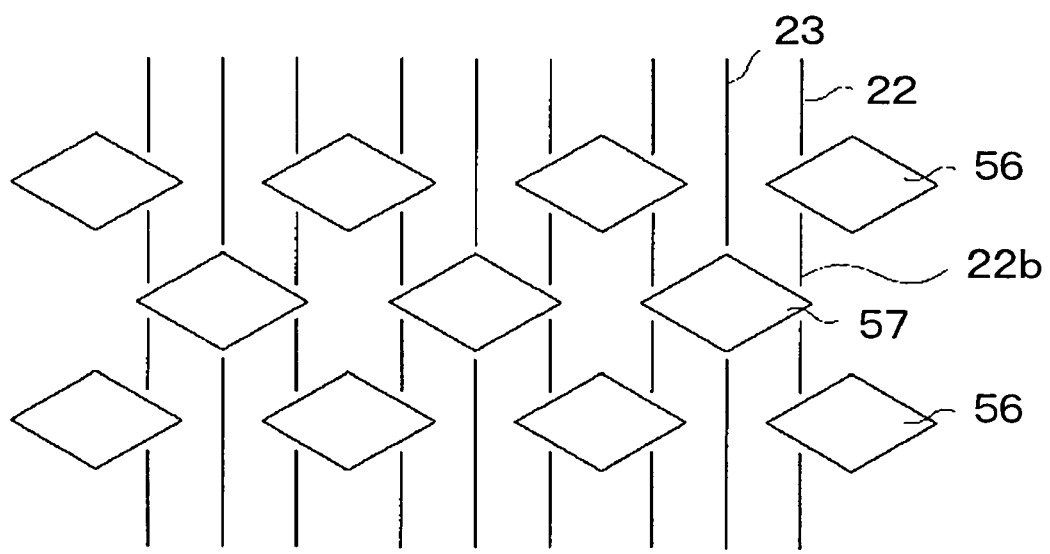
FIG. 25B is an illustration showing a cutting aspect of lozenge convex portions.

For the meantime, FIGS. 25A and 25B show the cutting aspects in the case of the lozenge shaped convex portions 56 mentioned above, and the cutting and sealing are carried out as is the case with the linear convex portions.

By the above configuration, the elastic members are cut, as well as a plurality of small sealing portion groups are formed at the non-elastic portion, and the upper and lower sheets are joined at the adhesive-applied portion 11. Since each sealing portion is separated and small, even when it is made into a thin film by heat sealing, it does not give discomfort to the wearer, relative to a long continuous line.

Ninth Embodiment

Figure 26A:
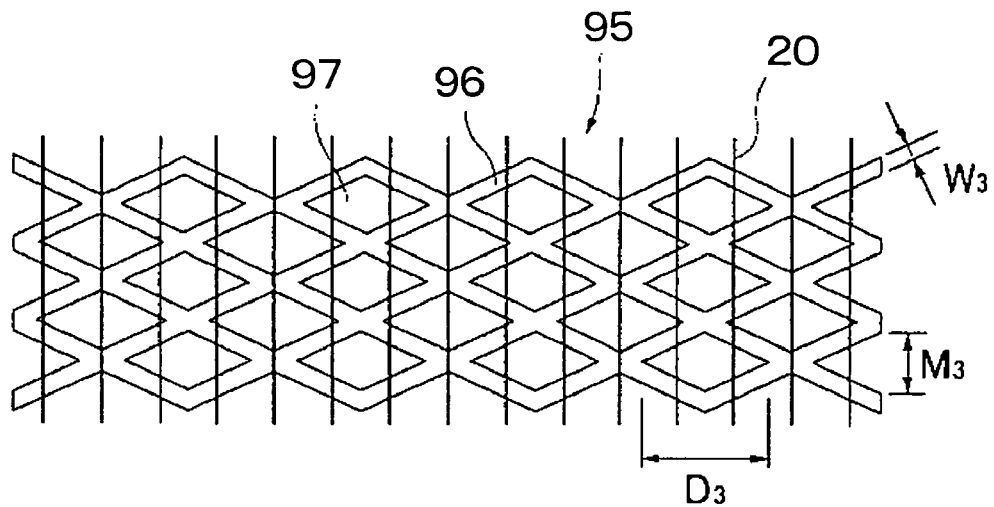
FIG. 26A is an illustration showing an example of a lattice emboss pattern in the method for manufacturing the elastic sheet according to the ninth embodiment of the invention.
Figure 26B:
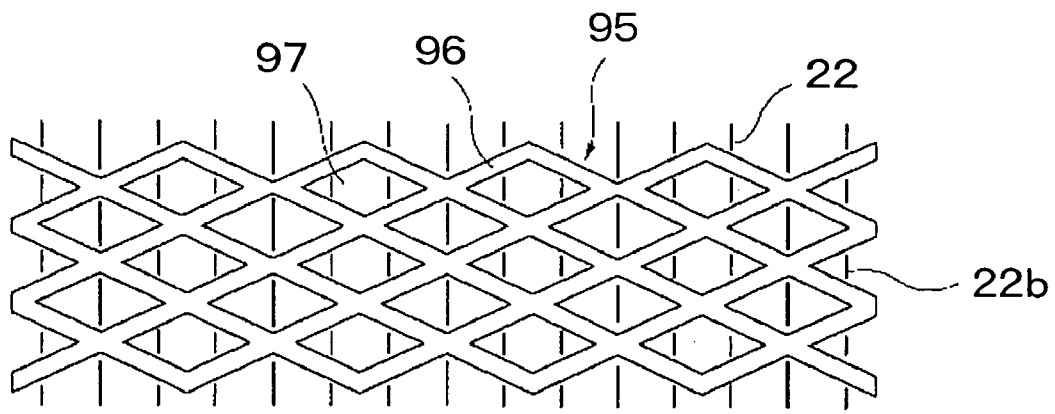
FIG. 26B is an illustration showing an example of a lattice emboss pattern in the method for manufacturing the elastic sheet according to the ninth embodiment of the invention.

In place of the emboss heat roller having the separately disposed convex portions in the above eighth embodiment, it is proposed in FIGS. 26A and 26B to use the emboss heat roller having concave portion group with a length of 1 to 25 mm and a width of 0.5 to 15 mm and having lattice shaped convex portion 95 where the width of a came is from 0.5 to 5 mm as shown. The lattice shaped convex portion 95 is formed by crossing a plurality of the cames 96, 96, . . . in a curb pattern, and space 97 surrounded by the cames 96 becomes the concave portion (lattice). W3 is the width of the came and is preferably from 0.5 to 5 mm. When it is too thick, there is a possibility that tactile impression goes bad, and when it is thinner than 0.5 mm, it becomes like a cutting tool and there is a possibility that both the upper and lower sheets are entirely cut. The length of the lattice shaped concave portion is D3, preferably from 5 to 25 mm, and more preferably from 5 to 10 mm. The width of the lattice shaped concave portion is M3, preferably from 5 to 25 mm, and more preferably from 5 to 10 mm. Diagonal lattices have been shown in FIGS. 26A and 26B, however, the lattice may be foursquare or rectangle. In this embodiment, since sealed in the lattice pattern, the elastic members can be certainly cut. Since the portion corresponding to the lattice concave portion 97 are not sealed, the sheet is not broken. Additionally, since thin lattice shaped convex portions are present at a certain degree of an area portion and are in a mesh form, the elastic members could be cut at any of seal portions. When sealed with a single-edged blade, since all elastic members should be cut with a single-edged blade, it is required to seal strongly not to leave the elastic members which are not cut, and thus the sheet is also cut in some cases. However, in the above configuration, since the elastic member may be cut at the sealing portion, it is not required to seal strongly, and also since bonded with pressure, the sheet is not broken. Lattice shaped sealing portion becomes one where tactile impression to the wearer is soft, and its appearance is also beautiful.

Tenth Embodiment

In reference to FIGS. 27 to 31, the method for manufacturing an elastic sheet used for the diaper having the elasticity lowering member, i.e., the method for cutting elastic members is described in detail.

In the tenth embodiment, the process until the laminate 45 (e.g., back sheet 512 of the diaper 500 in FIGS. 13 and 14) is obtained by sandwiching the elastic member 25 with the upper and lower sheets 35 and 15 is as is the case with the eighth embodiment, and thus the detailed description is omitted.

The laminate 45 in this case is inserted between the first roller 60 where a plurality of cutting convex portions 61, 61, . . . are disposed with intervals and the second roller 65 having concave portions 66, 66, . . . (see FIG. 29) where the cutting convex portions 61, 61, . . . are inserted, and the elastic member 25 is cut and holes are formed on the laminate 45 by insetting the cutting convex portion cuts 61, 61, . . . into the laminate 45.

Figure 28A:
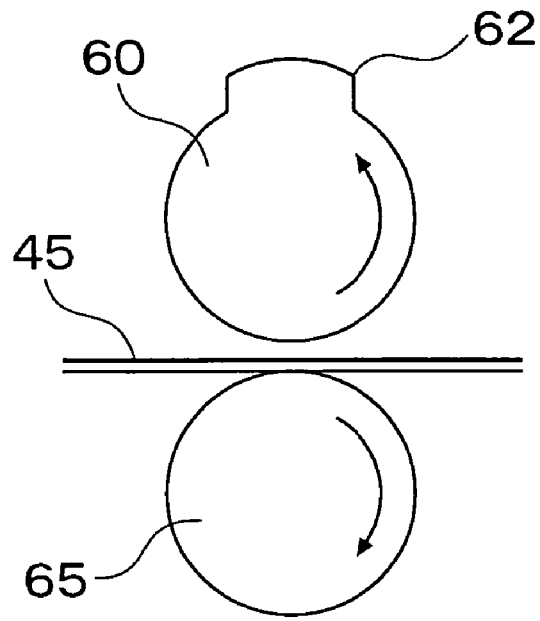
FIG. 28A is a front illustration showing the first roller and the second roller in FIG. 27 in a non-cutting state.
Figure 28B:
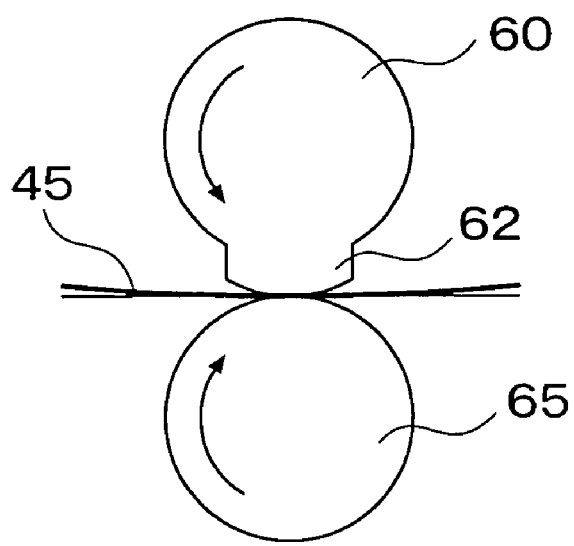
FIG. 28B is a front illustration showing the first roller and the second roller in FIG. 27 in a cutting state.
Figure 29:
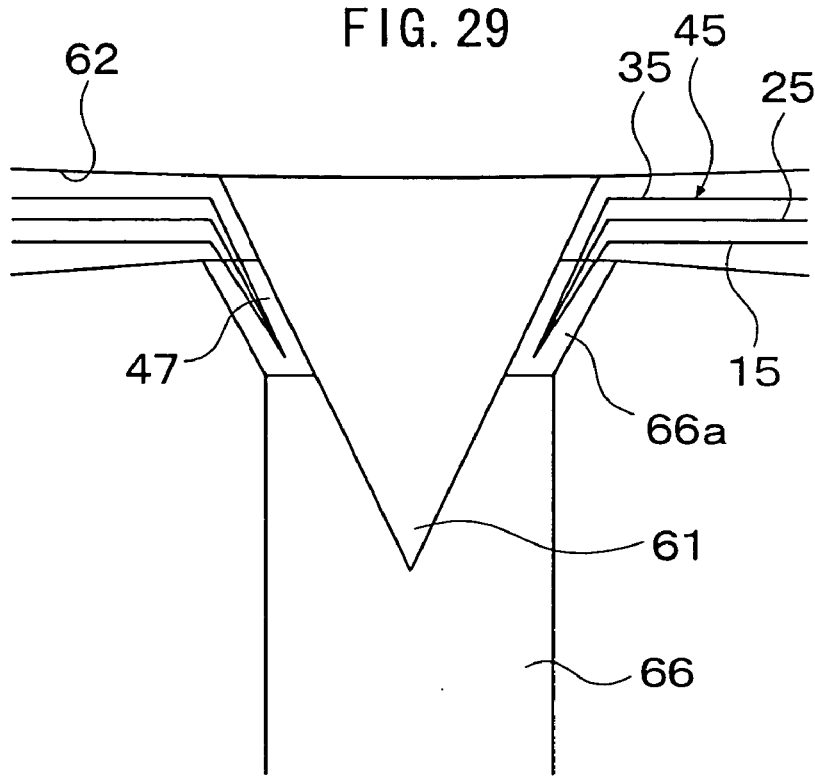
FIG. 29 is an illustration showing the state at cutting in FIG. 27.

In the present embodiment, in order to cut the elastic member 25 and form the holes 47, 47, . . . for the laminate 45 with appropriate intervals in a conveying direction of the laminate 45, the first roller 60 is configured to contact with an outer peripheral face of the second roller 65 only at a projecting face 62 which is provided at a portion of the peripheral direction thereof, and the cutting convex portions 61, 61, . . . are formed only at these projecting faces 62. Therefore, as shown in FIG. 28A, in the state where the projecting face 62 is not opposed to the second roller 65, the first and second rollers 60 and 65 are separated, and the cutting of the elastic member 25 and the formation of the holes 47, 47, . . . for the laminate 45 are not carried out, whereas as shown in FIG. 28B, when the projecting face 62 comes to the location in which the projecting face 62 opposes to the second roller 65 by the rotation of both rollers 60 and 65, the projecting face 62 of the first roller 60 abuts to the second roller 65, at that time, as shown in FIG. 29, the cutting convex portions 61, 61, . . . on the projecting face 62 is inset into the laminate 45, and the elastic members are cut as well as the holes 47, 47, . . . are formed on the laminate 45. In this case, when the concave portion base end portion 66a of the second roller 65 is formed in a taper shape where the diameter is expanded as being close to the opening side as shown in the figure, there is an advantage that the holes are formed more certainly and finely.

Figure 30:
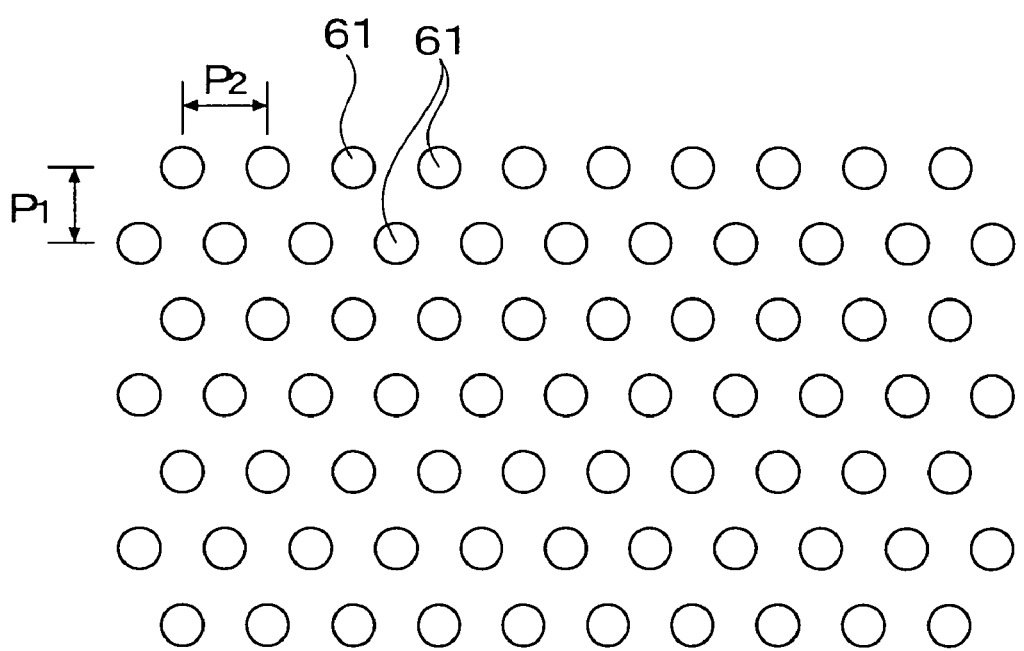
FIG. 30 is a plan view showing a disposing example of cut convex portions of the first roller in FIG. 27.

The cutting convex portions 61, 61, . . . can be disposed in a matrix pattern, however, to more certainly cut the elastic member 25, it is preferred that they are disposed in the staggered pattern as shown in FIG. 30. In this case, the pitches P1 and P2 in the axis direction and the peripheral direction of the first roller 60 are made equal to the desired hole pitches. The number of the cutting convex portions 61, 61, . . . in a row could be appropriately set up by the number of the elastic members 25 to be cut. The number of the roller axis direction rows of the cutting convex portions 61, 61, . . . can be appropriately set up depending on the length of the adhesive non-applied portion 17. Especially, it is preferred that the size and dimension of the cutting convex portions 61, 61, . . . are determined such that the cutting convex portions 61, 61, . . . of the peripheral direction front and back rows are overlapped to space between the cutting convex portions 61, 61, . . . of each the roller axis direction row in the peripheral direction. In that case, there is substantially no possibility that the elastic members 25 fails to be cut.

Figure 31:
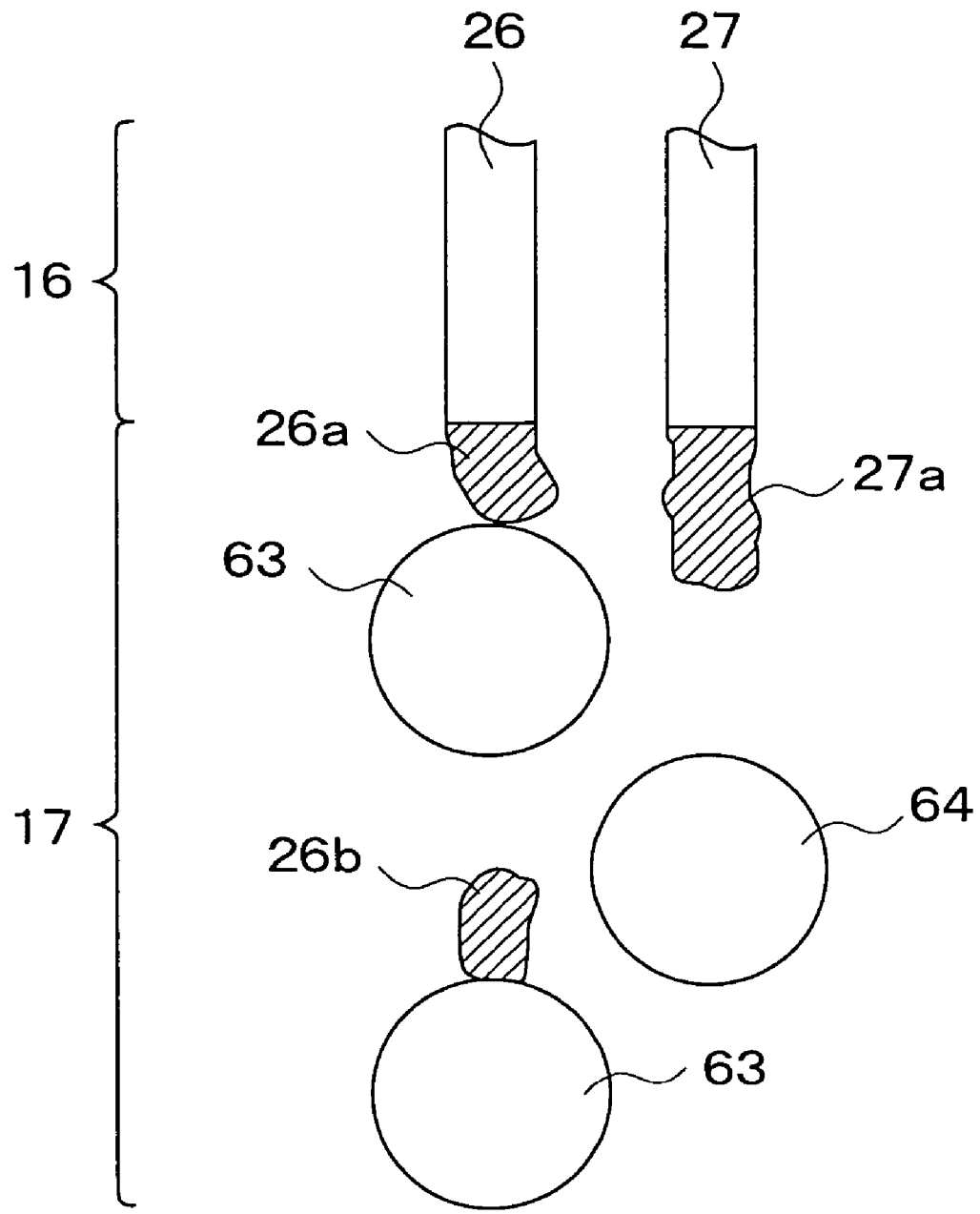
FIG. 31 is an enlarged plan view showing the cut state of the elastic member in FIG. 27.

More detailed cutting aspects in the case where the above staggered disposition is employed are shown in FIG. 31. In the figure, the sheet runs toward a bottom. The adhesive-applied portion is 16 and the adhesive non-applied portion is 17. The elastic member 26 at the left side is cut at the nearest sealing portion 63 (corresponding to the cutting convex portion 61), an end portion 26a thereof is released from a stretched state, and expands and contracts toward the elastic member 26 which is joined and fixed to the sheet. When the remaining elastic member 26 is complemented to the downstream sealing portion 63 (corresponding to the cutting convex portion 61 at a back side) before the cutting by upstream cutting convex portions 61 is completed, the elastic member 26b which has been between the both cutting convex portions 61 and 61 contracts to the side of the downstream sealing portion 63 at the cutting by the upstream cutting convex portions 61. When the cutting by the upstream cutting convex portions 61 is completed before the remaining elastic member 26 is complemented to the down stream cutting convex portions 61, the elastic member 26b contracts toward the elastic member (not shown in the figure) present at the further downstream adhesive-applied portion 16. The elastic member 27 at the right side is also cut at the nearest sealing portion 64, and the end portion 27a thereof contracts.

In the laminate 45 formed in this way, air permeability becomes good not only by certainly cutting the elastic member 25 by the inset of the cutting convex portions 61 but also by forming penetrating or fallen holes.

Other Modified Examples

In the method for manufacturing (or method for cutting) the elastic sheets in the above eighth to tenth embodiments, the modifications such as the following (A) to (H) are also possible.

(A) It is preferred that the first roller 50, 60 and the second roller 59, 65 comprise a heating member at least at one side and is configured to carry out a meltdown of the elastic members and sealing of the upper and lower sheets. A stick sheath heater may be provided, and another heating member such as a heating member by high frequency waves, far infrared radiation heater and oil heater may be combined in the vicinity thereof. However, in the present invention, it is possible to configure such that the cutting of elastic members is performed only by pressing. For example, in the above tenth embodiment, since the cutting convex portions 61 such as pins, cutting tools or the like are used, the cutting of the elastic members 25 can be carried out only by light pressing. In that case, it is possible to manufacture the soft laminate 45 of upper and lower sheets 35, 15 without heat sealing.

It is also possible to employ the configuration where the locations of the first roller 50, 60 and the second roller 59, 65 are reversed.

(B) It is preferred that any of the lower sheets 10, 15 and the upper sheets 30, 35 is heat bondable. Non-woven fabric, plastic film, knit, fabric, paper and the like can be used. As materials, it is possible to use the materials appropriately known in the art such as polypropylene, polyethylene, polyester, cellulose and rayon alone or in mixture of two or more.

(C) Respective sheets 10, 15, 30, and 35 may be multiple layer sheets where some sheets have been already laminated. In this case, it is required to provide the heat bondable sheet on an utmost face of the lower sheets 10, 15 or an undermost face of the upper sheets 30, 35.

(D) As elastic members, it is possible to use those which are the materials capable of being melt cut or being cut (e.g., thermoplastic polyurethane, various elastomers, rubbers and so on), and for example, filamentous, obi-like, sheet shape and netty. Not to cut the sheet, the elastic members of which melting point is lower than that of heat bondable materials of the upper and lower sheets are selected.

In the above eighth to tenth embodiments, since a plurality of the elastic members 20 and 25 are attached in parallel, it is possible to attach only one.

Figure 27:
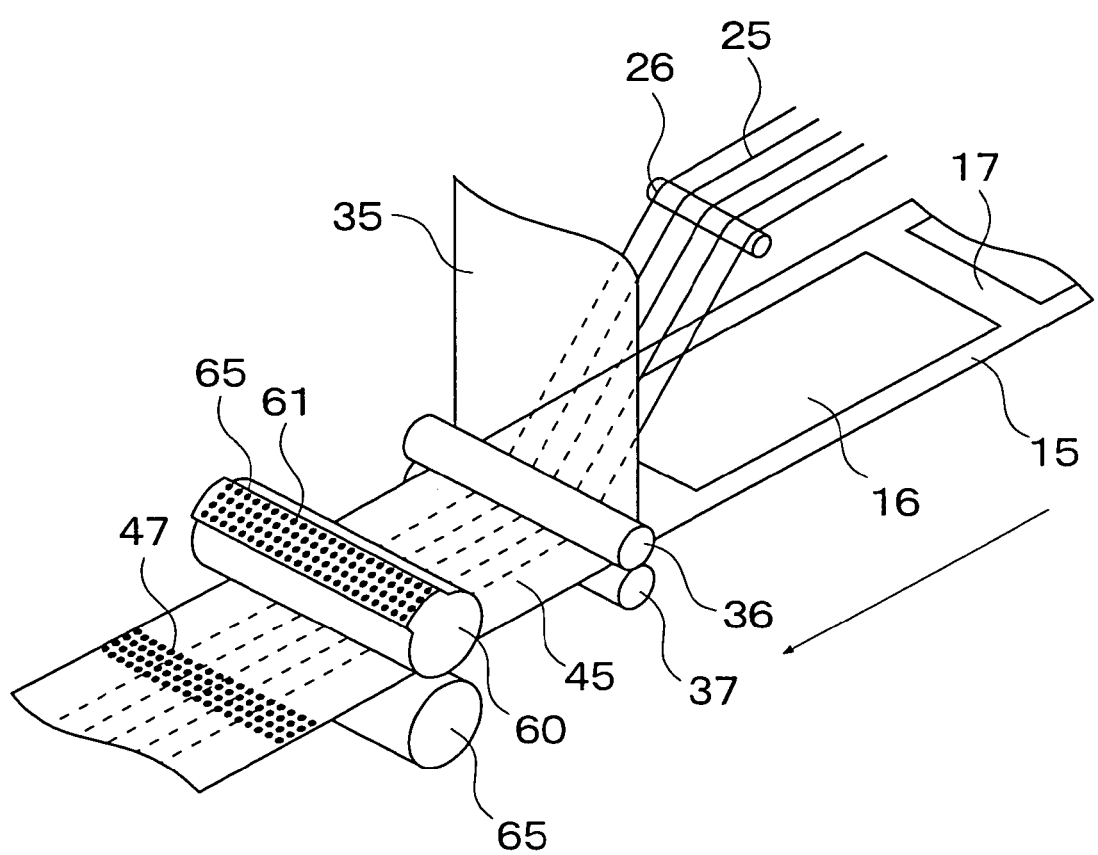
FIG. 27 is a perspective view showing the method for manufacturing the elastic sheet according to the tenth embodiment of the invention.

(E) In FIGS. 17 and 27, the examples where the elastic members are glued at a center in the width direction of the sheet were shown, however, they may be the configuration where the elastic members are glued at vicinity of the end portions of the sheet. The arranged portion of the emboss pattern could be changed in conformity with the attached location of the elastic members.

(F) The adhesive can be applied either one of or both of the upper and lower sheets. Further, the adhesive can be also coated discontinuously (see FIGS. 17 and 27) or continuously (see FIG. 18) along the longitudinal direction, or partially or entirely on the sheets and the like.

(G) As shown in FIGS. 32A to 32D, the cutting sites in the present invention may be the adhesive-applied portion X or the adhesive non-applied portion Y.

Figure 32A:
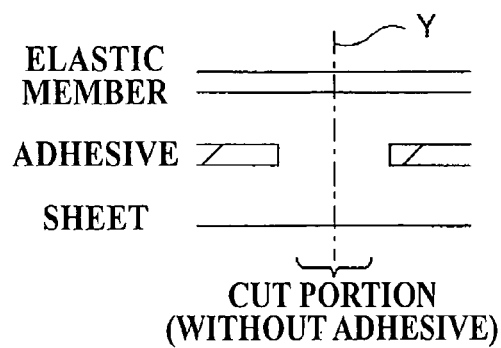
FIG. 32A is an illustration showing the first mode comprised in the method for manufacturing the elastic sheet according to the invention.
Figure 32B:
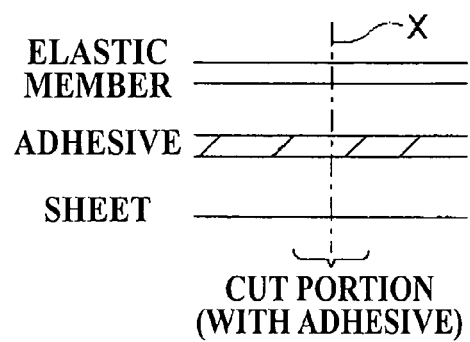
FIG. 32B is an illustration showing the second mode comprised in the method for manufacturing the elastic sheet according to the invention.
Figure 32C:
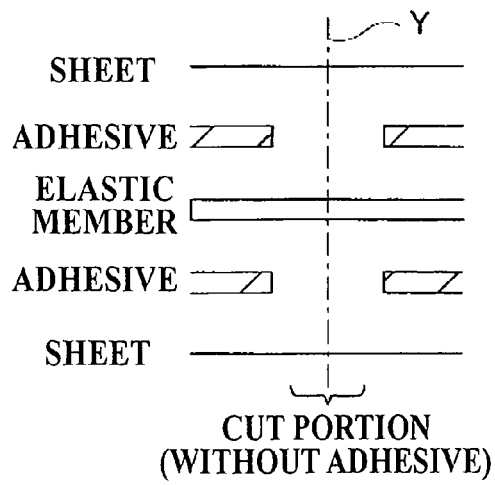
FIG. 32C is an illustration showing the third mode comprised in the method for manufacturing the elastic sheet according to the invention.
Figure 32D:
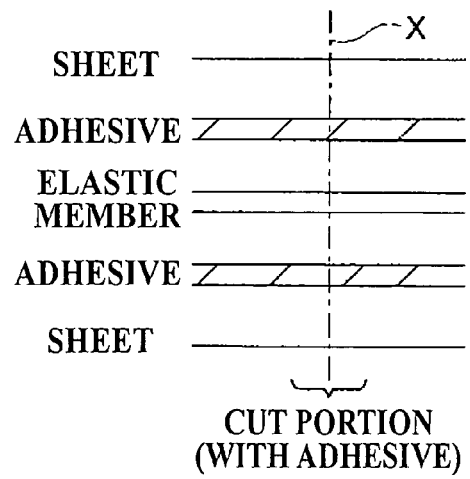
FIG. 32D is an illustration showing the forth mode comprised in the method for manufacturing the elastic sheet according to the invention.

(H) In the above examples, since the forms where the elastic members are sandwiched between a pair of the upper and lower sheets have been shown, as shown in FIGS. 32A and 32B, the elastic member cutting technique of the present invention can be also applied for the case where the elastic member is disposed and fixed on one sheet or multiple layer sheets.

The results of the eighth to tenth embodiments above are collectively shown as follows.

(1) Because the emboss heat roller (first roller) having the convex portion groups arranged in the staggered pattern or the emboss heat roller (first roller) having the convex portions in the lattice pattern is used, the elastic member is certainly cut at the heat sealing by any of the convex portions.

(2) In the case of the staggered disposition, because these convex portions are separated, the sheet which does not contact with the convex portions is not cut, and because the convex portions are small, the sheet in contact with the convex sheet is not cut. In the lattice disposition, because the thin lattice-shaped sealing portion is formed in the certain degree of area, tactile impression for the wearer becomes soft, an appearance thereof is beautiful, and the cutting of sheet is prevented.

(3) Because the cutting force does not act for the elastic member at the portion other than the convex portions, a portion in which the elastic member is cut and a portion in which the elastic member is not cut occur at the elastic member in the roller axis direction, leading-in due to cutting of the elastic member becomes partial, and the sheet becomes the good sheet in wearability with less feeling of foreign substance.

(4) Upon coating the hot melt adhesive, when the configuration where the non-applied portion and the applied portion are intermittently installed is employed, it is possible to continuously manufacture the elastic sheet which has the elastic portion and the non-elastic portion alternately, and that is preferable. In this case, there is also the advantage to join by sealing at the non-elastic portion.

(5) When the elastic sheet obtained by the present invention is made into a wearing article, the sealing area is small, and the sealing portions are separated in the staggered pattern or formed in the lattice pattern having space, therefore there are advantages that visual effects are beautiful and there is no possibility that discomfort such as pain is given to the wearer.

(6) At least when the convex portion rows where the formation section length of the convex portion row in the roller axis direction is uneven to the formation section length of the convex portion row in the standard portion are present, since the value or the approximate value thereof obtained by multiplying the ratio of the formation section length in the roller axis direction of the convex portion row to the formation section length in the roller axis direction of the standard portion convex portion row to the disposition interval of the convex portion row in the standard portion is set up as the disposition interval in the roller axis direction of the convex portions, Line pressure of respective convex portion rows becomes theoretically equal, and no staving and slivering occur in the sheet.

Eleventh Embodiment

Next, the example of the method for manufacturing the disposable diaper is shown to describe the method for utilizing the elastic sheet of the present invention.

Figure 33:
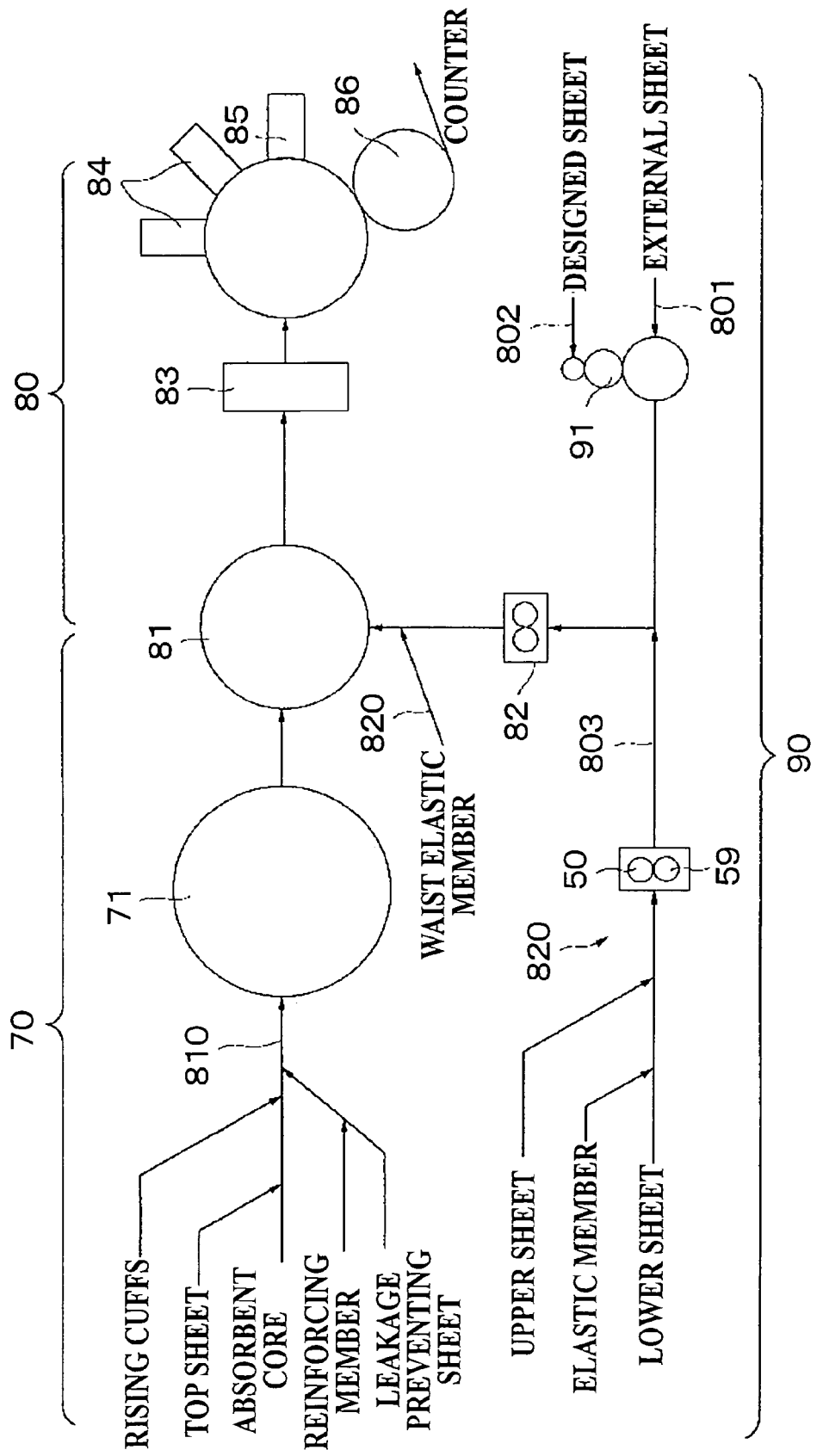
FIG. 33 is a flowchart showing a production line of the diaper.

FIG. 33 shows a fabrication flow of the pants-type disposable diaper, which is configured to be provided with a manufacturing and supplying line for the absorbent body 70, a manufacturing and supplying line for the external sheet 90 and a final treatment line 80.

In the manufacturing and supplying line for the absorbent body 70, first an absorbent core is supplied such that the longitudinal direction thereof is along the convey direction, the liquid permeable top sheet is overlaid thereon and fixed, and further the rising cuffs are disposed and fixed at both edge portions of this liquid permeable top sheet, respectively. These are disposed and fixed on the liquid impermeable back sheet supplied separately, and the absorbent body 810 is completed. In the case of the present example, the liquid impermeable back sheet is processed such that tenacity of the edge portions is strengthened by precedently folding back the both side end portions and sandwiching a reinforcing member such as colored urethane film or the like between them and gluing (the side edge portions may be highlighted or the tenacity may be strengthened by a color hot melt adhesion without using the reinforcing member).

The absorbent body 810 manufactured in this way is turned two-dimensionally at 90° at a 90° turning apparatus 71 such that the longitudinal direction thereof becomes an orthogonal orientation for the convey direction, and is conveyed to an external sheet attaching apparatus 81 in the final line 80.

On the other hand, in the manufacturing and supplying line for the external sheet 90, the underbelly portion elastic member, the hip portion elastic member and the waist elastic member are attached to the obi-like external sheet 801 which continues in the product width direction.

Figure 34:
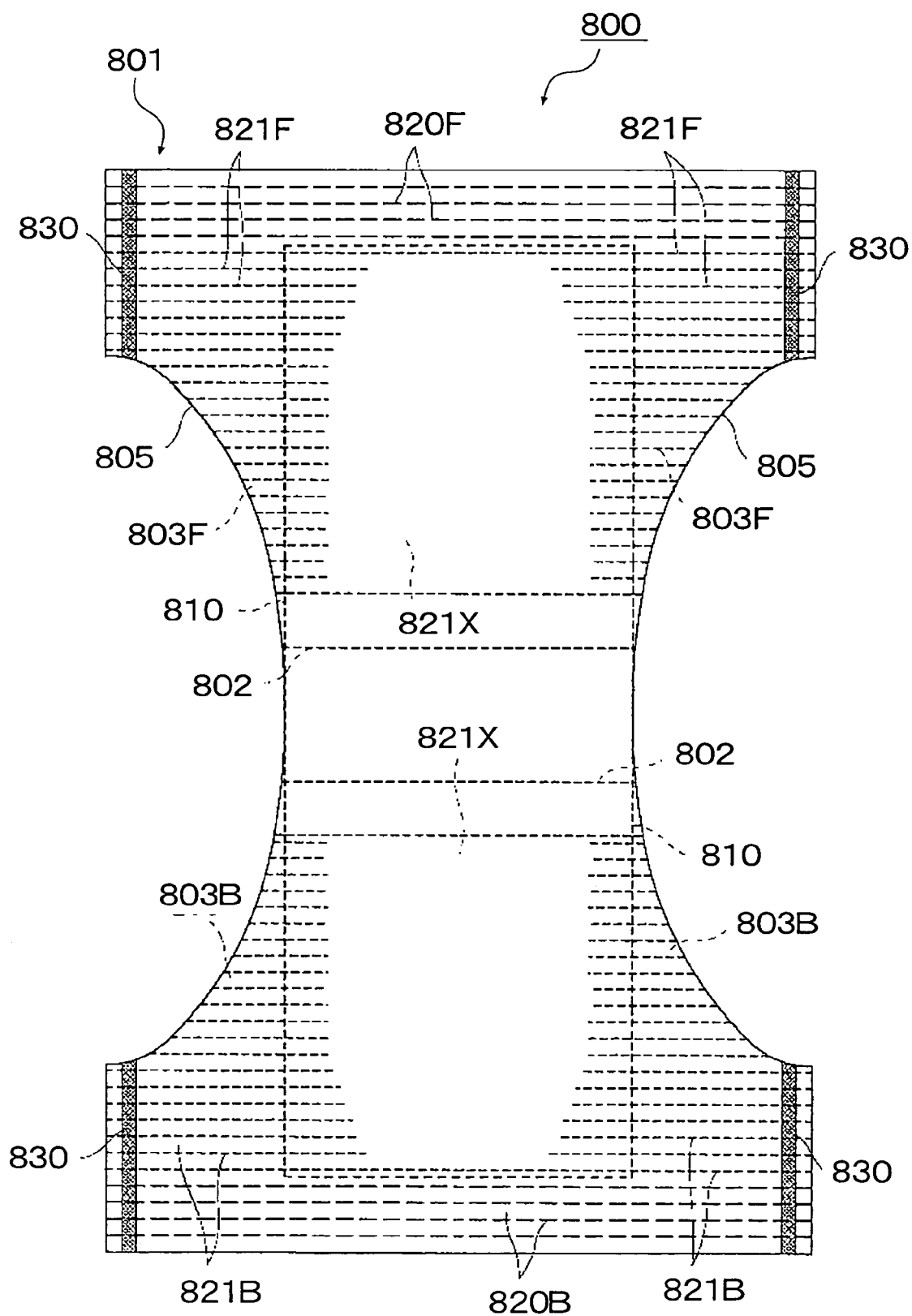
FIG. 34 is a development plan view showing the disposable diaper manufactured by the flow in FIG. 33.

Particularly, the obi-like external sheet 801 is first fed in a slip cutter apparatus 91. At this slip cutter apparatus 91, designed sheet 802 which is supplied separately is slipped and sequentially cut into the predetermined shape with supplying intervals, and as is also shown in FIG. 34, the cut designed sheets 802, 802 are disposed and fixed to the front side center width direction and the back side width direction center on the upper face of the obi-like external sheet 801 by the hot melt adhesive and the like. As the designed sheet, it is possible to use those where pictures and the like are given to film or the like of opaque materials.

Subsequently, the underbelly portion elastic sheet and the hip portion elastic sheet which are supplied from the supplying line 820 for the body periphery elastic member are attached to the external sheet 801, respectively.

In the present invention, in the supplying line 820 for the body periphery elastic member, according to the method for manufacturing of the present invention, each one continuous elastic member 803 for the underbelly portion or the hip portion is manufactured where a single or multiple elastic members 20 are sandwiched between the upper and lower sheets in the extended state to make the laminate, which is passed between the first roller 50 where multiple convex portions are disposed on the surface and the second roller 59 opposed to the first roller, and the elastic member 20 of this laminate is cut between the convex portions 52 of the first roller 50 and the second roller 59 by at least either one of pressing or heating to make the portions to be overlapped with the absorbent body discontinuous. For the manufacture of the elastic sheets for the underbelly and the hip portions, a separate line may be provided, or one manufactured in one line may be divided into two in the longitudinal direction.

The continuous elastic sheets 803 for the underbelly and hip portions manufactured in this way are attached to the predetermined sites of the front and back sides on the external sheet 801 continuously by the hot melt adhesive and the like.

Next, the external sheet 801 to which continuous elastic sheets for the underbelly and hip portions are attached is sequentially fed in a die cutter apparatus 82, sites corresponding to the leg opening portions 805 are hollowed out, subsequently thereon, the continuous waist elastic members 820 are continuously supplied to the predetermined sites of respective sides (e.g., materials of rubber threads, obi-like rubber or the like are supplied in parallel with multiple number intervals), and fixed with the hot melt adhesive. As the waist elastic member, it is also possible to utilize the elastic member of the present invention.

The external sheet 801 to which the above member attachment is given is subsequently fed in an external sheet attaching apparatus 81 in the final line 80. The absorbent body 801 which is separately fed in is disposed to the product width direction center corresponding site of the external sheet 810, and fixed with the hot melt adhesive or the like.

The external sheet 801 where the attachment of the various members is completed is folded into two by a folding apparatus 83 such that both joint portions 830 and 830 of the front side F and the back side B are overlapped, the both joint portions 830 and 830 are heat-sealed by a subsequent heat sealing apparatus 83, subsequently additional portion which is left for the convey are cut off at a final cutter 84 to form the sites corresponding to the waist opening end edge, and continuous products are cut and separated along the sites corresponding to side edge portion spacing thereof and cut to fit to the product dimension to make the individual diapers. After transcribing pictures, prints or the like on the surface of the external sheet 801 by a transcriber 85 if necessary, the individual diapers are sequentially sent to a counter not shown in the figure.

As shown at the developed state (front face side) in FIG. 34, in the disposable diaper manufactured in this way, the portion 821X corresponding to the width direction center of the absorbent body at the portion from one side joint portion 830 to the other side joint portion 830 of the front side F in the elastic members 821F and 821B of the underbelly portion elastic sheets 803F and 803B are cut and made discontinuous by the method of the present invention mentioned above, i.e., by passing the laminate between the first roller 50 where a plurality of convex portions are disposed on the surface and the second roller 59 opposed to the first roller, and cutting the elastic member of the laminate by either one of pressing or heating between the convex portions 52 of the first roller 50 and the second roller 59. The portion 821X corresponding to the width direction center of the absorbent body at the portion from one side joint portion 830 to the other side joint portion 830 of the back side B in the elastic members 821F of the hip portion elastic sheets 803B and 803B are cut and made discontinuous by the method of the present invention mentioned above, i.e., by passing the laminate between the first roller 50 where a plurality of convex portions are disposed on the surface and the second roller 59 opposed to the first roller, and cutting the elastic member of the laminate by either one of pressing or heating between the convex portions 52 of the first roller 50 and the second roller 59.

Other Embodiments

The pants-type disposable diaper of the present invention comprises the elastic portion where the elastic member is disposed along the width direction, and the non-elastic portion where no elastic member is disposed or the portion where the elasticity lowering member is given to the elastic member at least at the under waist portion, and the arrangement of the elastic members at the waist portion and the leg opening portions is not especially limited. The non-elastic portion could be present at the center of at least one of the front and back sides, and therefore, it is also possible to make the arranged form of the elastic members different at the front side F and back side B. The modes of the present invention other than the modes shown in the above embodiments are shown in FIGS. 35A to 35D. The mode in FIG. 35A is the mode where the arrangement of the leg opening portion elastic members 173 is the same as that in the first embodiment, and the waist elastic members 170F and 170B are not disposed at the center of both front and back sides. The mode in FIG. 35B is the mode where the waist elastic members 270F and 270B are not disposed at the center of the front and back sides, and the leg opening portion elastic members are disposed. The mode in FIG. 35C is the mode where the arrangement of each elastic member at the front side is the same as that in the first embodiment, however, the under waist portion elastic member 371B is also disposed at the center of the back side. It is added that the arranged mode of the elastic members is appropriate in this way. The present invention includes both cases where the under waist portion elastic member 371F, 371B end portion or the leg opening portion elastic member 373 end portion is overlapped with the side edge portion of the absorbent core and where it does not reach the side edge of the absorbent core and is separated.

In the above examples, the rectangular absorbent body is joined to the external sheet with nearly sandglass shape, however, it may be the mode where the liquid permeable top sheet with the same shape as the external sheet is provided and the absorbent body is provided between them. Additionally, it may be the mode where the external sheet and the absorbent body have no boundary and are integrated.

The sheet composing an outer surface of the product is one where two or three breathable and water-repellent non-woven fabrics are laminated and fixed in the above example, however, it may be a piece of non-woven fabric, and in this case, the elastic member can be joined to the use face side of the non-woven fabric. Further, it is possible to make the plastic sheet intervene at the intermediate of the laminated non-woven fabrics, and to attach it at the use face side of the back face side non-woven fabric.

The under waist portion elastic members may be arranged in a lattice netty pattern. One example thereof is the mode shown in FIG. 35D.

Figure 36A:
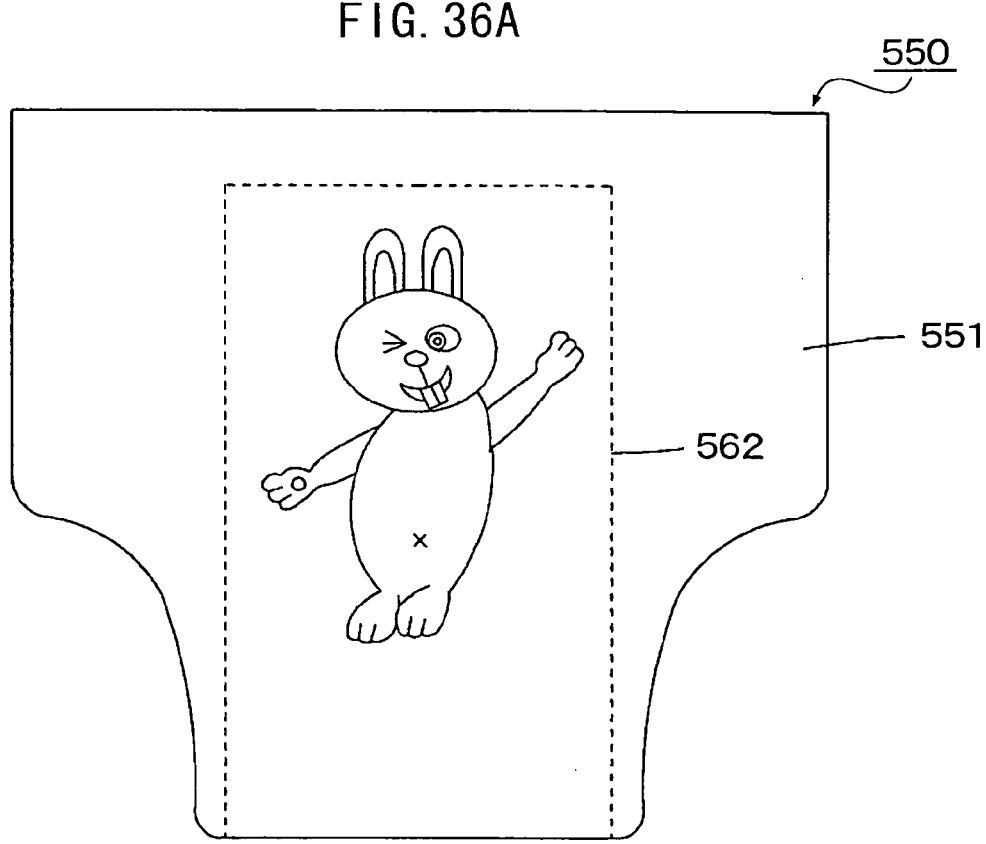
FIG. 36 is a figure showing a front and back design example of the disposable diaper product according to the invention.
Figure 36B:
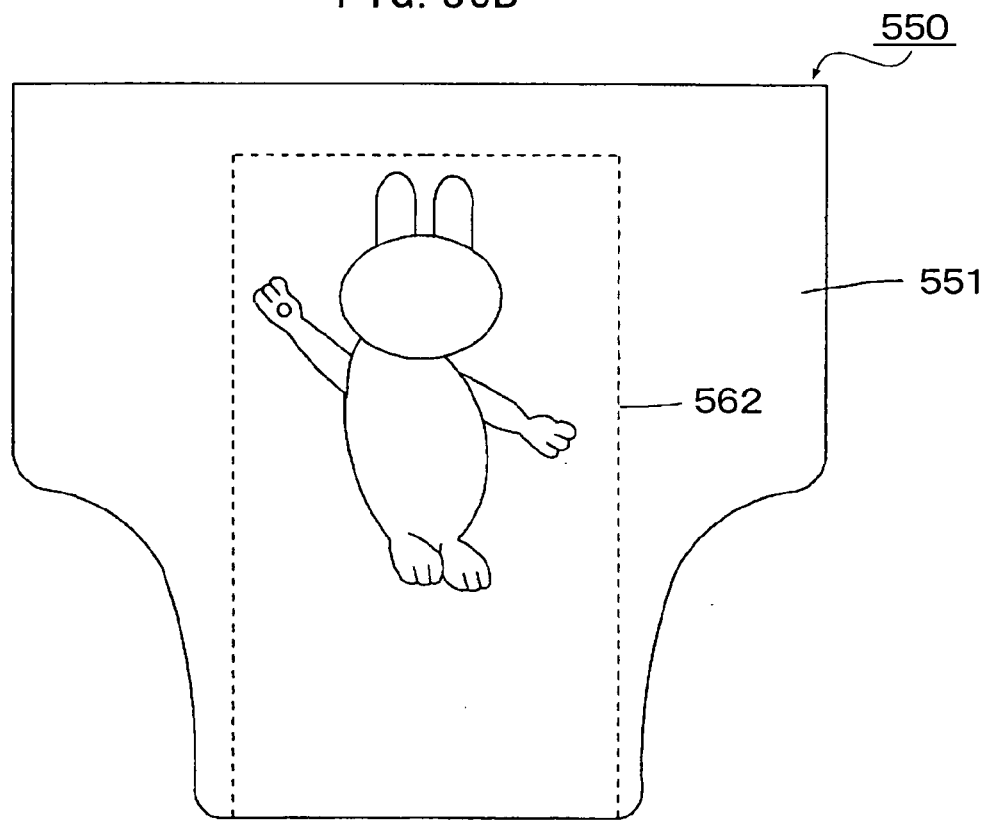

For the meantime, as shown in FIG. 36, designs such as characters or the like can be given to the back face side of the liquid impermeable back sheet 562 at the center of the product (nearly entire area of the absorbent core), for example by printing. Since the design portion has the absorbent core having a certain degree of stiffness, and the external sheet 551 is not deformed and no wrinkle occur according to the invention, the design portion becomes one where the design is clearly caught without deformation. In this way, the diaper becomes one where anyone can find the front and back at a glance, enjoy changing the diaper and the wearer will be pleased. The designed design sheet given the design may be made intervene between the external sheets. Design printing can be performed on the external sheet 551.

(Concerning Elastic Members)

Figure 37:
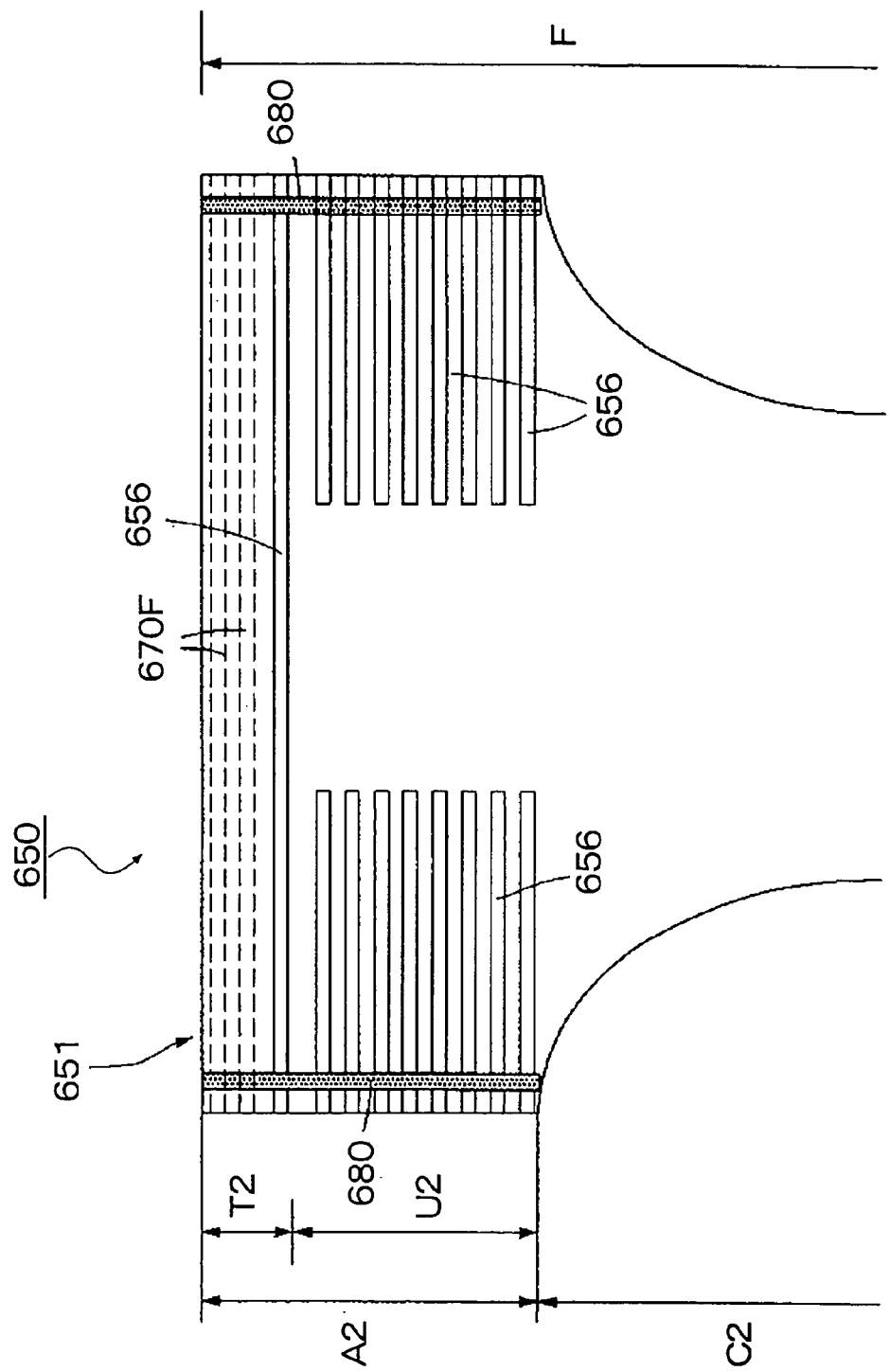
FIG. 37 is a development plan view showing an embodiment where another elastic member is installed.
Figure 38:
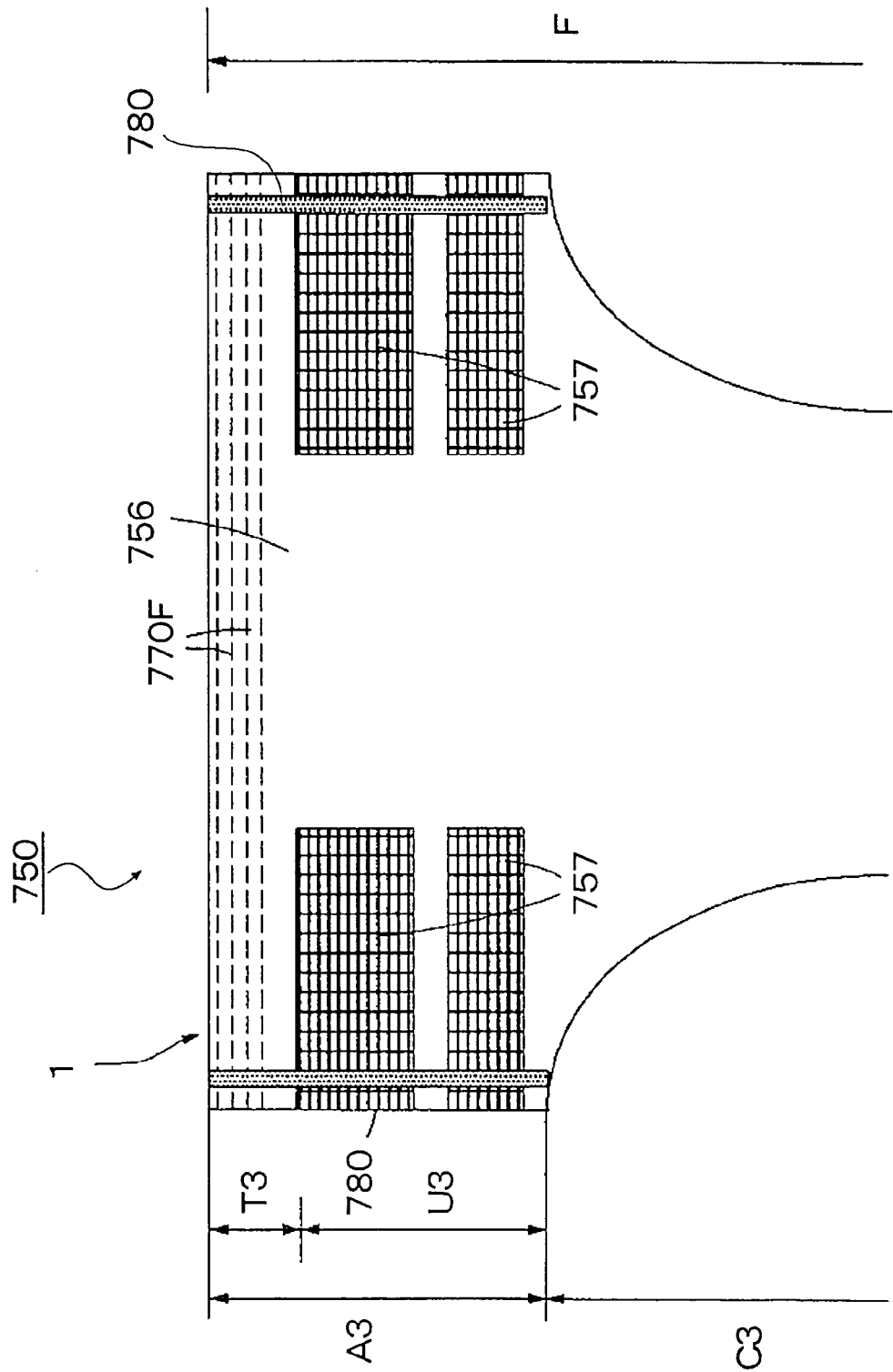
FIG. 38 is a development plan view showing an embodiment where the other elastic member is installed.
Figure 39:
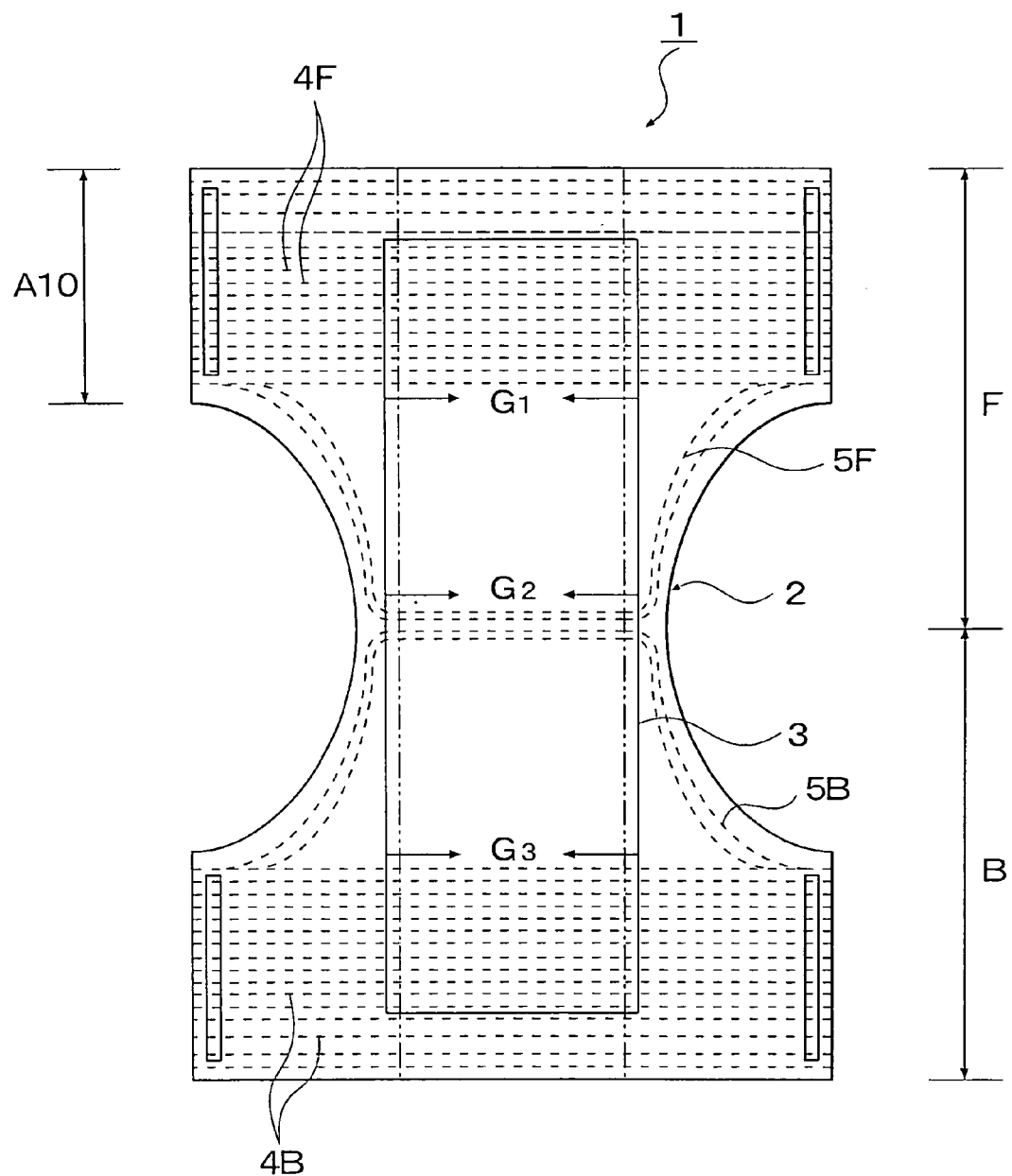
FIG. 39 is a development plan view showing a conventional disposable diaper known in the art.
Figure 40:
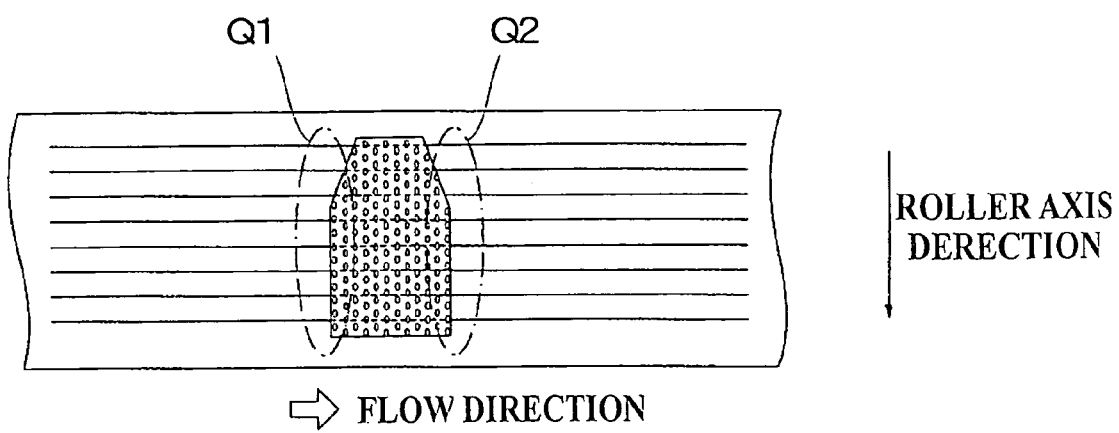
FIG. 40 is a cutting procedure schematic view showing the elastic member using the first roller where convex portions are disposed in a region with a cutting head home base shape in a constant pattern.

Additionally, as the above elastic members, it is possible to use those which are flexible and elastic such as urethane in addition to materials such as natural and synthetic rubbers. It is also possible to use thin obi-like flexible and elastic obis and sheet shape ones which is large in area. Examples thereof include an urethane obi, or a film, a sheet or the like. It is possible to select non-porous film or porous film as the film and further netty sheet and the like as the sheet accordingly. The arranged example of the non-porous film 656 was shown in FIG. 37. The arranged example of the netty sheet 757 was shown in FIG. 38. In these modes, it is also possible to make the configuration according to the present invention, i.e., where the difference between the product width in a normal state where the elastic portion contracts and the product width at the maximally extended state where the elastic portion is extended to the limit in the width direction is made from 100 to 250 mm, or the extensible force of the body peripheral region of the product is in the range of 300 to 600 gf when contracting 100 mm from the maximum extension state where the elastic portion is maximally extended to the peripheral direction and the extensible force of the body peripheral region of the product is made the range of 50 to 300 gf when contracting 150 mm.

In the above embodiments, the pants-type disposable diaper has been described as the example, however, the present invention can be applied to so-called taped disposable diaper, which is the type where both ventral right-and-left side edges and both dorsal right-and-left side edges are joined at the use of the diaper (wearing).

INDUSTRIAL APPLICABILITY

As described above, the disposable diaper of the present invention becomes one where wrinkles are not noticeable and looks of the product is simple, furthermore is one which is easy to be worn and to wear, furthermore is excellent in fitness, and especially is optimal for the pants-type disposable diaper.

What is claimed is:

1. A method for manufacturing an elastic sheet, comprising:
    making a laminate by a process comprising disposing a plurality of elastic members in an extended state between upper and lower sheets;
    passing the laminate between a first roller and a second roller opposed to the first roller, wherein the first roller includes a first region in which a plurality of convex portions are provided on a surface of the first roller and a second region in which the plurality of convex portions are not provided on a surface of the first roller, the convex portions are arranged at intervals in rows extending along an axial direction of the first roller, and the plurality of rows are arrayed along a circumferential direction of the roller in the first region; and
    cutting the elastic members of the laminate by the convex portions of the first roller using at least one of heat and pressure, wherein the convex portions are arranged so as to overlap along the circumferential direction of the first roller such that each of the elastic members is cut;
    wherein the cutting is performed such that portions of the laminate corresponding to the first region of the first roller where the elastic members are cut alternate with portions of the laminate corresponding to the second region of the first roller where the elastic members are not cut along a feeding direction in which the laminate is fed through the first and second rollers.

2. The method according to claim 1, wherein the plurality of rows of the convex portions include a plurality of standard rows having a given length along the axial direction of the first roller and a plurality of shorter rows that are shorter than the given length along the axial direction of the first roller.

3. The method according to claim 2, wherein the intervals along the axial direction between the convex portions in at least a plurality of the shorter rows are different from the intervals along the axial direction between the convex portions in the standard rows, such that a line pressure in the axial direction of each of the shorter rows, of said at least a plurality of the shorter rows, is nearly equal to a line pressure in the axial direction of each of the standard rows.

4. The method according to claim 2, wherein the intervals along the axial direction between the convex portions in at least a plurality of the shorter rows are set to satisfy:

$$Pi \approx PN \times Li/LN$$

where:
- $Pi=S+Di$, and $Pi$ is a disposition pitch of the convex portions in one of the shorter rows $i$;
- $PN=S+Dn$, and $PN$ is a disposition pitch of the convex portions in each of the standard rows;
- $S$ is a length of each of the convex portions in the axial direction;
- $Di$ is a distance between each two adjacent convex portions in the shorter row $i$;
- $Dn$ is a distance between each two adjacent convex portions in the standard rows;
- $Li$ is a length in the axial direction of the shorter row $i$; and
- $LN$ is a length in the axial direction of each of the standard rows.

5. The method according to claim 4, wherein the intervals along the axial direction between the convex portions in each of the shorter rows are set to satisfy:

$$Pi \approx PN \times Li/LN.$$

6. The method according to claim 4, wherein the intervals along the axial direction between the convex portions of a first plurality of the shorter rows are set to satisfy:

$$Pi \approx PN \times Li/LN,$$

and the intervals along the axial direction between the convex portions of a second plurality of the shorter rows are set to satisfy:

$$Pi=PN.$$

7. The method according to claim 1, wherein the process of making the laminate comprises coating an adhesive on at least one of the upper and lower sheets and sandwiching the elastic member between the upper and lower sheets.

8. The method according to claim 7, wherein the adhesive is provided continuously along the feeding direction.

9. The method according to claim 7, wherein the adhesive is provided discontinuously such that regions with the adhesive and regions without the adhesive alternate along the feeding direction.

10. The method according to claim 9, wherein the cutting of the elastic members is performed only in the regions without the adhesive.

11. The method according to claim 1, wherein the elastic members are shaped as filaments.

12. The method according to claim 1, wherein the elastic members are shaped in a lattice.

13. The method according to claim 1, wherein a length of each of the convex portions in the axial direction is $S$ and a width of each of the convex portions in the circumferential direction is $W$; and
    wherein $S$ is in a range of 1 mm to 25 mm, and $W$ is in a range of 0.5 mm to 15 mm.

14. The method according to claim 13, wherein $S$ is in a range of 5 mm to 25 mm.

15. The method according to claim 13, wherein each of the convex portions has a planar shape that is one of circular, linear, and polygonal.

16. The method according to claim 1, wherein the convex portions are arranged in a staggered pattern.

* * * * *